US008255462B2

(12) United States Patent
Kondo

(10) Patent No.: US 8,255,462 B2
(45) Date of Patent: Aug. 28, 2012

(54) INFORMATION PROCESSING SYSTEM AND INFORMATION PROCESSING APPARATUS

(75) Inventor: Tetsujiro Kondo, Tokyo (JP)

(73) Assignee: Sony Corporation, Tokyo (JP)

( * ) Notice: Subject to any disclaimer, the term of this patent is extended or adjusted under 35 U.S.C. 154(b) by 1558 days.

(21) Appl. No.: 10/494,598

(22) PCT Filed: Oct. 23, 2002

(86) PCT No.: PCT/JP02/10979
§ 371 (c)(1),
(2), (4) Date: May 5, 2004

(87) PCT Pub. No.: WO03/040940
PCT Pub. Date: May 15, 2003

(65) Prior Publication Data
US 2004/0268264 A1 Dec. 30, 2004

(30) Foreign Application Priority Data

Nov. 9, 2001 (JP) ................. P2001-343980

(51) Int. Cl.
G06F 15/16 (2006.01)
G06F 15/177 (2006.01)
G06F 3/00 (2006.01)
A61B 5/05 (2006.01)

(52) U.S. Cl. ........ 709/205; 709/204; 709/208; 709/219; 709/248; 715/733; 715/737; 715/741; 715/751; 600/407; 600/427

(58) Field of Classification Search .......... 709/200–253; 345/1.1–3.1; 715/733–759; 600/407, 427, 600/437; 606/41, 42
See application file for complete search history.

(56) References Cited

U.S. PATENT DOCUMENTS

| 5,855,553 | A | * | 1/1999 | Tajima et al. | 600/407 |
| 6,167,296 | A | * | 12/2000 | Shahidi | 600/427 |
| 6,331,181 | B1 | * | 12/2001 | Tierney et al. | 606/130 |
| 6,334,141 | B1 | * | 12/2001 | Varma et al. | 709/205 |
| 6,360,250 | B1 | * | 3/2002 | Anupam et al. | 709/204 |
| 6,364,888 | B1 | * | 4/2002 | Niemeyer et al. | 606/130 |

(Continued)

FOREIGN PATENT DOCUMENTS

EP 0 732 082 9/1996

(Continued)

OTHER PUBLICATIONS

Suzuki et al., Development of Teleassist Biopsy System With Remotely Conteolled Robot Arm, IEEE Tencon, 1999, pp. 1581-1583.*

(Continued)

Primary Examiner — Emmanuel L Moise
Assistant Examiner — Farzana Huq
(74) Attorney, Agent, or Firm — Frommer Lawrence & Haug LLP; William S. Frommer; Thomas F. Presson

(57) ABSTRACT

An information processing system and apparatus which have a plurality of actuators, a plurality of sensors, a signal processing unit, a control unit, and an integrating unit. Various types of signals are exchanged as necessary via a network. Actuators and sensors share processing through collaboration so that individual functionality is raised. The present invention can be achieved through a SHARN system (Sensor, Human, Actuator, Real world, and Network) which can be applied to surgery, Personal Digital Assistant design, and the like, for example.

43 Claims, 51 Drawing Sheets

U.S. PATENT DOCUMENTS

| | | | |
|---|---|---|---|
| 6,522,966 B2 * | 2/2003 | Nakano | 701/70 |
| 6,587,750 B2 * | 7/2003 | Gerbi et al. | 700/245 |
| 6,594,552 B1 * | 7/2003 | Nowlin et al. | 700/260 |
| 6,659,939 B2 * | 12/2003 | Moll et al. | 600/102 |
| 7,003,550 B1 * | 2/2006 | Cleasby et al. | 709/205 |
| 2002/0123825 A1 | 9/2002 | Ohtsuki | |
| 2002/0129106 A1 * | 9/2002 | Gutfreund | 709/205 |

FOREIGN PATENT DOCUMENTS

| | | |
|---|---|---|
| EP | 1 125 557 | 8/2001 |
| JP | 8-215211 | 8/1996 |
| JP | 08215211 A * | 8/1996 |
| JP | 8 297736 | 11/1996 |
| JP | 10 15251 | 1/1998 |
| JP | 10-264066 | 10/1998 |
| JP | 11 243508 | 9/1999 |
| JP | 2000-84871 | 3/2000 |
| JP | 2000-242333 | 9/2000 |
| JP | 2000 283785 | 10/2000 |
| JP | 2000-342498 | 12/2000 |
| JP | 2001-51964 | 2/2001 |
| JP | 2001 145637 | 5/2001 |
| JP | 2001 189927 | 7/2001 |
| JP | 2001 285894 | 10/2001 |
| JP | 2001 301552 | 10/2001 |
| JP | 2002-187078 | 7/2002 |
| WO | WO 00/30548 | 6/2000 |

OTHER PUBLICATIONS

Yamazawa, Kazumasa, et al., "Visual Navigation with Omnidirectional Image Sensor HyperOmni Vision," HyperOmni Vision, J79-D-11(5): 698-707, 1996.

* cited by examiner

TARGET PATH

OPERATING PATHS

AVERAGED PATH

DESIGN INFORMATION

DESIGN INFORMATION

INFORMATION PROCESSING SYSTEM AND INFORMATION PROCESSING APPARATUS

TECHNICAL FIELD

The present invention relates to an information processing system and an information processing device, and particularly relates to an information processing system and an information processing device enabling highly functional processing by, for example, multiple action means acting in response to operations of multiple users, or multiple detecting means for detecting the real world in which the multiple acting means act, cooperating to share the load of processing.

BACKGROUND ART

For example, with multiple processors (here, something which performs some sort of processing), performing a certain processing by sharing the load in parallel enables the processing speed to be increased by the order of the number of the multiple processors as compared to one processor performing the processing, according to simple arithmetic.

Now, regardless of whether the processing is carried out with one processor or the processing is shared among multiple processors, the obtained processing results are no different. Further, the functions of each processor in a case of performing processing by sharing between multiple processors are no different from the case of performing the processing with one processor alone.

That is to say, conventionally, however many processors are collected, only the overall processing speed increases according to the number of processors, and the functions of each processor do not change.

Now, it is known by experience that in the event that multiple humans come together to perform a task, individuals cooperating (collaborating) with each other enables each individual to perform work which exceeds the normal capabilities thereof.

Accordingly, it can be thought that in a case wherein multiple processors are collected, sharing the processing between the processors through collaboration would allow the functions of each processor to be increased, so as to exhibit overall processing functions exceeding the order of the number of the processors, and moreover to attach added value to the overall processing results.

Also, it can be thought that in the event of multiple humans gathering to perform a task, rather than gathering humans with the same attributes such as disposition, mindset, and sensitivity, gathering humans with different attributes will mutually stimulate one another, and further self-development even more.

Accordingly, it can be thought that with processors as well, rather than gathering multiple processors having the same functions, gathering processors having mutually different functions, and having the processors share the processing through collaboration, would increase the functions of each processor.

DISCLOSURE OF INVENTION

The present invention has been made in light of such a situation, and it is an object thereof to improve the functions of each by sharing processing among many through collaboration.

The information processing system according to the present invention comprises: a plurality of acting means which act corresponding to operations by a plurality of users; a plurality of detecting means for detecting the real world where the plurality of acting means act; and communication means for exchanging information between the plurality of acting means and the plurality of detecting means; wherein information is exchanged by the communication means and the plurality of acting means and the plurality of detecting means share processing through collaboration, whereby the plurality of acting means or the plurality of detecting means are more highly functional as compared to operating individually.

With a first information processing method according to the present invention, a plurality of acting means act corresponding to operations by a plurality of users; a plurality of detecting means detect the real world where the plurality of acting means act; and communication means exchange information between the plurality of acting means and the plurality of detecting means; wherein information is exchanged by the communication means and the plurality of acting means and the plurality of detecting means share processing through collaboration, whereby the plurality of acting means or the plurality of detecting means are more highly functional as compared to operating individually.

A first computer-readable program according to the present invention controls a computer such that a plurality of acting means act corresponding to operations by a plurality of users; a plurality of detecting means detect the real world where the plurality of acting means act; and communication means exchange information between the plurality of acting means and the plurality of detecting means; wherein information is exchanged by the communication means and the plurality of acting means and the plurality of detecting means share processing through collaboration, whereby the plurality of acting means or the plurality of detecting means are more highly functional as compared to operating individually.

A program of a first recording medium according to the present invention controls a computer such that a plurality of acting means act corresponding to operations by a plurality of users; a plurality of detecting means detect the real world where the plurality of acting means act; and communication means exchange information between the plurality of acting means and the plurality of detecting means; wherein information is exchanged by the communication means and the plurality of acting means and the plurality of detecting means share processing through collaboration, whereby the plurality of acting means or the plurality of detecting means are more highly functional as compared to operating individually.

The information processing device according to the present invention comprises: acting means which act corresponding to operations by users; detecting means for detecting the real world where the acting means act; and communication means for exchanging information between other acting means and other detecting means; wherein information is exchanged by the communication means and the plurality of acting means and the plurality of detecting means share processing with other acting means and detecting means through collaboration, whereby the plurality of acting means or the plurality of detecting means are more highly functional as compared to operating individually.

With a second information processing method according to the present invention, acting means act corresponding to operations by a plurality of users; detecting means detect the real world where the acting means act; and information is exchanged between the other acting means and the other detecting means; wherein the acting means and the detecting means share processing with other acting means and detecting means through collaboration, thereby becoming more highly functional as compared to operating individually.

A second computer-readable program according to the present invention controls a computer such that acting means act corresponding to operations by a plurality of users; detecting means detect the real world where the acting means act; and information is exchanged between the acting means and the detecting means; wherein the acting means and the detecting means share processing with other acting means and detecting means through collaboration, thereby becoming more highly functional as compared to operating individually.

A program of a second storage medium according to the present invention controls a computer such that acting means act corresponding to operations by a plurality of users; detecting means detect the real world where the acting means act; and information is exchanged between the acting means and the detecting means; wherein the acting means and the detecting means share processing with other acting means and detecting means through collaboration, thereby becoming more highly functional as compared to operating individually.

With the information processing system, first information processing method, first program, and program of first recording medium, according to the present invention, multiple acting means or multiple detecting means share processing through collaboration, so the functionality of the multiple acting means or multiple detecting means is raised beyond that of operating individually.

With the information processing device, second information processing method, second program and program of second recording medium, according to the present invention, acting means or detecting means share processing through collaboration with other acting means or detecting means, so the functionality is raised beyond that of operating individually.

BEST MODE FOR CARRYING OUT THE INVENTION

Figure 1:
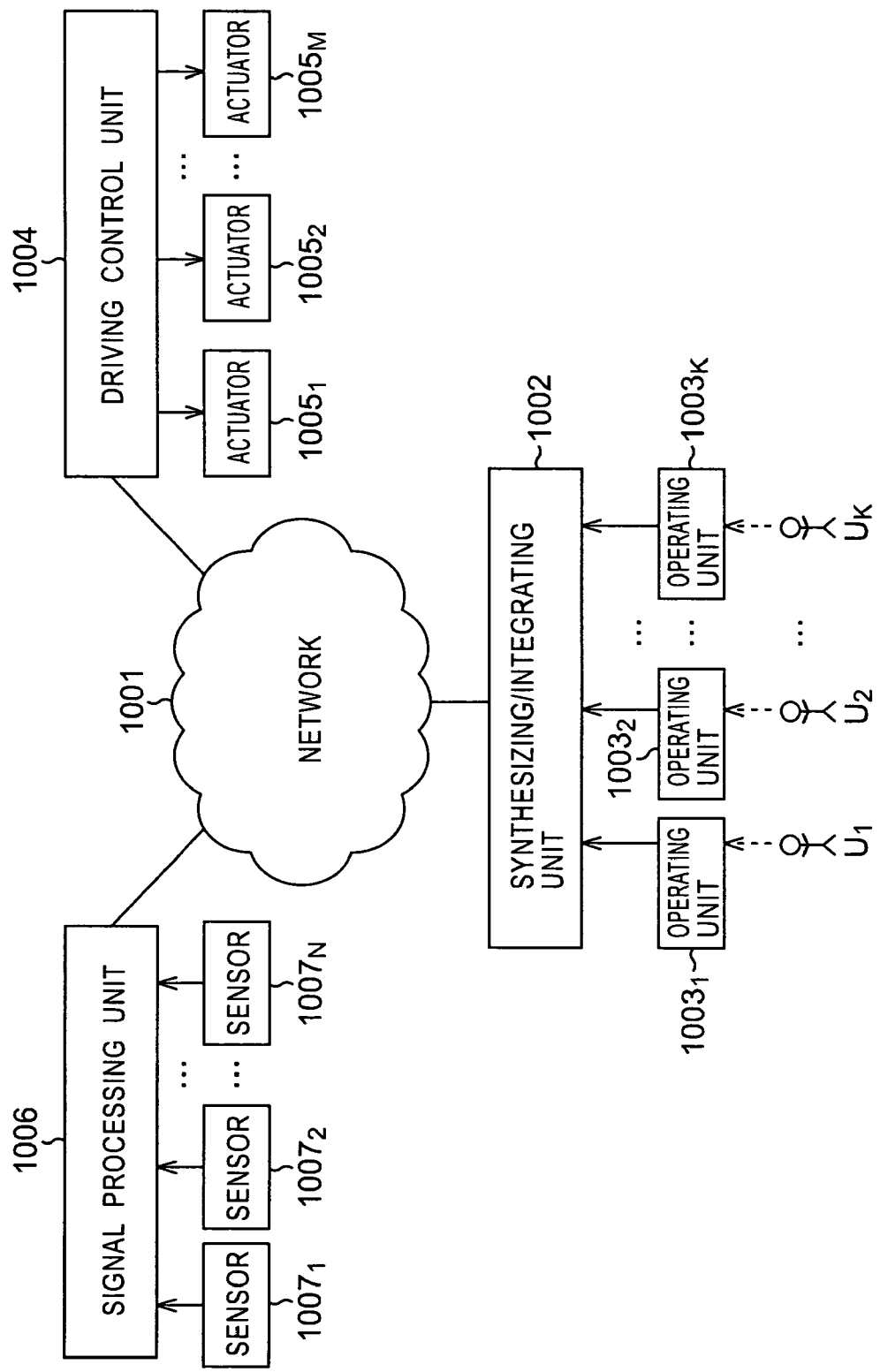
FIG. 1 is a block diagram illustrating a configuration example of an embodiment of a SHARN system to which the present invention has been applied.

FIG. 1 illustrates a configuration example of an embodiment of a SHARN system to which the present invention has been applied.

Now, "SHARN" of the SHARN system is an acronym of Sensor, Human, Actuator, real world (Real), and Network.

In FIG. 1, a network 1001 is a wide-area network to which a synthesizing/integrating unit 1002, driving control unit 1004, and signal processing unit 1006 are mutually connected, and signals (information) are exchanged between the synthesizing/integrating unit 1002, driving control unit 1004, and signal processing unit 1006 via this network 1001. Note that the network 1001 may be a line network, a wireless network, or a combined network of line and wireless. Also the network 1001 corresponds to the N for Network in "SHARN".

The synthesizing/integrating unit 1002 receives operating signals output from each of operating units $1003_1$ through $1003_K$, synthesizes or integrates these, and transmits to the network 1001. Here, synthesizing means placing multiple operating signals in a state wherein the operating signals cannot be separated, by weighting addition or the like, for example. Also, integrating means combining the multiple operating signals into one signal which can be separated into each operating signal, by multiplexing or the like, for example.

The operating unit $1003_k$ (wherein k=1, 2, ... K) is operated by a user $U_K$, and operating signals corresponding to the operations thereof are supplied to the synthesizing/integrating unit 1002. Note that with the embodiment in FIG. 1 (as with the later-described FIG. 2), a K number, which is a plurality, of operating units $1003_1$ through $1003_K$, are provided. The user $U_K$ which operates the operating unit $1003_K$ corresponds to the H for Human in "SHARN".

The driving control unit 1004 receives the signals supplied via the network 1001, and controls driving of actuators $1005_1$ through $1005_M$, based on these signals.

The actuator $1005_m$ (wherein m=1, 2, . . . , M) operates according to control from the driving control unit 1004, and accordingly acts upon objects in the real word in a predetermined way. With the first embodiment in FIG. 1 (as with the later-described FIG. 2), an M number, which is a plurality, of actuators $1005_1$ through $1005_M$, are provided. Also, the actuator $1005_m$ corresponds to the A for Actuator in "SHARN", and further, the real world in which the actuator $1005_m$ acts corresponds to the R for real world (Real) in "SHARN".

The signal processing unit 1006 receives detection signals from each of sensors $1007_1$ through $1007_N$, subjects top necessary signals processing and transmits to the network 1001.

The sensor $1007_n$ (wherein n=1, 2, . . . , N) detects the state in the real world where the actuator $1005_m$ acts, and supplies detecting signals representing the detected state to the signal processing unit 1006. Note that with the first embodiment in FIG. 1 (as with the later-described FIG. 2), an N number, which is a plurality, of sensors $1007_1$ through $1007_N$, are provided. Also, the sensor $1007_m$ corresponds to the S for Sensor in "SHARN", and further, the real world in which the sensor $1007_m$ acts corresponds to the R for real world (Real) in "SHARN".

Hereafter, the operating units $1003_1$ through $1003_K$ will be referred to operating unit 1003 unless there is a particular need to distinguish therebetween. In the same way, the actuators $1005_1$ through $1005_M$ will be described as actuator 1005, and the sensors $1007_1$ through $1007_N$ will be described as sensor 1007.

Figure 2:
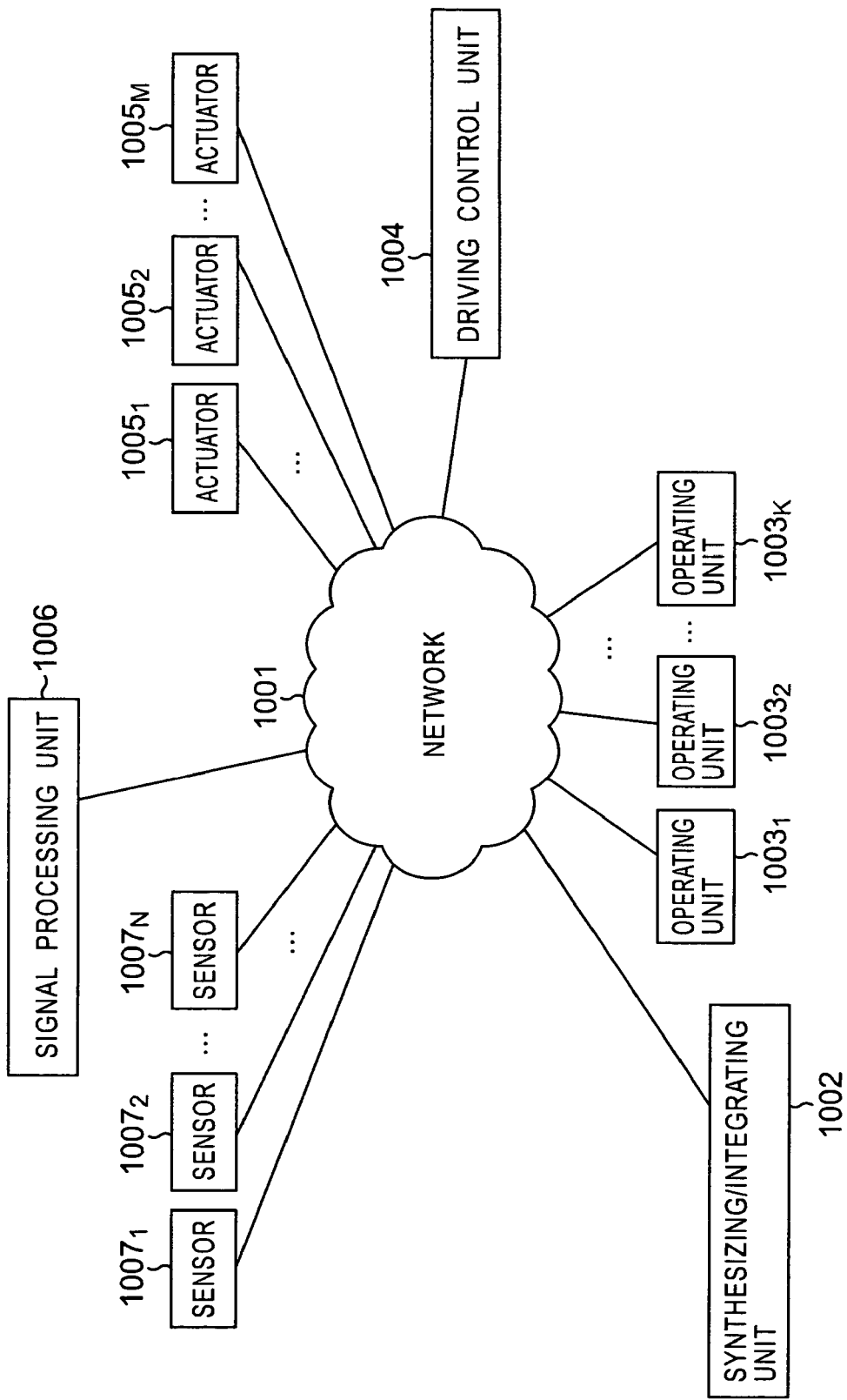
FIG. 2 is a block diagram illustrating a configuration example of another embodiment of the SHARN system to which the present invention has been applied.

Next, FIG. 2 illustrates a configuration example of another embodiment of the SHARN system to which the present invention has been applied. The portions in the drawing which correspond to the case in FIG. 1 are denoted with the same reference numerals, and description thereof will be omitted as appropriate in the following.

That is to say, with the first embodiment shown in FIG. 1, the operating unit 1003 is connected to the network 1001 via the synthesizing/integrating unit 1002, the actuator 1005 via the driving control unit 1004, and the sensor 1007 via the signal processing unit 1006, respectively, but with the second embodiment shown in FIG. 2, the operating unit 1003, actuator 1005, and sensor 1007 are directly connected to the network 1001.

Accordingly, with the second embodiment shown in FIG. 2, operating signals output from the operating unit 1003 are supplied to the synthesizing/integrating unit 1002 via the network 1001. Also, the signals for controlling driving of the actuator 1005 output from the driving control unit 1004 are supplied to the actuator 1005 via the network 1001, and detecting signals output from the sensor 1007 are supplied to the signals processing unit 1006 via the network 1001.

With the SHARN system configured as described above, various signals (information) are exchanged as necessary between the operating unit 1003, actuator 1005, and sensor 1007, through the synthesizing/integrating unit 1002, driving control unit 1004, and signal processing unit 1006, via the network 1001. Further, various signals are exchanged via the network 1001, through the synthesizing/integrating unit 1002 among the operating units $1003_1$ through $1003_K$, through the driving control unit 1004 among the actuators $1005_1$ through $1005_M$, and through the signal processing unit 1006 among the sensors 1007. Moreover, with the SHARN system, the functionality of each of the actuators $1005_m$ and each of the sensors $1007_n$ improve by the actuators 1005 and sensors 1007 collaborating to share processing. Further, as a result of the functionality of each of the actuators $1005_m$ and each of the sensors $1007_n$ improving, the processing results of the overall system are such that have added value added thereto.

Note that with the embodiments in FIG. 1 and FIG. 2, K which is the number of operating units 1003, M which is the number of actuators 1005, and N which is the number of sensors 1007, may be the same value, or may be different values.

Figure 3:
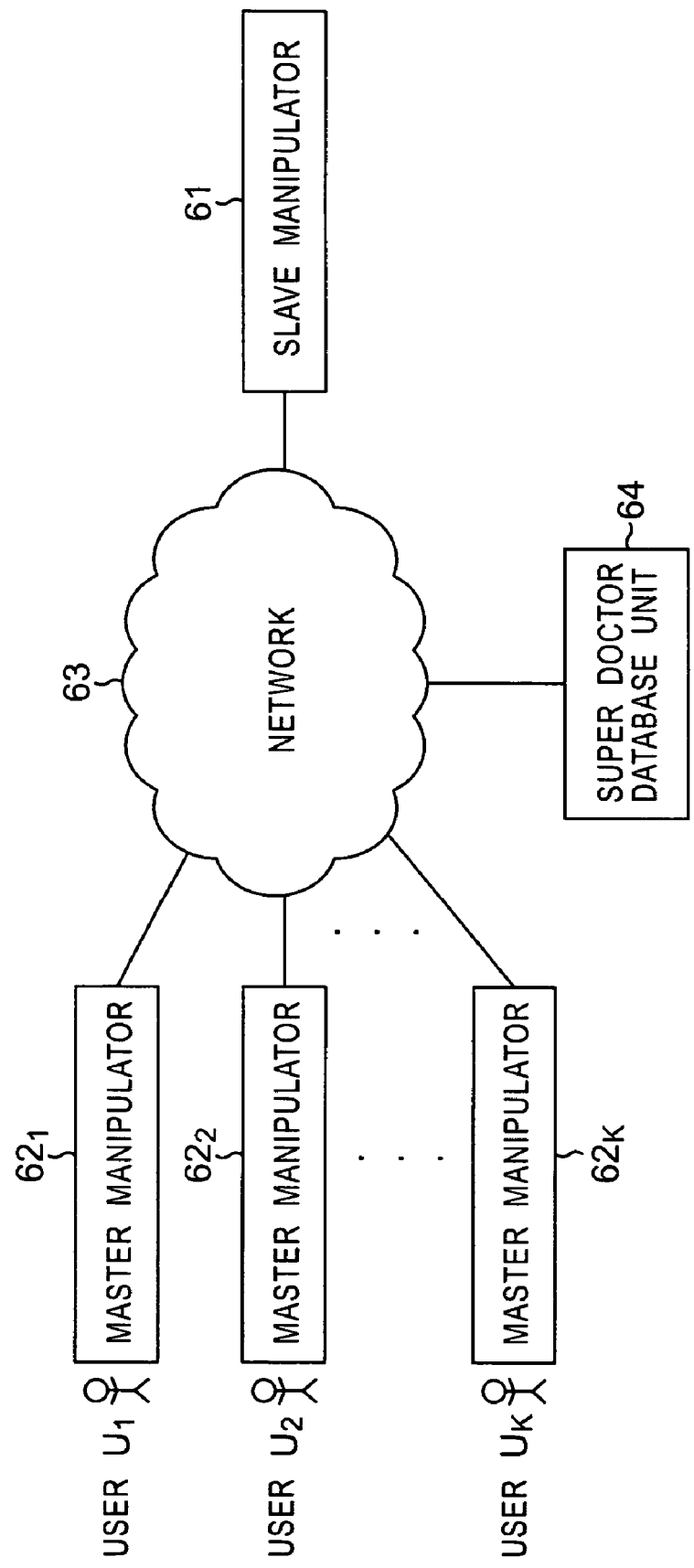
FIG. 3 is a block diagram illustrating a configuration example of an embodiment of a SHARN surgery system to which the SHARN system has been applied.

Next, FIG. 3 illustrates a configuration example of a SHARN surgery system as a surgery system to which the SHARN system has been applied.

This SHARN surgery system is a manipulator system for surgery, configured of a slave manipulator 61, master manipulators $62_1$ through $62_K$, a network 63, and a super doctor database unit 64.

The slave manipulator 61 acts based upon signals supplied via the network 63, and performs endermic surgery or the like on an animal such as a dog or the like, for example, which is the subject of surgery. Here, the slave manipulator 61 performs endermic surgery on an animal, but other arrangements may include the performing trimming or the like on the animal.

The master manipulator $62_k$ acts in response to operations of a user $U_k$ which is a veterinarian for example, and information supplied through the network 63 from the super doctor database 64. Also, the master manipulator $62_k$ detects the state of the actions, and transmits the results of detection to the super doctor database 64 via the network 63.

Note that with the embodiment shown in FIG. 3, a K number of manipulators $62_1$ through $62_K$ are provided, but these will hereafter be described as master manipulator 62 unless there is a particular need to distinguish therebetween.

The network 63 enables communication between the slave manipulator 61, the master manipulators $62_1$ through $62_K$, and the super doctor database 64.

The super doctor database 64 receives the state of action of the master manipulator 62 supplied through the network 63, and generates information relating to surgery based on that state. Further, the super doctor database 64 generates control signals based on the information relating to surgery and the state of the master manipulator 62, and controls the slave manipulator 61 by supplying this to the slave manipulator 61 through the network 63.

In the embodiment shown in FIG. 3, the master manipulator 62 corresponds to the operating unit 1003, actuator 1005, and sensor 1007 shown in FIG. 1 (and FIG. 2), the network 63 corresponds to the network 1001 in FIG. 1, and the super doctor database 64 corresponds to the synthesizing/integrating unit 1002, driving control unit 1004, and signal processing unit 1006.

Figure 4:
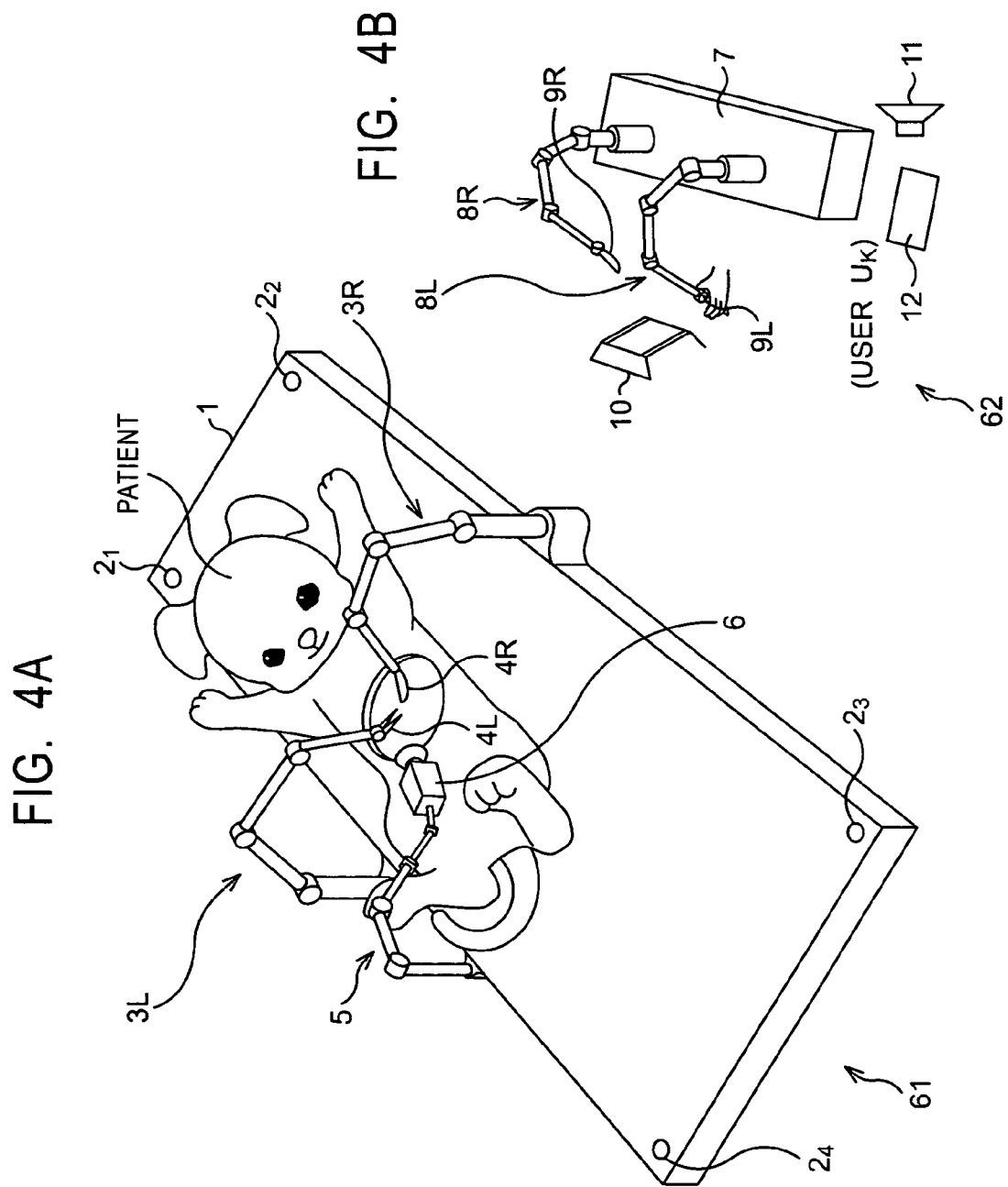
FIG. 4A is a perspective view illustrating an external configuration example of a slave manipulator 61.
FIG. 4B is a perspective view illustrating an external configuration example of a master manipulator 62.

Next, FIG. 4 illustrates an external configuration example of the slave manipulator 61 and the master manipulator 62 shown in FIG. 3.

That is to say, FIG. 4A illustrates an external configuration example of the slave manipulator 61, and FIG. 4B illustrates an external configuration example of the master manipulator 62, respectively.

With the slave manipulator 61 shown in FIG. 4A, a surgery table 1 has a rectangular shape, and a patient to be operated upon (a dog in the example in FIG. 4) is laid thereupon. Also, attached to the surgery table 1 are a slave manipulator unit 3L and a slave manipulator unit 3R.

The slave manipulator unit 3L and slave manipulator unit 3R (hereafter collectively referred to as slave manipulator unit 3 unless there is a particular need to distinguish therebetween) are remotely operated by a later-described master manipulator unit 8L and master manipulator unit 8R respectively, so as to perform endermic surgery on the patient laid on the surgery table 1.

The slave manipulator unit 3L is disposed on the left side of the surgery table 1 (to the left side viewing the surgery table 1 from above), and attached to the tip thereof is a tip unit 4L comprising treatment equipment such as gripping forceps, scalpel, suturing device, syringe, or the like.

The slave manipulator unit 3R is disposed on the right side of the surgery table 1, and attached to the tip thereof is a tip unit 4R comprising treatment equipment such as gripping forceps, scalpel, suturing device, syringe, or the like.

The slave manipulator unit 3 has a joint structure made up of multiple arms. Further, actuators 8 not shown in FIG. 4) are disposed at each joint portion of the slave manipulator 3, so that the arms move with a predetermined degree of freedom by the actuators acting, whereby the slave manipulator unit 3 is capable of assuming various attitudes.

Also, sensors are attached at the joint portions and necessary arm portions of the slave manipulator 3 to detect externally-applied force or torque (including magnitude and direction in either case) on the tip portions 4L and 4R and other portions, and further detecting the attitude of the slave manipulator unit 3 (not shown in FIG. 4).

Figure 7:
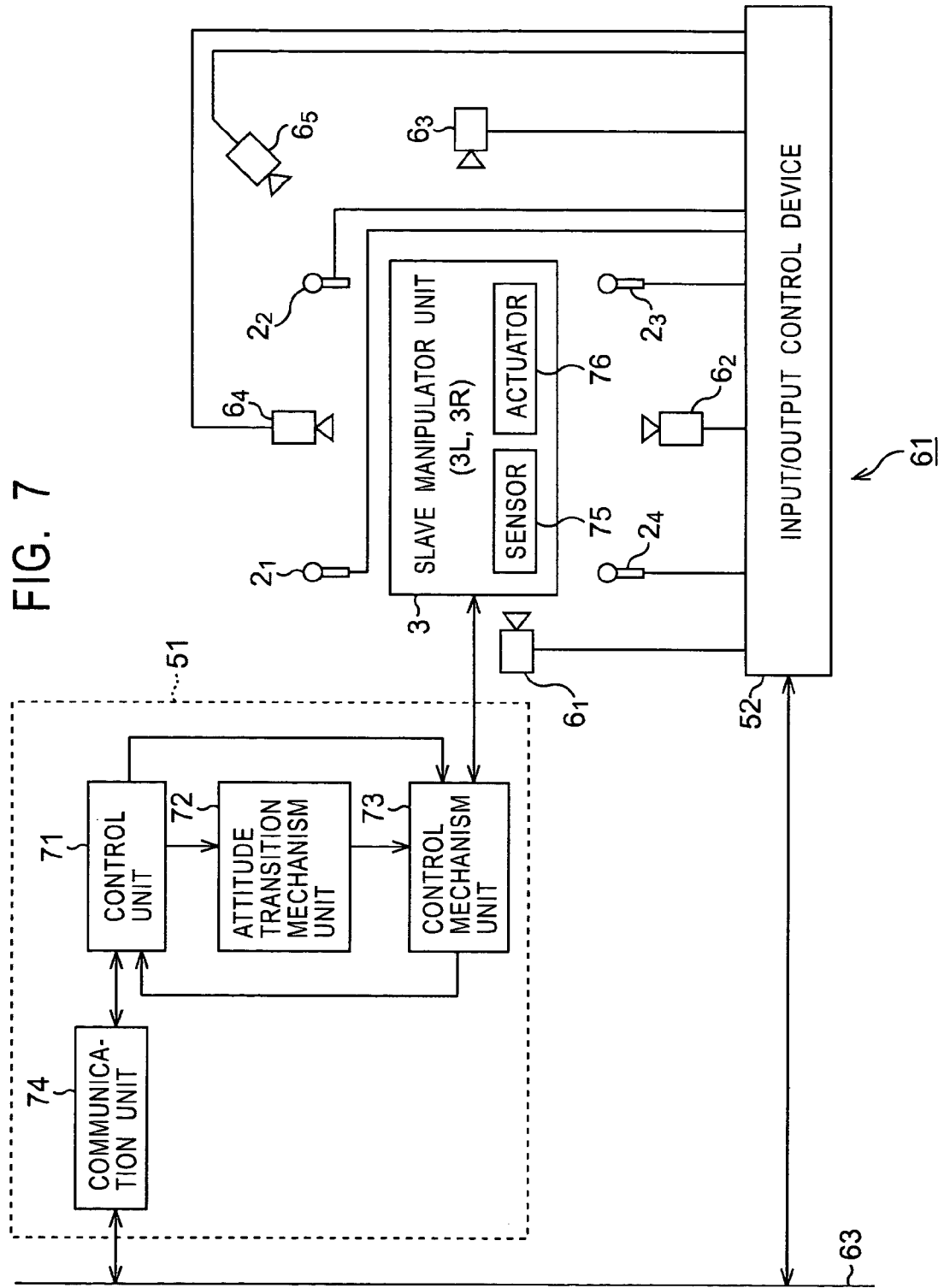
FIG. 7 is a block diagram illustrating an electrical configuration example of the slave manipulator 61.

Note that the sensors and actuators attached to the slave manipulator 3 are illustrated in the latter-described FIG. 7 as sensor 75 and actuator 76.

Further attached to the surgery table 1 is a camera unit 5 having a CCD (Charge Coupled Device) camera 6 attached to the tip thereof, for taking images of the inside of the abdominal cavity of the and so forth. Also, the surgery table 1 has attached to the four corners thereof microphones $2_1$ through $2_4$, for collecting sound.

Now, while FIG. 4A only shown one camera unit 5 in order to avid the drawing becoming complicated, there are multiple camera units 5 attached so as to enable observation of the conditions of the patient, the slave manipulator unit 3, and the like, from various directions.

Also, the camera unit 5 has a joint structure made up of multiple arms, further comprising unshown actuators provided at each of the joint portions. The arm moves with a predetermined degree of freedom due to the actuators acting, whereby the CCD camera 6 attached to the camera unit 5 can take pictures (perform imaging) from various viewpoints.

On the other hand, with the master manipulator 62 shown in FIG. 4B, disposed on an operating base 7 are master manipulator units 8L and 8R (hereafter collectively referred to as master manipulator unit 8 when appropriate) which are operated by the user U.

The master manipulator unit 8L is disposed to the left side of the operating base 7 (the left side with back to the operating base 7), with an operating unit 9L, which is held by the left hand of the user U and operated, attached to the tip thereof.

The master manipulator unit 8R is disposed to the right side of the operating base 7, with an operating unit 9R, which is held by the right hand of the user U and operated, attached to the tip thereof.

Now, the operating units 9L and 9R (hereafter collectively referred to as operating unit 9 as appropriate) correspond to the operating unit 1003 in FIG. 1.

The master manipulator unit 8 has a joint structure made up of multiple arms in the same way as the slave manipulator 3, so as to move with a predetermined degree of freedom. Accordingly, the operating unit 9L of the master manipulator 8L moves three-dimensionally due to operations by the left hand of the user U, and the operating unit 9R of the master manipulator 8R also moves three-dimensionally due to operations by the right hand of the user U.

Note that actuators (not shown in FIG. 4) are disposed at each joint portion of the master manipulator unit 8, so that the arm moves with a predetermined degree of freedom by the actuators acting, whereby the master manipulator unit 8 provides predetermined reactive force or pressing force to the user U. Here, the actuators provided on the joint portions correspond to the actuator 1005 shown in FIG. 1.

Also, sensors (not shown in FIG. 4) are provided to the joint portions and necessary arm portions of the master manipulator unit 8, for detecting (sensing) force or torque externally applied to the operating units 9L and 9R and other portions, and further for detecting the attitude of the master manipulator unit 8. Here, the sensors correspond to the sensor 1007 shown in FIG. 1.

Note that the sensors and actuators attached to the master manipulator 62 are illustrated in the later-described FIG. 8 as sensor 85 and actuator 86.

A monitor 10 is provided at the front side of the operating base 7 (the front direction of the user U in the event that the user U stands in front of the operating base 7 in order to operate the master manipulator unit 8), so that the user U can view an image displayed thereupon while operating the master manipulator unit 8. The monitor 10 displays images taken by the CCD camera 6 of the camera unit 5.

A speaker 11 is provided near the monitor 10, so that sound collected by the microphones $2_1$ through $2_4$ attached to the surgery table 1 of the slave manipulator 61 are output from this speaker 11.

Moreover, an operating panel 12 is provided near the monitor 10. The operating panel 12 has various types of switches and buttons and the like attached thereto, which are operated by the user as necessary. Examples of switches or the like on the operating panel 12 include an electric power switch, a switch for switching the image displayed on the monitor 10, and so forth.

The user U operating the manipulator 92 configured as described above stands between the operating base 7 and the monitor 10 with his/her back to the operating base 7, and three-dimensionally moves the operating unit 9L of the master manipulator unit 8L with his/her left hand, and also three-dimensionally moves the operating unit 9R of the master manipulator unit 8R with his/her right hand, while viewing the tip 4 of the slave manipulator unit 3 shown on the monitor 10.

In this case, operating signals corresponding to operations of the master manipulator unit 8 by the user U are supplied to the super doctor database 64 via the network 63, and the super doctor database 64 processes the operating signals to generate control signals for controlling the slave manipulator 61. The control signals are supplied from the super doctor database 64 to the slave manipulator 61 to via the network 63. At the slave manipulator 61, the slave manipulator unit 3 acts according to the control signals from the super doctor database 64. Accordingly, the tip 4L of the slave manipulator 3L moves synchronously with the movement of the operating unit 6L of the master manipulator 8L, and the tip 4R of the slave manipulator 3R moves synchronously with the movement of the operating unit 6R of the master manipulator 8R, thereby performing endermic surgery on the patient.

Now, there may be cases wherein there is offset between the actual operations and the intended operations, even in the event that a user $U_k$ attempts to operate the operating unit 9 of the master manipulator unit 8 so as to pass through a position of action of the operating unit 9, determined by the coordinates (X, Y, Z), in a state of rolling rotations, pitching rotations, and yawing rotations, each of predetermined angles, as a predetermined state.

Figure 5:
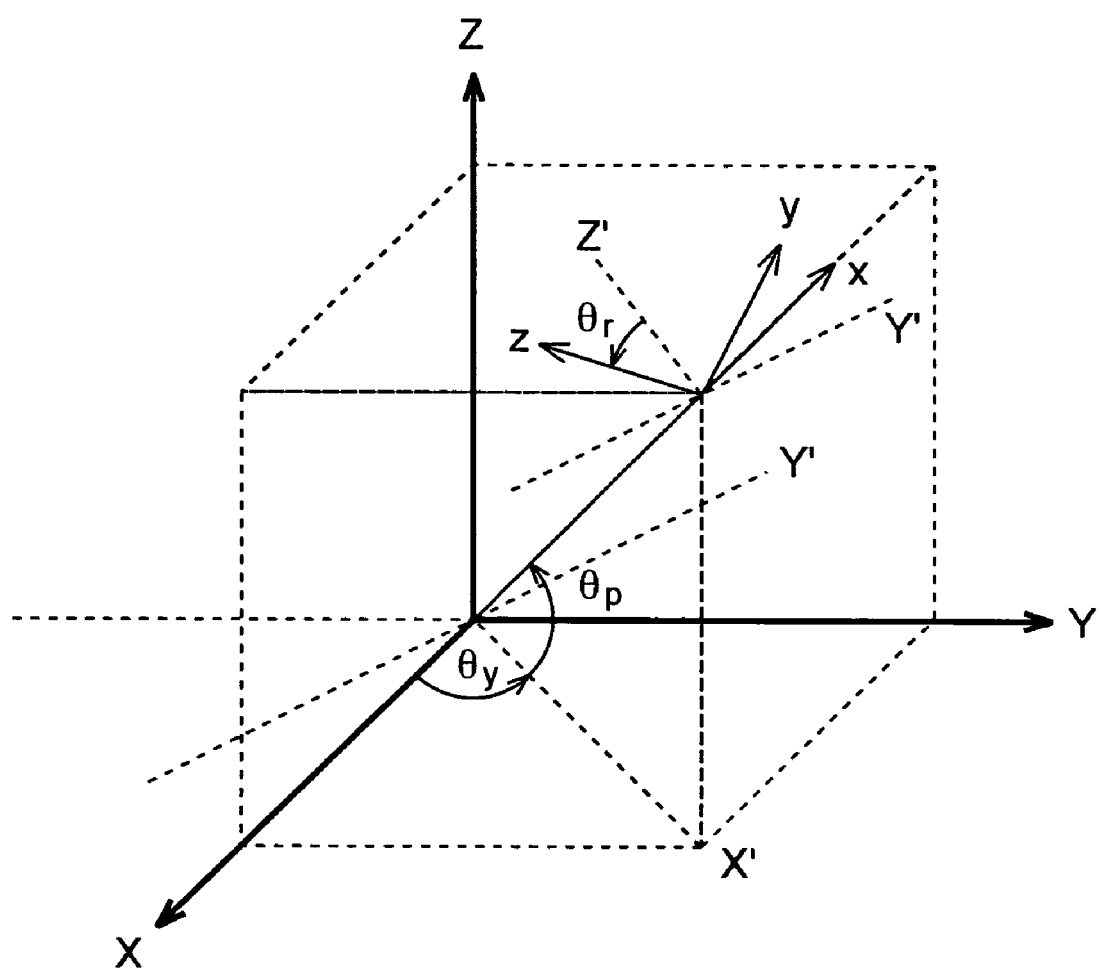
FIG. 5 is a diagram describing roll rotation, pitch rotation and yaw rotation.

Note that yawing rotation is rotation of the X axis and Y axis on the Z axis as shown in FIG. 5, and the rotation angle thereof is indicated in the drawing by $\theta_y$. Pitch rotation is rotation of the Z axis and the X axis which has been subjected to yawing rotation by $\theta_y$ (indicated by X' in the drawing), on the Y axis which has been subjected to yawing (indicated by Y' in the drawing), and the rotation angle thereof is indicated in the drawing by $\theta_p$. Rolling rotation is rotation of the Y axis which has been subjected to yawing rotation by $\theta_y$ (indicated by Y' in the drawing) and the Z axis which has been subjected to pitch rotation by $\theta_p$ (indicated by Z' in the drawing), on the X axis which has been subjected to yawing rotation by $\theta_y$ and then pitch rotation by $\theta_p$ (indicated by the X axis in the drawing), and the rotation angle thereof is indicated in the drawing by $\theta_r$.

Figure 6A:
FIG. 6A is a diagram illustrating a target path.

For example, in the event that the tip 4 of the slave manipulator unit 3 is to be moved from a predetermined position A to a position B over a path (target path) with a certain degree of curvature as shown in FIG. 6A, each of the users $U_1$ through $U_K$ attempt to move the operating unit 9 of the master manipulator unit 8 so as to trace a path corresponding to the target path (while there is difference in configuration according to the size of the slave manipulator unit 3 and the master manipulator unit 8, handled here as the same path for the sake of simplification). However, in reality, the operating unit 9 many be moved so as to trace a path (operating path) off from the target path indicated by the dotted line in FIG. 6B, as indicated by the solid line in FIG. 6B, although depending on the operating skill level of the users $U_1$ through $U_K$ with regard to the master manipulator unit 8 (operating unit 9).

Now, since offset between the operating path and the target path normally occurs randomly (since this does not occur with a certain tendency), a path closer to the target path can be obtained by averaging the multiple operating paths (the operating paths of each of the users $U_1$ through $U_K$ (FIG. 6B)).

Accordingly, the super doctor database unit 64 synthesizes the contents of operations at the master manipulators $62_1$ through $62_K$ (e.g., averages), and the slave manipulator 61 (slave manipulator unit 3) is remotely operated based on the synthesized (averaged) operating contents. Accordingly, with the slave manipulator 61, the tip 4 of the slave manipulator 3 can be moved to trace a path closer to the target path as shown in FIG. 6C.

Figure 6B:
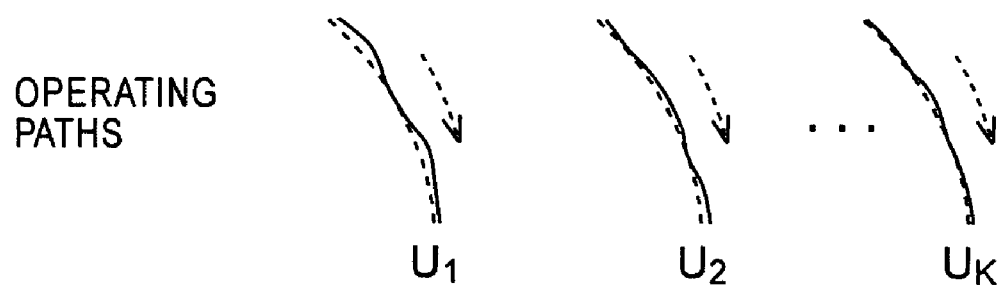
FIG. 6B is a diagram illustrating an operation path.
Figure 6C:
FIG. 6C is a diagram illustrating an averaged path.

Note that in FIG. 6A, the dotted line arrow indicates the direction of the path, the dotted line arrow in FIG. 6B indicates the direction of movement of the operating unit 9, and the dotted line arrow in FIG. 6C indicates the direction of movement of the tip 4.

Also, the super doctor database unit 64 stores surgery skill information which is skill-related information of past surgery performed by renowned surgeons from all over the world, classified by symptoms, for example, and the operating contents at the master manipulators $62_1$ through $62_K$ are corrected based on the surgery skill information, that is to say, the super doctor database unit 64 controls the slave manipulator 61 based on the stored surgery skill information as well as the contents of operation of the master manipulators $62_1$ through $62_K$.

Accordingly, with a SHARN surgery system, surgery of the highest level can be realized by users $U_1$ through $U_K$ which are veterinarians scattered throughout the world performing joint surgery by each operating the master manipulators $62_1$ through $62_K$, while making reference to surgery skill information.

Next, FIG. 7 illustrates an example of an electrical configuration of the slave manipulator 61 shown in FIG. 3.

A slave manipulator control device 51 is connected to the network 63, and controls the slave manipulator unit 3.

That is to say, the slave manipulator control device 51 is made up of a control unit 71, an attitude transition mechanism unit 72, a control mechanism unit 73, and a communication unit 74.

The control unit 71 takes attitude parameters serving as control signals sent out onto the network 63 by the super doctor database unit 64 and received by the control unit 71 through the communication unit 74, supplies these to the attitude transition mechanism unit 72 and also calculates the attitude parameters at the tip 4 of the slave manipulator unit 3 based on the output of the sensor 75 of the slave manipulator unit 3 supplied via the control mechanism unit 73 and sends these out on the network 63 via the communication unit 74.

Now, the attitude parameters of the tip 4 of the slave manipulator unit 3 are made up of, for example, the X-axial value, Y-axial value, and Z-axial value, for determining the position of the tip 4 (acting point), and the yaw angle $\theta_y$, pitch angle $\theta_p$, and roll angle $\theta_r$, which determine the angle of the tip 4, and so forth. The position of the tip 4 is the coordinates on the XYZ orthogonal coordinates system defined with a predetermined position in space where the tip 4 can move as the point of origin, and also, the angle of the tip 4 is defined shown in FIG. 5, with reference to the XYZ orthogonal coordinates system defined regarding the top 4, for example. Note that hereafter, both the position and angle together will be referred to as attitude, as appropriate.

The control unit 71 calculates the force F1 and torque T1 which the tip 4 of the slave manipulator unit 3 has externally received, based on the output of the sensor 75 of the slave manipulator unit 3, supplied via the control mechanism unit 73, and sends this out onto the network 63 via the communication unit 74.

The attitude transition mechanism unit 72 generates attitude transition information whereby the attitude of the tip 4 of the slave manipulator unit 3 makes transition from the current attitude to an attitude corresponding to the attitude parameters supplied from the control unit 71, and sends this to the control mechanism unit 73.

The control mechanism unit 73 generates control signals according to the attitude transition information from the attitude transition mechanism unit 72, and supplies this to the slave manipulator unit 3. The actuator 76 of the slave manipulator unit 3 is driven according to the control signals supplied from the control mechanism unit 73, and accordingly, the tip 4 assumes an attitude corresponding to the attitude parameters transmitted from the super doctor database unit 64.

The control mechanism unit 73 also acquires output of the sensor 75 of the slave manipulator unit 3, and supplies this to the control unit 71.

The communication unit 74 performs communication control via the network 63, and accordingly receives information transmitted from the network 63 and supplies this to the control unit 71, and also transmits information supplied from the control unit 71 to the network 63.

The input/output control device 52 is connected to the network 63, and transmits the audio data collected with each of the microphones $2_1$ through $2_4$, and the image data taken with the cameras $6_1$ through $6_5$, via the network 63.

Now, the cameras $6_1$ through $6_5$ correspond to the camera 6 in FIG. 4. Also, of the cameras $6_1$ through $6_5$, the cameras $6_1$ through $6_4$ are small-sized CCD cameras which take the affected portion or the like of the patient from predetermined viewpoints, and the camera $6_5$ is an all-directional camera which is capable of taking pictures of the entire periphery of the slave manipulator unit 4. Now, details of the all-direction camera will be described later.

Figure 8:
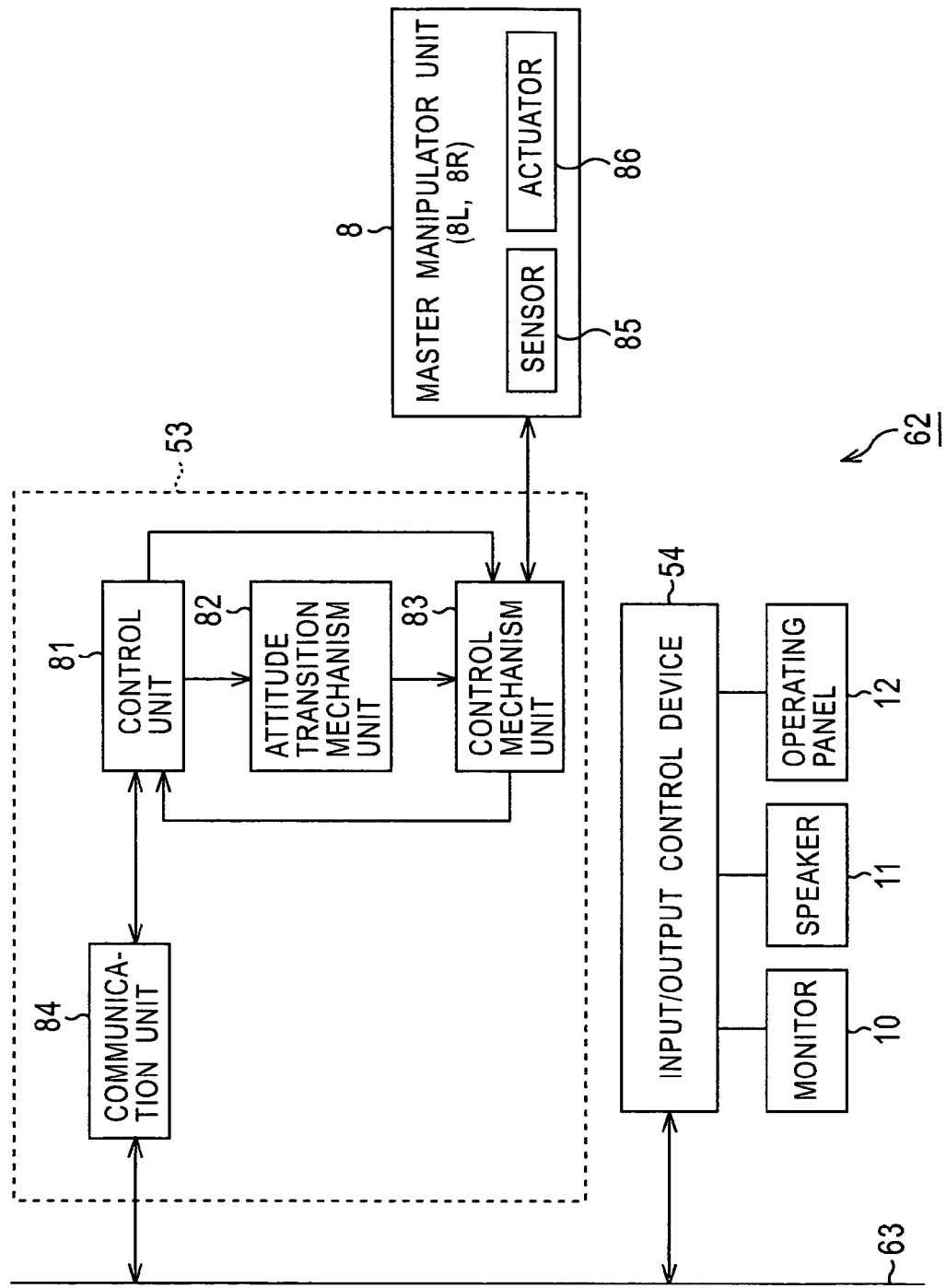
FIG. 8 is a block diagram illustrating an electrical configuration example of the master manipulator 62.

Next, FIG. 8 illustrates an example of the electrical configuration of the master manipulator 62 shown in FIG. 3.

The master manipulator control device 53 is connected to the network 63, and controls the master manipulator unit 8.

That is to say, the master manipulator control device 53 compromises a control unit 81, attitude transition mechanism unit 82, control mechanism unit 83, and communication unit 84.

The control unit 81 calculates the later-described force F0 and torque T0, based on the later-described reference attitude parameters obtained via the communication unit 84, and the force F1 and torque T1 (the force and torque externally applied to the tip 4 of the slave manipulator unit 3), and supplies this to the control mechanism unit 83.

Further, the control unit 81 calculates the attitude parameters of the operating unit 9 of the master manipulator unit 8, based on the output of the sensor 85 of the master manipulator unit 8 supplied via the control mechanism unit 83, and transmits these to the network 63 via the communication unit 84.

Now, the attitude parameters of the operating unit 9 of the master manipulator unit 8 are configured of coordinates made up of X-axial values, Y-axial values, and Z-axial values, determining the position of the operating unit 9 (acting point), the yaw angle $\theta_y$, pitch $\theta_p$, and roll $\theta_r$, determining the angle of the operating unit 9, and so forth, as with the attitude parameters of the tip 4 of the slave manipulator 3. The position of the operating unit 9 is coordinates on the XYZ orthogonal coordinates system defined with a certain position in space where the operating unit 9 can move as the point of origin, and also the angle of the tip 4 is defined as shown in FIG. 5 with reference to the XYZ orthogonal coordinates system defined regarding the operating unit 9, for example.

Also, the attitude parameters of the operating unit 9 of the master manipulator unit 8, and the attitude parameters of the tip 4 of the slave manipulator unit 3 described above, may be defined on the same XYZ orthogonal coordinates system, or may be defined on a different XYZ orthogonal coordinates system. Note however, that in the event of defining the attitude parameters of the tip 4 and the operating unit 9 on different XYZ orthogonal coordinates systems, the super doctor database unit 64 needs to recognize the correlation between the differing XYZ orthogonal coordinates systems.

The control mechanism unit 83 generates control signals following the force F0 and torque T0 supplied from the control unit 81, and sends this to the master manipulator 8. The actuator 86 of the master manipulator 8 is driven according to these control signals, and accordingly, the operating unit 9 of the master manipulator 8 provides the force F0 and torque T0 calculated by the control unit 81 to the user U operating the operating unit 9.

The control mechanism unit 83 also supplies the output of the sensor 85 of the master manipulator 8 to the control unit 81.

The communication unit 84 performs communication control via the network 63, receives information transmitted from the network 63, and supplies this to the control unit 81, and also transmits information supplied from the control unit 81 to the network 63.

The input/output control device 54 is connected to the network 63, and receives image data and audio data transmitted from the network 63 and supplies each to the monitor 10 and speaker 11. Accordingly, the images taken with the cameras $6_1$ through $6_5$ of the slave manipulator 61 are displayed on the monitor 10, and the audio collected with the microphones $2_1$ through $2_4$ of the slave manipulator 61 are output from the speaker 11.

Also, the input/output control device 54 receives operating signals which the operating panel 12 outputs under operations of the user U, and switches the image to be displayed on the monitor 10 or audio to be output from the speaker 11, according to the operating signals. Further, the input/output control device 54 transmits the operating signals from the operating panel 12 to the network 63 as necessary.

Figure 9:
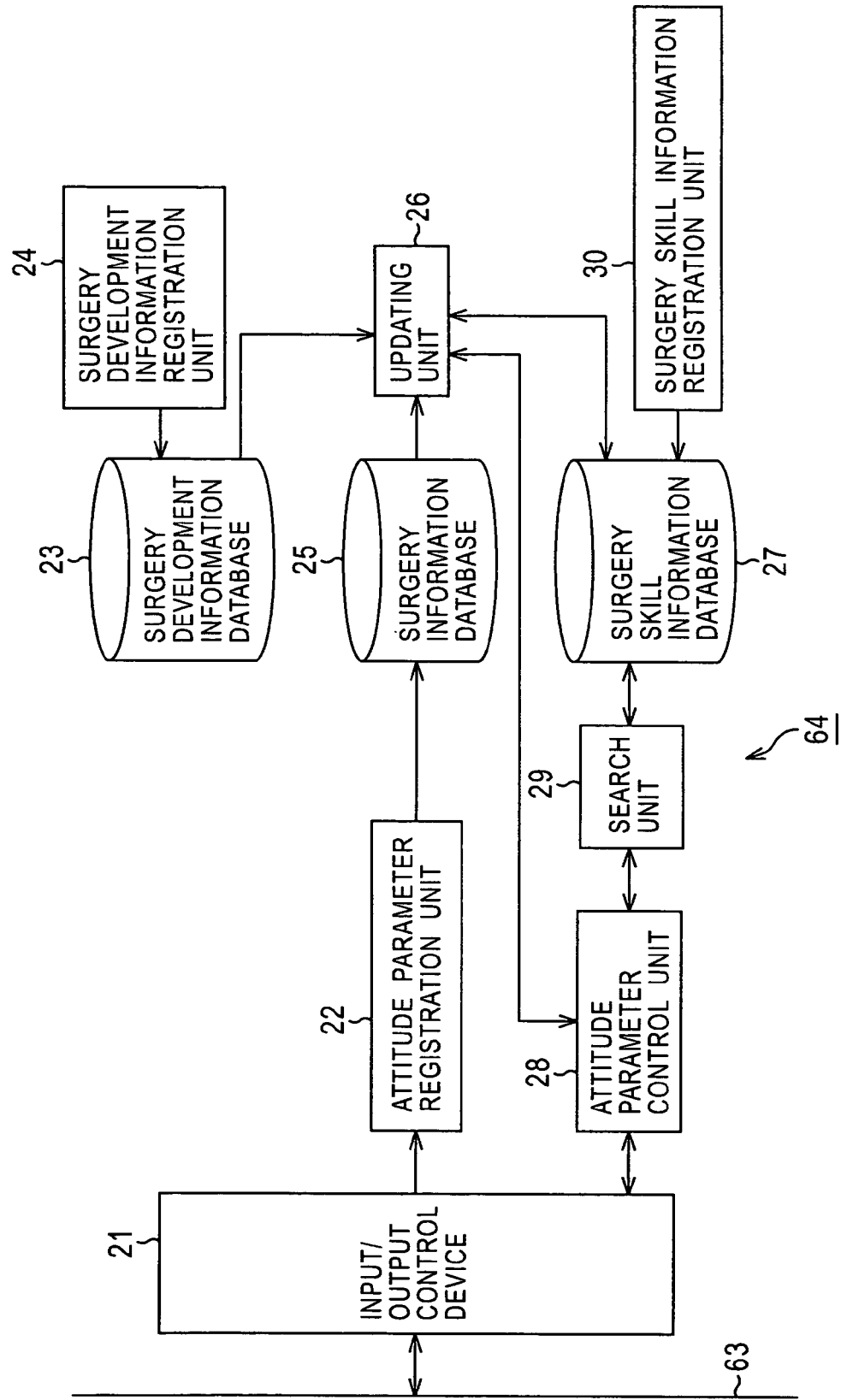
FIG. 9 is a block diagram illustrating an electrical configuration example of a super doctor database unit 64.

Next, FIG. 9 illustrates a configuration example of the super doctor database unit 64 shown in FIG. 3.

An input/output control unit 21 is connected to the network 63, and performs communication control via the network 63 such that information transmitted from the network 63 is received and supplied to an attitude parameter registration unit 22 and attitude parameter control unit 28, and information supplied from the attitude parameter control unit 28 is transmitted to the network 63.

Now, information which the input/output control unit 21 receives from the network 63 includes, for example, attitude parameters of the tip 4 which the slave manipulator 61 transmits, attitude parameters of the operating unit 9 which the master manipulator 62 transmits, and so forth.

The attitude parameter registration unit 22 recognizes what sort of surgical contents operations which the master manipulator 62 attempted based on the attitude parameters of the operating unit 9 sent from the master manipulator 62, supplied from the input/output control unit 21, and registers the recognized surgical contents and the attitude parameters as surgery information in the surgery information database 25.

A surgery development information database 23 stores surgery development information which is information relating to patients following surgery, regarding surgery performed in nations all over the world including surgery with SHARN surgery systems, for example, classified by surgery, for example.

A surgery development information registration unit 24 registers the surgery development information, by surgery, in the surgery development information database 23. Note that the surgery development information registration unit 24 collects, for example, surgery development information from databases in hospitals all over the world (including SHARN surgery systems) storing the contents of medical records and the like via the network 63, and registers this in the surgery development database 23. Also, the surgery development information registration unit 24 can also receive direct information of surgery development information by a predetermined operator performing operations, and in this case, the surgery development information registration unit 24 registers the directly-input surgery development information to the surgery development database 23.

A surgery information database 25 stores surgery information supplied from the attitude parameter registration unit 22.

An updating unit 26 determines whether or not surgery of the surgery contents indicated by the surgery information stored in the surgery information database 25 has succeeded, with reference to surgery development information of the surgery development database 23 and the surgery skill information database 27 is updated based on the surgery information for surgery which has been successful.

The surgery skill information database 27 stores surgery skill information which is information relating to surgical skill supplied from the updating unit 26 and a surgery skill information registering unit 30. That is, the surgery skill information database 27 stores information regarding each surgery, classified by symptoms, on the optimal way of operating the operating unit 9 for that surgery, operational contents to be restricted for operation of the operating unit 9, and so forth, as surgery skill information.

The attitude parameter control unit 28 receives attitude parameters of the operating unit 9 of the master manipulator 62 received by the input/output control device 21, corrects the received attitude parameters while making reference to the surgery sill information via a search unit 29 as necessary, and supplies these to the input/output control device 21 as reference attitude parameters.

The search unit 29 searches the surgery skill information stored in the surgery skill information database 27 under the control of the attitude parameter control unit 28, and supplies the searched results to the attitude parameter control unit 28.

The surgery skill information registering unit 30 is operated by a predetermined operator for example, and the surgery skill information corresponding to the operations thereof is registered in the surgery skill information database 27.

Next, the processing of the slave manipulator 61 shown in FIG. 7 will be described with reference to the flowchart in FIG. 10.

In step S1, the input/output control device 52 makes the microphones $2_1$ through $2_4$ and the cameras $6_1$ through $6_5$ operational, and starts transmission of the audio data collected with each of the microphones $2_1$ through $2_4$, and the image data taken with each of the cameras $6_1$ through $6_5$.

That is to say, the input/output control device 52 receives the audio data collected with each of the microphones $2_1$ through $2_4$, and the image data taken with each of the cameras $6_1$ through $6_5$, and transmits this to the super doctor database unit 64 via the network 63. Note that transmission of the image data and audio data continues until an operation is made at the operating panel 12 of the master manipulator (FIG. 8) to stop the transmission thereof, for example.

Further, in step S1, the slave manipulator control device 51 transmits the attitude parameters of the tip 4 of the slave manipulator unit 3 to the super doctor database unit 64.

That is to say, with the slave manipulator control device 51, the control mechanism unit 73 makes the sensor 75 of the slave manipulator unit 3 operational, receives the output thereof, and supplies this to the control unit 71. The control unit 71 obtains the attitude parameters of the tip 4 of the slave manipulator unit 3 based on the output of the sensor 75 supplied from the control mechanism unit 73, and supplies this to the communication unit 74. The communication unit 74 transmits the attitude parameters from the control unit 71 to the super doctor database unit 64 via the network 63.

Subsequently, as described later, the attitude parameters are transmitted from the super doctor database unit 64 via the network 63, so the communication unit 74 of the slave manipulator control device 51 awaits transmission of the attitude parameters from the super doctor database unit 64, the flow proceeds to step S2, and receives the attitude parameters.

The attitude parameters are supplied from the communication unit 74 to the control unit 71, and the control unit 71 controls the slave manipulator unit 3 in step S3 such that the tip 4 of the slave manipulator unit 3 assumes the attitude corresponding to the attitude parameters thereof.

Specifically, the control unit 71 of the slave manipulator control device 51 supplies the attitude parameters from the communication unit 74 to the attitude transition mechanism 72. The attitude transition mechanism 72 generates attitude transition information whereby the attitude of the tip 4 of the slave manipulator unit 3 makes transition from the current attitude to an attitude corresponding to the attitude parameters supplied from the control unit 71, and supplies these to the control mechanism unit 73.

The control mechanism unit 73 generates control signals following the attitude transition information from the attitude transition mechanism 72, and sends this to the slave manipulator unit 3. At the slave manipulator unit 3, the actuator 76 is driven according to the control signals from the control mechanism unit 73, and accordingly, the attitude of the tip 4 changes, so as to assume an attitude corresponding to the attitude parameters received with the communication unit 74, i.e., the attitude parameters transmitted from the super doctor database 64.

Next, the flow proceeds to step S4, where the slave manipulator control device 51 transmits the force F1 and torque T1 applied to the tip 4 externally (from the abdominal cavity of the patient) by the attitude of the tip 4 of the slave manipulator unit 3 being changed under the control in step S3, transmits these to the super doctor database unit 64 via the network 63 along with the attitude parameters of the tip 4.

That is to say, with the slave manipulator control device 51, the control mechanism unit 73 supplies the output of the sensor 75 to the control unit 71, and the control unit 71 calculates the force F1 and torque T1 externally applied to the tip 4, and the attitude parameters of the tip 4, from the output of the sensor 75. Further, the control unit 71 supplies the force F1 and the torque T1, and the attitude parameters, to the communication unit 74, and the communication unit 74 transmits the force F1 and the torque T1, and the attitude parameters, to the super doctor database unit 64 via the network 63.

Subsequently, the flow returns to step S2, and the same processing is repeated.

Accordingly, with the slave manipulator 61, surgery is performed on the patient by the tip 4 of the slave manipulator unit 3 changing in attitude corresponding to the attitude parameters transmitted from the super doctor database 64.

Next, the processing of the master manipulator 62 shown in FIG. 8 will be described with reference to the flowchart shown in FIG. 11.

As described later, the super doctor database unit 64 transmits the image data and audio data transmitted from the slave manipulator 61 to the master manipulator 62 via the network 63, and accordingly in step S21, reception of the image data and audio data is started.

That is to say, in step S21, the input/output control device 54 receives the image data and audio data transmitted from the super doctor database unit 64 via the network 63, and supplies the image data to the monitor 10 and the audio data to the speaker 11. Accordingly, images taken with the cameras $6_1$ through $6_5$ of the slave manipulator 61 (FIG. 7) is displayed on the monitor 10 and audio collected with the microphones $2_1$ through $2_4$ of the slave manipulator 61 are output from the speaker 11.

Further, as described later, the super doctor database unit 64 transmits the attitude parameters of the tip 4 transmitted from the slave manipulator 61 to the master manipulator 62 via the network 63, so in step S21, the master manipulator control device 53 receives the attitude parameters, and controls the attitude of the operating unit 9 of the master manipulator unit 8 based on the attitude parameters.

That is to say, with the master manipulator control device 53, the communication unit 84 receives the attitude parameters of the tip 4 of the slave manipulator unit 3 transmitted from the super doctor database unit 64 via the network 63, and supplies these to the control unit 81. The control unit 81 receives the attitude parameters from the communication unit 84, and supplies these to the attitude transition mechanism unit 82. The attitude transition mechanism unit 82 generates attitude transition information whereby the attitude of the operating unit 9 of the master manipulator unit 8 makes transition from the current attitude to an attitude corresponding to the attitude parameters supplied from the control unit 81, and supplies these to the control mechanism unit 83. The control mechanism unit 83 generates control signals according to the attitude transition information from the attitude transition mechanism unit 82, and sends this to the master manipulator unit 8. The actuator 86 of the master manipulator unit 8 is driven according to the control signals, and accordingly, the attitude of the operating unit 9 changes so as to assume the same attitude as the attitude of the tip 4 of the slave manipulator unit 3.

Subsequently, in step S22, the attitude parameters of the operating unit 9 of the master manipulator unit 8 are transmitted to the super doctor database unit 64 via the network 63.

Specifically, with the master manipulator control device 53, the control mechanism unit 83 receives output of the sensor 85 of the master manipulator unit 8, and supplies this to the control unit 81. The control unit 81 calculates the attitude parameters of the operating unit 9 of the master manipulator unit 8 from the output of the sensor 85, and supplies these to the communication unit 84. The communication unit 84 transmits the attitude parameters of the operating unit 9 from the control unit 81 to the super doctor database unit 64 via the network 63.

Now, due to the processing in this step S22, attitude parameters representing the attitude of the operating unit 9 which has been made to assume a certain attitude by the user U operating the operating unit 9 of the master manipulator 8 are transmitted to the super doctor database unit 64.

The flow then proceeds to step S23, where the communication unit 84 of the master manipulator control device 53 receives the attitude parameters of the tip 4 of the slave manipulator unit 3 transmitted from the super doctor database unit 64 via the network as reference attitude parameters, and the flow proceeds to step S24. In step S24, the communication unit 84 of the master manipulator control unit 53 receives the force F1 and the torque T1 which the tip 4 has received externally, that is transmitted from the super doctor database unit 64 along with the attitude parameters of the tip 4. The attitude parameters, and the force F1 and the torque T1 regarding the tip 4 are supplied from the communication unit 84 to the control unit 81, and the flow proceeds from step S24 to S25.

In step S25, the control unit 81 calculates the difference between the attitude parameters of the operating unit 9 obtained in step S22 and the reference attitude parameters obtained in step S23, and the flow proceeds to step S26.

In step S26, the control unit 81 calculates a force F2 and a torque T2 of a magnitude proportionate to the difference (offset) between the attitude parameters of the operating unit 9 and the reference attitude parameters calculated in step S25, but in a direction opposite to the direction of offset, and the flow proceeds to step S27.

In step S27, the control unit 81 adds force and torque proportionate to the force F1 and the torque T1 obtained in step S24, to each of the force F2 and torque T2 calculated in step S26, thereby calculating force F0 and torque T0 to be sensed by the user U operating the operating unit 9. That is to say, the control unit 81 calculates the force F0 and torque T0 according to Expression (1), for example.

$$F_0 = \alpha F_1 + F_2$$

$$T_0 = \beta T_1 + T_2 \quad (1)$$

Note that in the event that a greater force is necessary to move the operating unit 9 of the master manipulator unit 8, for example, as compared to directly moving the tip 4 of the slave manipulator unit 3 (that is to say, when heavy), α and β are values greater than 1, and in the event that a small force is sufficient for moving the operating unit 9 as compared to moving the tip 4 (that is to say, when light), α and β are values smaller than 1. Also, in the event of moving these with the same force, α and β are 1.

Subsequently, in step S28, the master manipulator unit 8 is controlled such that the user U operating the operating unit 9 of the master manipulator unit 8 senses the force F0 and torque T0 calculated in step S27.

That is to say, the control unit 81 supplies the reference attitude parameters obtained In Step S23 and the force F0 and torque T0 obtained in step S26 to the attitude transition mechanism unit 82. The attitude transition mechanism unit 82 generates something which is attitude transition information for moving the attitude of the operating unit 9 of the master manipulator unit 8 so as to make transition from the current attitude to the attitude corresponding to the reference attitude parameters supplied from the control unit 81, further including information of acceleration (including angular acceleration) whereby the user can be made to sense the force F0 and torque T0, and supplies those to the control mechanism unit 83. The control mechanism unit 83 generates control signals following the attitude transition information from the attitude transition mechanism unit 82, and sends this to the master manipulator unit 8. The actuator 86 of the master manipulator unit 8 is driven according to these control signals, and accordingly, the operating unit 9 changes the attitude thereof with a predetermined acceleration, and assumes the same attitude as the tip 4 of the slave manipulator unit 3 while causing the user U to sense the force F0 and torque T0.

Subsequently, the flow returns to step S22, and thereafter, the same processing is repeated.

As described above, the force F0 and torque T0 to be sensed by the user U are the added values of the force F2 and torque T2 in the opposite direction to the offset with a magnitude proportionate to the magnitude of the offset calculated in step S25, and the force and torque proportionate to the force F1 and torque T1 which the tip 4 of the slave manipulator unit 3 has received, thereby enabling the user U to be caused to be conscious of the offset between the attitude parameters of the operating unit 9 and the referenced attitude parameters, and the reactive force at the tip 4 of the slave manipulator unit 3.

Accordingly, in the event that the user U operates the operating unit 9 of the master manipulator unit 8 so as to assume an attitude different from the attitude corresponding to the reference attitude parameters, the greater the different in attitude is, a great reactive force is received, so the user can recognize in a sensory manner how far his/her operations are from the actual attitude of the tip 4 of the slave manipulator unit 3.

Or, the user U can be made to sense only the force F2 and torque T2, for example.

Figure 12:
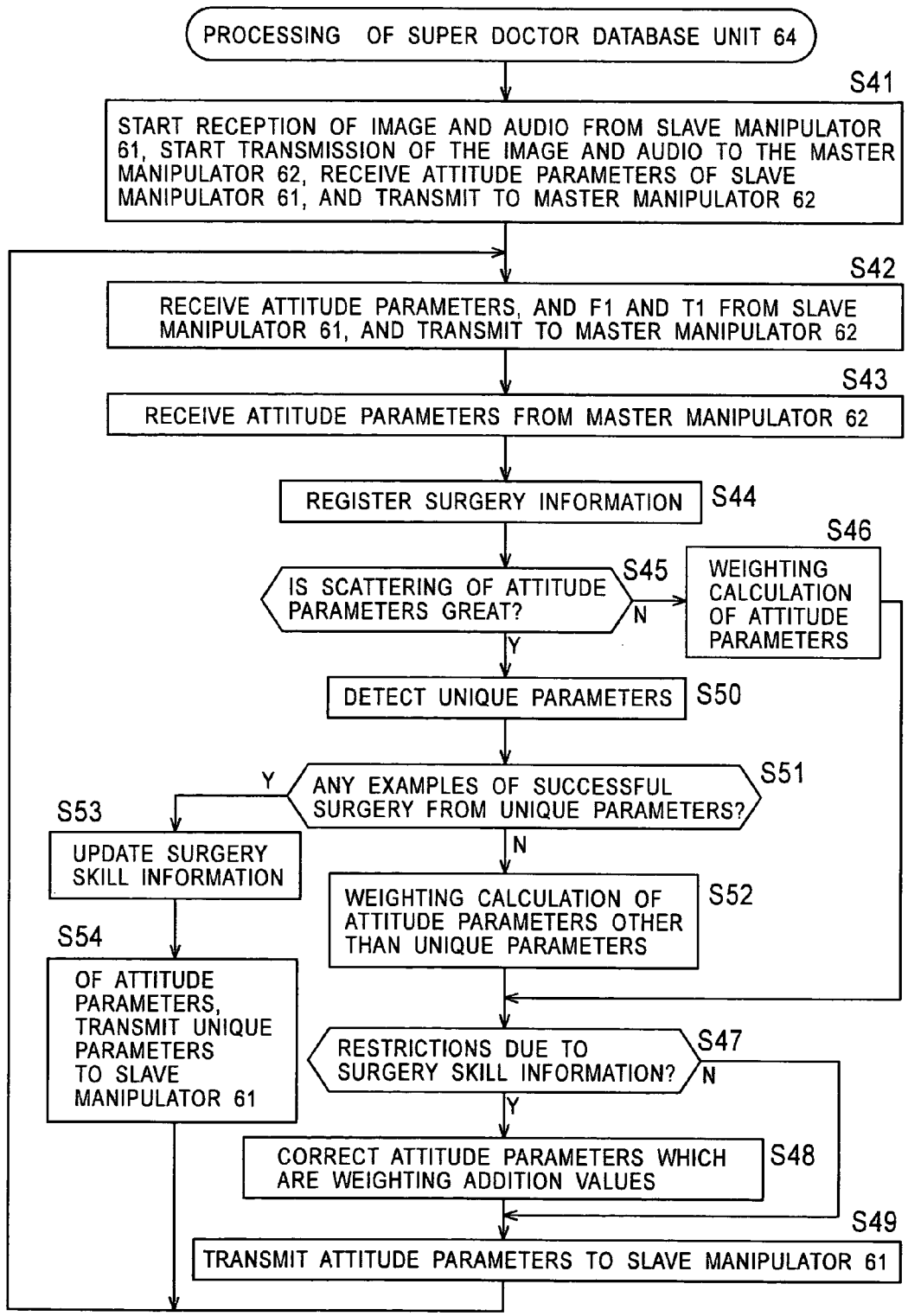
FIG. 12 is a flowchart describing the processing of the super doctor database unit 64.

Next, the processing of the super doctor database unit 64 shown in FIG. 9 will be described with reference to the flowchart in FIG. 12.

First, in step S41, the input/output control device 21 starts reception of the image data and audio data from the slave manipulator 61 and transmission of the image data and audio data to the master manipulator 62.

Figure 10:
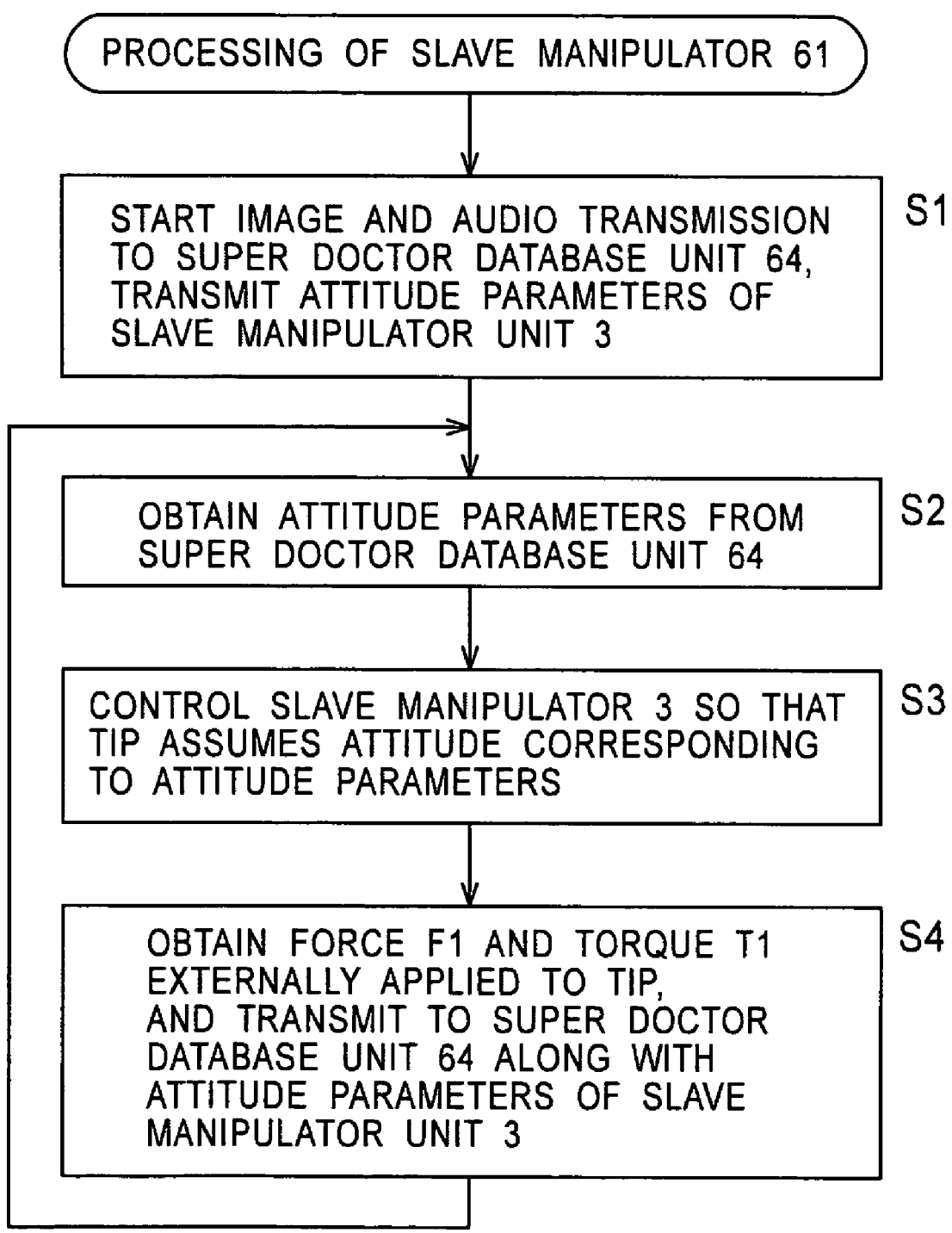
FIG. 10 is a flowchart describing the processing of the slave manipulator 61.

That is, as described in FIG. 10, in step S1, at the slave manipulator 61 (FIG. 7), transmission of the image data taken with the cameras $6_1$ through $6_5$ and audio data collected with the microphones $2_1$ through $2_4$ to the super doctor database unit 64 is started, so the input/output control device 21 of the super doctor database unit 64 starts reception of the image data and audio data transmitted from the slave manipulator 61 via the network 63.

Further, the input/output control device 21 starts transmission of the image data and audio data received from the slave manipulator 61 to the master manipulator 62. Thus, reception of the image data and audio data transmitted from the input/output control device 21 is started as the master manipulator 62, in step S21 in FIG. 11 described above.

Also, in step S41, the input/output control device 21 receives the attitude parameters transmitted from the slave manipulator 61 in step S1 in FIG. 10 (the attitude parameters of the tip 4 of the slave manipulator unit 3), and transmits the attitude parameters thereof to the master manipulator 62 as reference attitude parameters. Now, the reference attitude parameters are received at the master manipulator 62 instep S21 in FIG. 11 described above, and accordingly, the operating unit 9 (the operating unit 9 of the master manipulator unit 8) assumes an attitude corresponding to the reference parameters, i.e., the same attitude as the attitude of the tip 4 of the slave manipulator unit 3.

Subsequently, the flow proceeds to step S42, where the input/output control device 21 awaits and receives the attitude parameters regarding the tip 4 and the force F1 and torque T1 from the slave manipulator 61, transmitted in step S4 in FIG. 10, and transmits the attitude parameters as reference attitude parameters along with the force F1 and torque T1 to the master manipulator 62. Now, at the master manipulator 62, the attitude parameters regarding the tip 4 are received in step S23 in FIG. 11, and the force F1 and torque T1 regarding the tip 4 are received in step S24 in FIG. 11.

Figure 11:
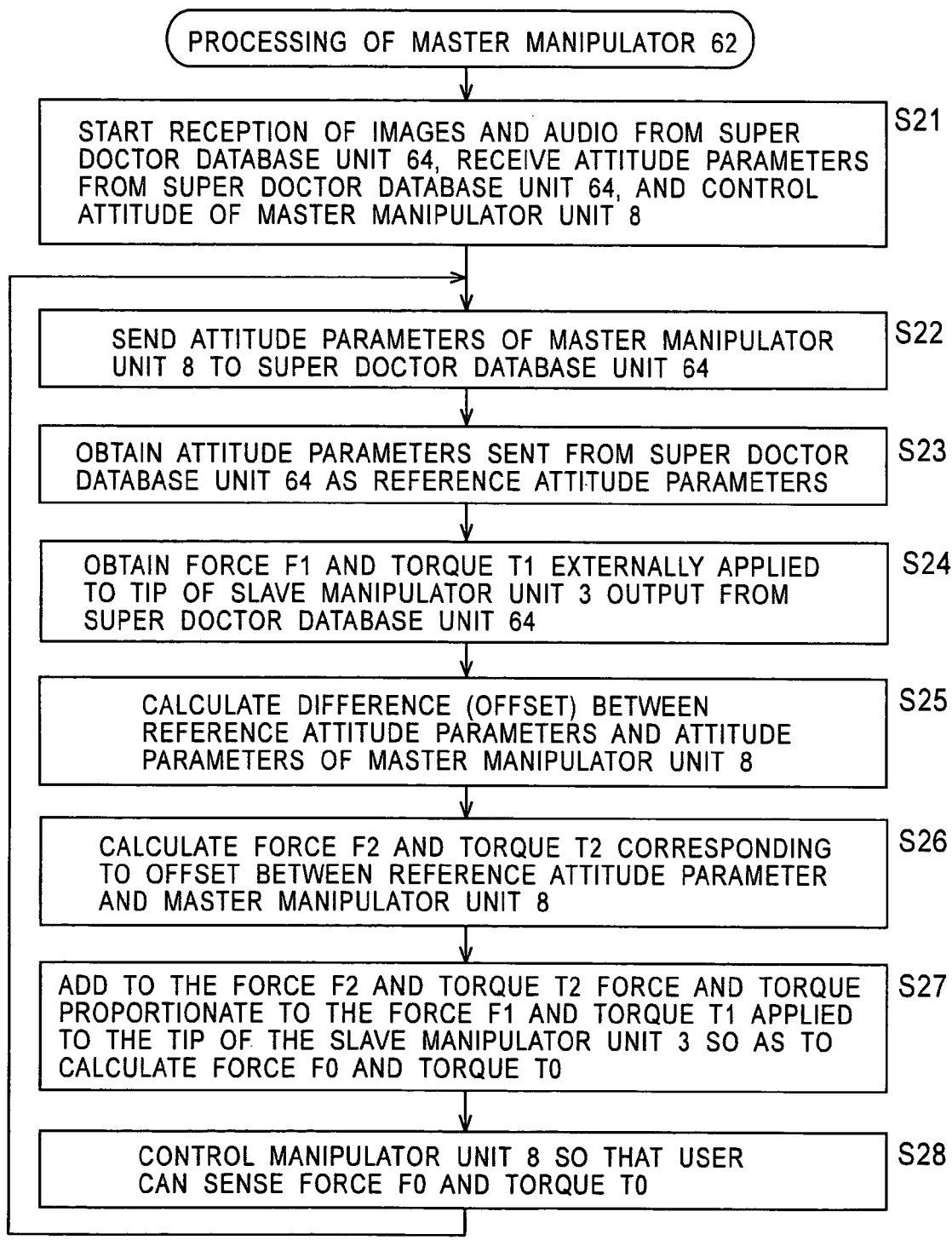
FIG. 11 is a flowchart describing the processing of the master manipulator 62.

The flow then proceeds to step S43, where the input/output control device 21 receives the attitude parameters of the operating unit 9 transmitted from each of the master manipulators $62_1$ through $62_K$ in step S22 of FIG. 11, and supplies these to the attitude parameter registration unit 22 and attitude parameter control unit 28, and the flow proceeds to step S44.

In step S44, the attitude parameter registration unit 22 recognizes the surgery contents which the users $U_1$ through $U_K$ are attempting, based on the attitude parameters of the respective master manipulators $62_1$ through $62_K$. Further, the attitude parameter registration unit 22 registers the attitude parameters corresponding to the surgery contents in the surgery information database 25, and the flow proceeds to step S45.

In step S45, the attitude parameter control unit 28 calculates the scattering of the attitude parameters of the operating unit 9 from each of the master manipulators $62_1$ through $62_K$, and determines whether or not the scattering is a predetermined threshold value or higher.

In step S45, in the event that determination is made that the scattering of the attitude parameters of the operating unit 9 from each of the master manipulators $62_1$ through $62_K$ do not reach or exceed the predetermined threshold value, i.e., in the event that the users $U_1$ through $U_K$ of each of the master manipulators $62_1$ through $62_K$ are each making similar operations, the flow proceeds to step S46, where the attitude parameter control unit 28 obtains a weighting addition value such as an averaged value for example, for the attitude parameters of each of the master manipulators $62_1$ through $62_K$, and the flow proceeds to step S47.

Now, weighting addition values for the multiple attitude parameters may involve calculating an average value wherein the weighting for each of the multiple attitude parameters are the same, or may be calculated with difference weighting values for each of the multiple attitude parameters. That is to say, the weighting of the attitude parameters may be weighted according to the degree of experience of the user $U_k$ operating the master manipulator $62_k$ regarding which attitude parameters have been transmitted, for example. Note that weighting based on experience or the like may be set by operating the operating panel 12 of the master manipulator panel 62 (FIG. 8), for example.

In step S47, the attitude parameter control unit 28 searches the surgery skill information database 27 with the search unit 29, so as to determine whether or not surgery skill information which would limit the surgery with the attitude parameters having the weighting addition values obtained in step S46 is registered in the surgery skill information database 27.

In step S47, in the event that determination is made that there is no surgery skill information registered in the surgery skill information database 27 which would limit the surgery with attitude parameters which are weighting addition values, the flow skips step S48 and proceeds to step S49, where the attitude parameter control unit 28 supplies the attitude parameters which are weighting addition values to the input/output control device 21, and the input/output control device 21 transmits the attitude parameters from the attitude parameter control unit 28 to the slave manipulator 61. Subsequently, the flow returns to step S42, and thereafter, the same processing is repeated.

Accordingly, in this case, the movement of the tip 4 of the slave manipulator 61 follows the averaged movement of the users $U_1$ through $U_K$ of the master manipulators $62_1$ through $62_K$.

Also, in step S47, in the event that judgment is made that surgery skill information for restricting the surgery with attitude parameters which are weighting addition values is registered to the surgery skill information database 27, that is, in the event that the contents of the surgery according to attitude parameters which are weighting addition values are not found in past cases, or in the event that acceptable surgery development was not obtained in the past, the flow proceeds to step S48, and the attitude parameter control unit 28 corrects the attitude parameters which are weighting addition values according to the surgery skill information for restricting the surgery by the attitude parameters thereof, so as to bring into the restricted range of the surgery skill information. The flow then proceeds to step S49, the attitude parameter control unit 28 transmits the corrected attitude parameters to the slave manipulator 61 via the input/output control device 21, the flow returns to step S42, and the same processing is repeated thereafter.

Accordingly, in this case, the movement of the tip 4 of the slave manipulator 61 follows the averaged movement of the users $U_1$ through $U_K$ of the master manipulators $62_1$ through $62_K$ which has been corrected based on the surgery skill information.

On the other hand, in the event that it is determined in step S45 that the scattering of the attitude parameters of the operating unit 9 from each of the master manipulators $62_1$ through $62_K$ is equal to or exceeds the predetermined threshold value, i.e., in the event that one or more of the users $U_1$ through $U_K$ of the master manipulators $62_1$ through $62_K$ make different operations different to an extent that the operations cannot be said to be the same as those of other users, the flow proceeds to step S50, where the attitude parameter control unit 28 detects the attitude parameters different from the other attitude parameters (the attitude parameters causing the increased scattering) (hereafter referred to as unique parameters) from the attitude parameters of each of the operating units 9, from each of the master manipulators $62_1$ through $62_K$.

Here, in order to simplify description, we will say that there is one attitude parameter which is a unique parameter.

In the event that a unique parameter is detected in step S50, the flow proceeds to step S51, where the attitude parameter control unit 28 controls the updating unit 26 so as to determine whether or not there has been a case of successful surgery with the surgery contents represented by the surgery information corresponding to the unique parameter stored in the surgery information database 25, by making reference to the surgery development information of the surgery development information database 23.

In step S51, in the event that determination is made that there has been no past case wherein surgery has been successful with the surgery contents represented by the surgery information corresponding to the unique parameter, the flow proceeds to step S52, and concluding that the unique parameter is caused due to an erroneous operation of the operating unit 9, the attitude parameter control unit 28 obtains a weighted addition value such as an average value for example, from the attitude parameters from the operating unit 9 from each of the master manipulators $62_1$ through $62_K$ but excluding the unique parameter, and the flow proceeds to step S47.

Subsequently, in steps S47 through S49, processing the same as described above is performed with regard to weighted addition values of the attitude parameters from the operating unit 9 from each of the master manipulators $62_1$ through $62_K$ excluding the unique parameters, and the flow returns to step S42.

Accordingly, in this case, the movement of the tip 4 of the slave manipulator 61 follows the averaged movement of the users $U_1$ through $U_K$ of the master manipulators $62_1$ through $62_K$ from which operations markedly different from other operations are removed (or wherein the averaged operations are corrected based on the surgery skill information).

On the other hand, in step S51, in the event that it is determined that there have been past cases wherein surgery following the surgery content represented by the surgery information corresponding to the unique parameter has been successful, the flow proceeds to step S53, where the attitude parameter control unit 28 updates the surgery skill information database 27 by controlling the update unit 26.

That is, in this case, the updating unit 26 generates optimal operating methods (procedures) for the operating unit 9 to carry out the surgery, or generates operating contents or the like to be restricted as operations of the operating unit 9 as surgery skill information, based on the surgery contents represented by the surgery information corresponding to the unique parameter, and supplies and stores this to the surgery skill information database 27, thereby updating the surgery skill information database 27.

The flow then proceeds to step S54, where the attitude parameter control unit 28 controls the input/output control device 21 so as to transmit the attitude parameter which is a unique parameter to the slave manipulator 61, following which the flow returns to step S42 and the same processing is repeated thereafter.

Accordingly, in this case, the movement of the tip 4 of the slave manipulator 61 follows operations markedly different from other operations of the users $U_1$ through $U_K$ of the master manipulators $62_1$ through $62_K$.

That is to say, in the event that one of the users $U_1$ through $U_K$ of the master manipulators $62_1$ through $62_K$ makes operations different from other users (here, different to an extent that the operations cannot be said to be the same operations), and moreover there is a precedent of the surgery succeeding with such an operation, the movement of the tip 4 of the slave manipulator 61 follows the operations of the one user which has performed operations different to those of the other users.

Consequently, in the event that one of the users $U_1$ through $U_K$ is a renowned surgeon with highly-experienced surgery skills, as compared with the other users, and in the event that the user which is the renowned surgeon makes operations different from those of the other uses based on the nearest surgery skills, the tip 4 of the slave manipulator 61 moves corresponding to the operations of the user which is the renowned surgeon.

Accordingly, with the SHARN surgery system shown in FIG. 3, the surgery skill information of the surgery skill information database 27 in the super doctor database unit 64 is continuously updated to a better one, by the attitude parameters based on the operations of each of the master manipulators $62_1$ through $62_K$. Further, with the super doctor database unit 64, attitude parameters to be provided to the slave manipulator 61 (reference attitude parameters) are generated from the attitude parameters based on the operations of each of the master manipulators $62_1$ through $62_K$, and the surgery skill information, and while surgery is performed on the patient at the slave manipulator 61 by the attitude of the top 4 being controlled following the reference attitude parameters, a load is placed on the users $U_1$ through $U_K$ operating the operating unit 9 so as to correct, as if it were, the offset between the operations of each of the master manipulators $62_1$ through $62_K$ and the reference attitude parameters.

As a result, surgery of the highest level is performed at the slave manipulator 61, based on skills from surgeons which are multiple users, and surgery skill information which is built upon past surgery and is continuously updated.

Also, at the master manipulator 62, the operations of the veterinarian which is a user are corrected so as to match the movement of the tip 4 in the actual surgery, thereby improving the surgery skills of the veterinarian which is a user in a short time.

That is to say, with the SHARN surgery system shown in FIG. 3, the surgery skill information of the super doctor database unit 64 is updated into a better one based on the operations of the master manipulators $62_1$ through $62_K$, and further, feedback, as if it were, can be received at the master manipulators $62_1$ through $62_K$, so that the operations of the users are corrected so as to match the surgery skill information.

Figure 13:
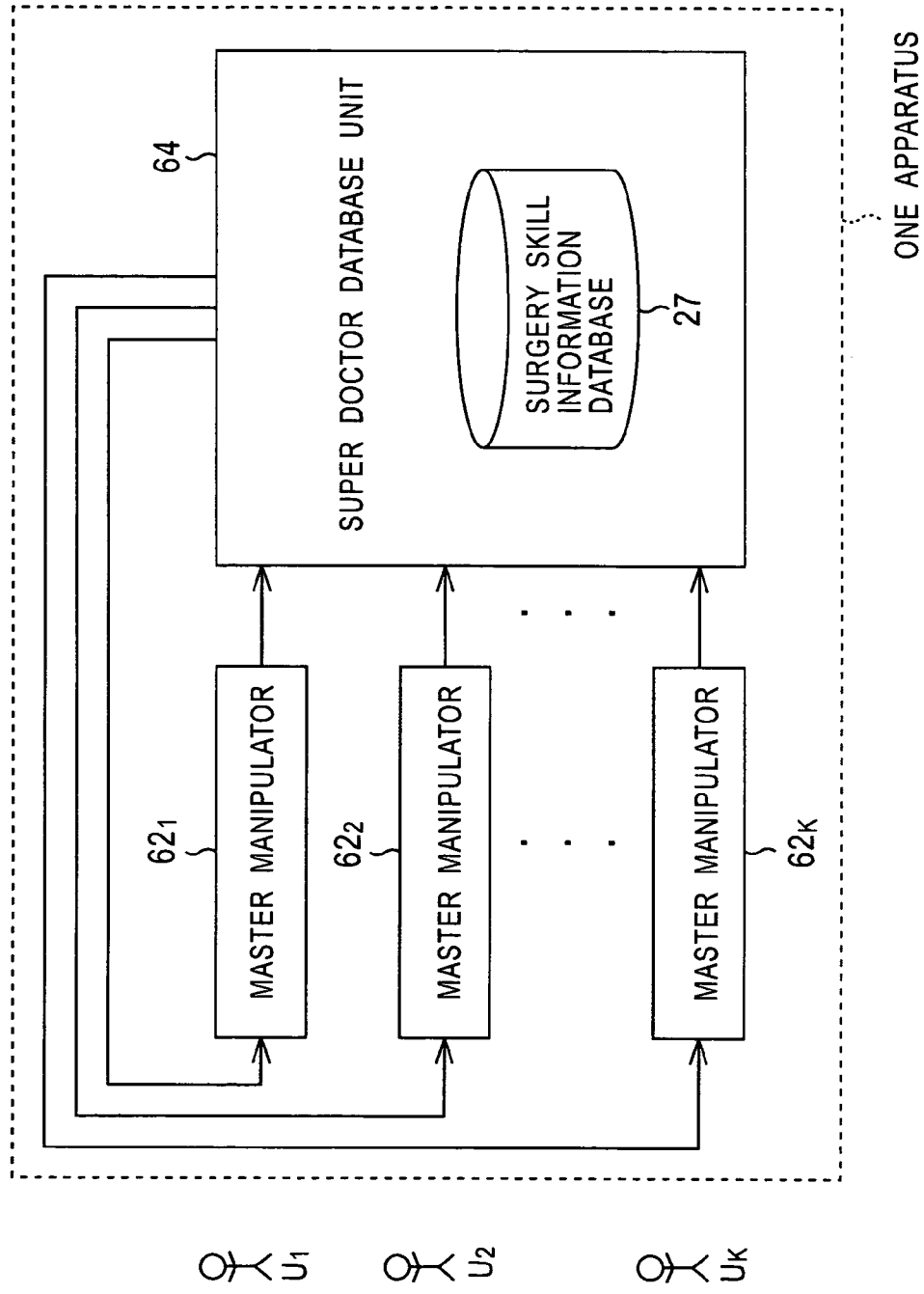
FIG. 13 is a diagram describing collaboration sharing in a SHARN surgery system.

Accordingly, at each of the master manipulators $62_1$ through $62_K$, high functionality consisting of the skills of the surgeons which are users being improved in a short time, which could not be realized in individual cases, can be said to be realized, due to the master manipulators $62_1$ through $62_K$, and the super doctor database unit 64, surrounded by the dotted line in FIG. 13, acting as if they were a single apparatus, with the surgery skill information of the super doctor database unit 64 being updated into a better one based on the operations of each of the master manipulators $62_1$ through $62_K$, whereby each of the master manipulators $62_1$ through $62_K$ share the processing of updating the surgery skill information into a better one through collaboration.

Conversely, in the event that the super doctor database unit 64 only stores the operation contents of each of the master manipulators $62_1$ through $62_K$, and gives feedback to the master manipulators $62_1$ through $62_K$, this is only simple sharing of the processing of the master manipulators $62_1$ through $62_K$ supplying the operations made by users to the super doctor database unit 64, and accordingly, this cannot realize the high functionality at each of the master manipulators $62_1$ through $62_K$ of the skills of the veterinarians as users being improved.

Figure 14:
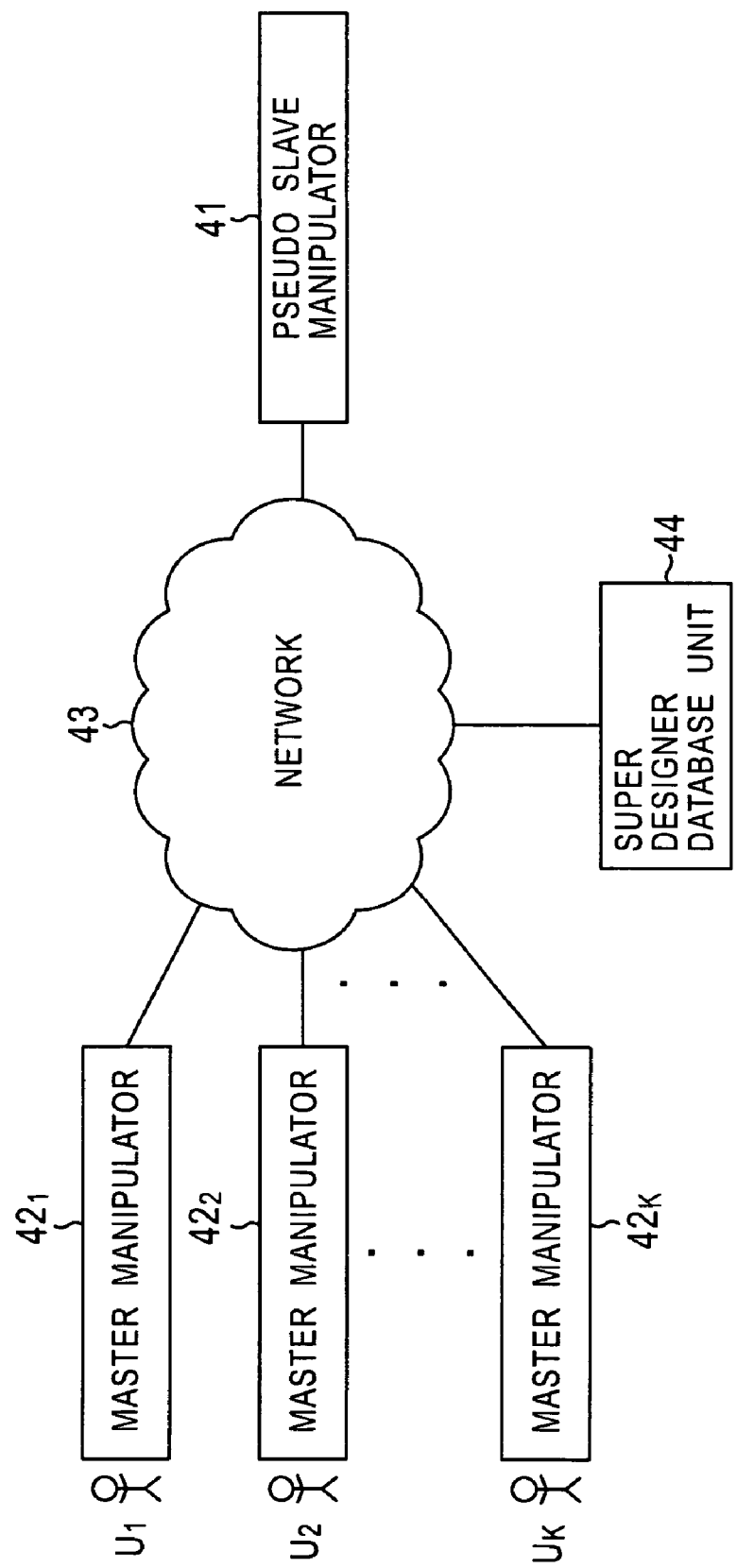
FIG. 14 is a block diagram illustrating a configuration example of an embodiment of a SHARN design system to which the SHARN system has been applied.

Next, FIG. 14 illustrates a configuration example of a SHARN design system serving as a design system to which the SHARN system has been applied.

This SHARN design system is a manipulator system for designing, and is made up of a pseudo slave manipulator 41, master manipulators $42_1$ through $42_K$, a network 43, and a super designer database unit 44.

The pseudo slave manipulator 41 acts based on signals supplied via the network 43, and performs certain designing on a subject of design. Here, a PDA (Personal Digital Assistance) for example, is the subject of design. Note however, that the subject of design is not restricted to PDAs.

The master manipulator $42_k$ acts according to the operations of the user $U_k$ and information supplied from the super designer database unit 44 through the network 43. Also, the master manipulator $42_k$ detects the state of action thereof, and transmits the detection results to the super designer database unit 44 via the network 43.

Note that while in the embodiment shown in FIG. 14, a K number of master manipulators $42_1$ through $42_K$ are provided, these will be described as master manipulator 42 hereafter unless there is a particular need to distinguish therebetween.

The network 43 enables communication between each of the pseudo slave manipulator 41, master manipulators $42_1$ through $42_K$, and the super designer database unit 44.

The super designer database unit 44 receives the state of actions of the master manipulator 42 supplied via the network 43, and generates information relating to design based on that state. Further, the super designer database unit 44 generates control signals based on the information relating to design and the state of the master manipulator 42, and supplies these to the pseudo slave manipulator 41 via the network 43, thereby controlling the pseudo slave manipulator 41.

Note that in the embodiments shown in FIG. 14, the master manipulator 42 corresponds to the operating unit 1003 shown in FIG. 1 (and FIG. 2), the actuator 1005, and the sensor 1007, the network 43 corresponds to the network 1001 shown in FIG. 1, and the super designer database unit 44 corresponds to the synthesizing/integrating unit 1002, driving control unit 1004, and signal processing unit 1006 shown in FIG. 1.

Also, with the embodiment shown in FIG. 14, the pseudo slave manipulator 41 is not a manipulator which performs actual work, but a manipulator which performs work in a virtual manner according to the master manipulator 42. Note however, that the pseudo slave manipulator 41 may be formed as a manipulator which performs actual work.

Figure 15:
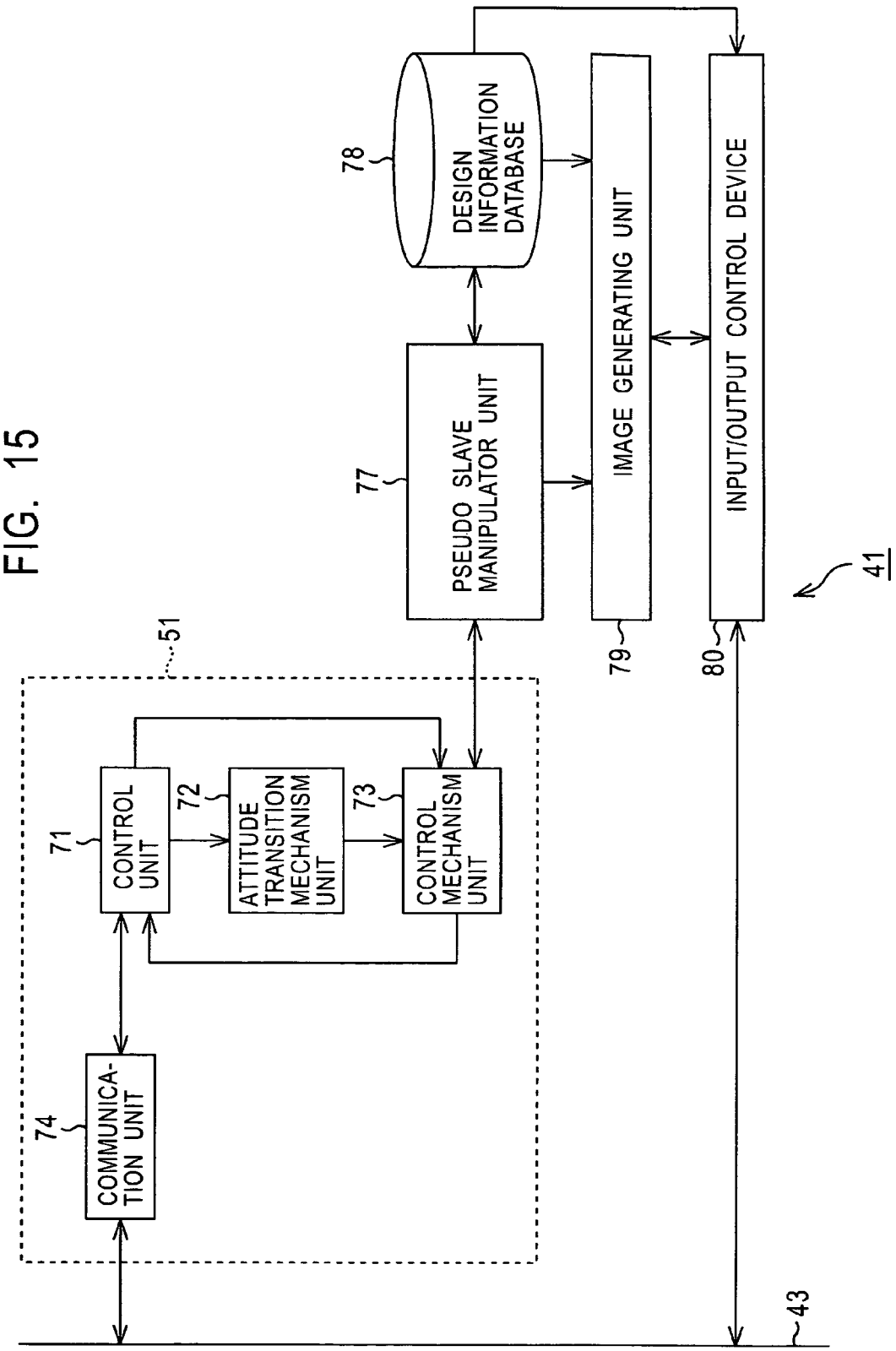
FIG. 15 is a block diagram illustrating an electrical configuration example of a pseudo slave manipulator 41.

Next, FIG. 15 illustrates an example of the electrical configuration of the pseudo slave manipulator 41 shown in FIG. 14. In the drawing, portions which corresponding to the case of the slave manipulator 61 shown in FIG. 7 are denoted with the same reference numerals, and description thereof will be omitted hereafter as appropriate.

The pseudo slave manipulator unit 77 has the same functions as those of the slave manipulator unit 3 shown in FIG. 7 in a pseudo manner, realized by a CPU executing a program, for example. The pseudo slave manipulator unit 77 performs various actions in a pseudo manner with regard to the object of design, following the control of the slave manipulator control unit 51.

That is to say, the pseudo slave manipulator unit 77 performs various types of processing with a virtual tip (equivalent to the tips 4L and 4R of the slave manipulator 61 in FIG. 4A), with regard to a virtual PDA determined from PDA design data stored in a design information database 78, following the control of the slave manipulator control unit 41.

Also, the pseudo slave manipulator unit 77 operates on a virtual PDA with the virtual tip in the same way as the slave manipulator unit 3 shown in FIG. 7, whereby signals corresponding to the force F1 and torque T1 which the virtual tip receives from the virtual PDA, i.e., signals corresponding to output of the sensor 75 of the slave manipulator unit 3 shown in FIG. 7, are calculated, and supplied to a control mechanism unit 73.

The design information database 78 stores design information which is data for determining external configuration of the virtual PDA. That is to say, the design information database 78 stores PDA design information which the users $U_1$ through $U_K$ of the master manipulators $42_1$ through $42_K$ have designed by operating the master manipulators $42_1$ through $42_K$.

An image generating unit 79 generates image data representing the state of the virtual tip and the like, based on internal data of the pseudo slave manipulator unit 77. Further, the image generating unit 79 generates image data of the virtual PDA from the design information stored in the design information database 78. The image generating unit 79 then synthesizes the image data of the virtual tip@ and the like, and the image data of the virtual PDA, thereby generating image data which would have been taken by the cameras $6_1$ through $6_2$ of the slave manipulator 61 in FIG. 7 had the pseudo slave manipulator unit 77 been an actual manipulator and the work done on an actual PDA. This image data is supplied from the image generating unit 79 to an input/output control device 80.

The input/output control device 80 is connected to the network 43, and the image data supplied from the image generating unit 79 is transmitted to the super designer database 44 via the network 43. Also, the input/output control device 80 transmits design information regarding the PDA designed by each of the users $U_1$ through $U_K$ that is stored in the design information database 78, to the super designer database 44 via the network 43.

Figure 16:
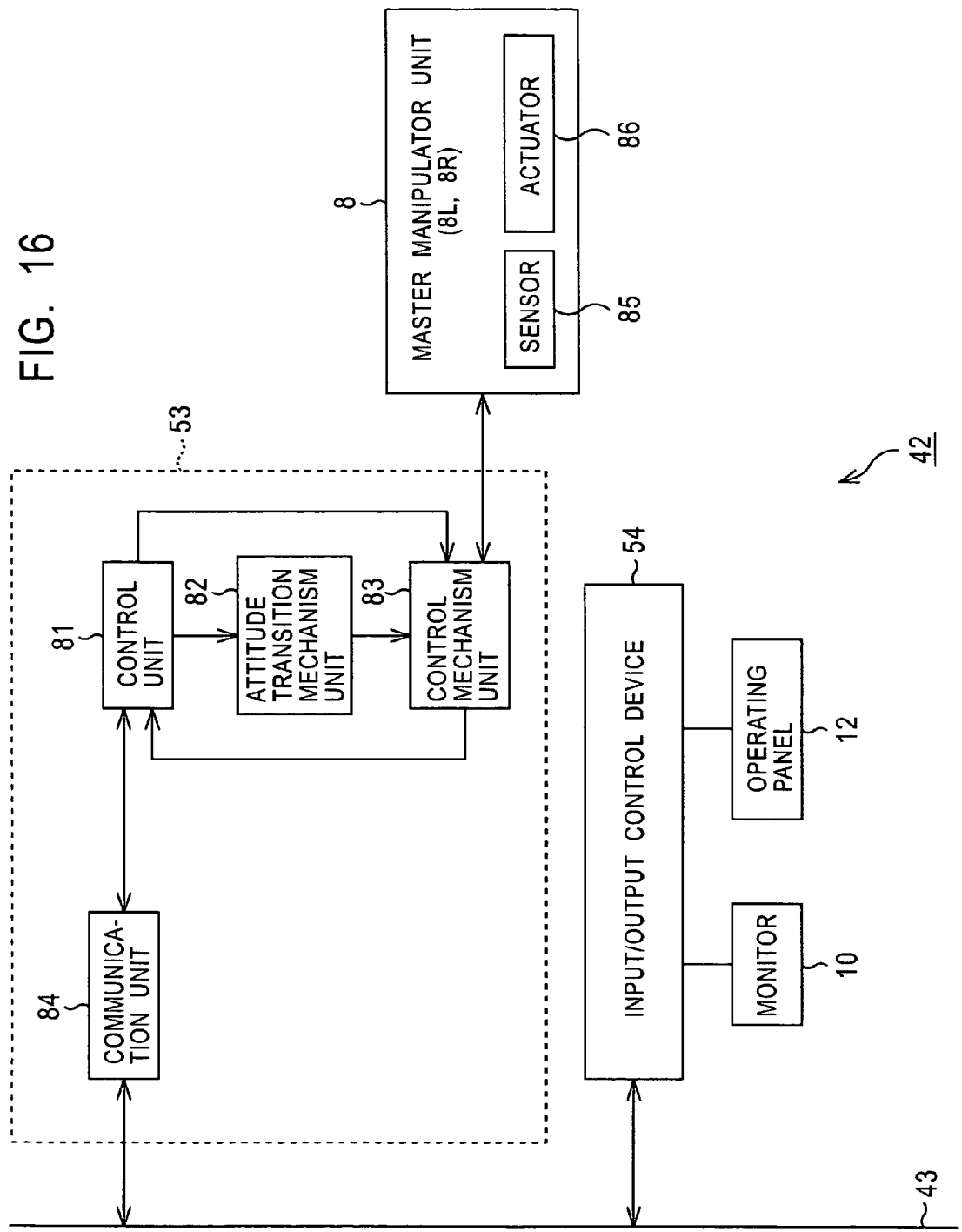
FIG. 16 is a block diagram illustrating an electrical configuration example of a master manipulator 42.

Next, FIG. 16 illustrates an example of the electrical configuration of the master manipulator 42 shown in FIG. 14. Note that the portions in the drawing which correspond to the master manipulator 62 shown in FIG. 8 are denoted with the same reference numerals, and description thereof will be omitted hereafter as appropriate. That is to say, the master manipulator 42 shown in FIG. 14 is configured in the same way as the master manipulator 62 shown in FIG. 8, except that no speaker 11 is provided. Accordingly, while not shown in the drawing, the external configuration of the master manipulator 42 is basically the same as the external configuration of the master manipulator 62 shown in FIG. 4B.

Figure 17:
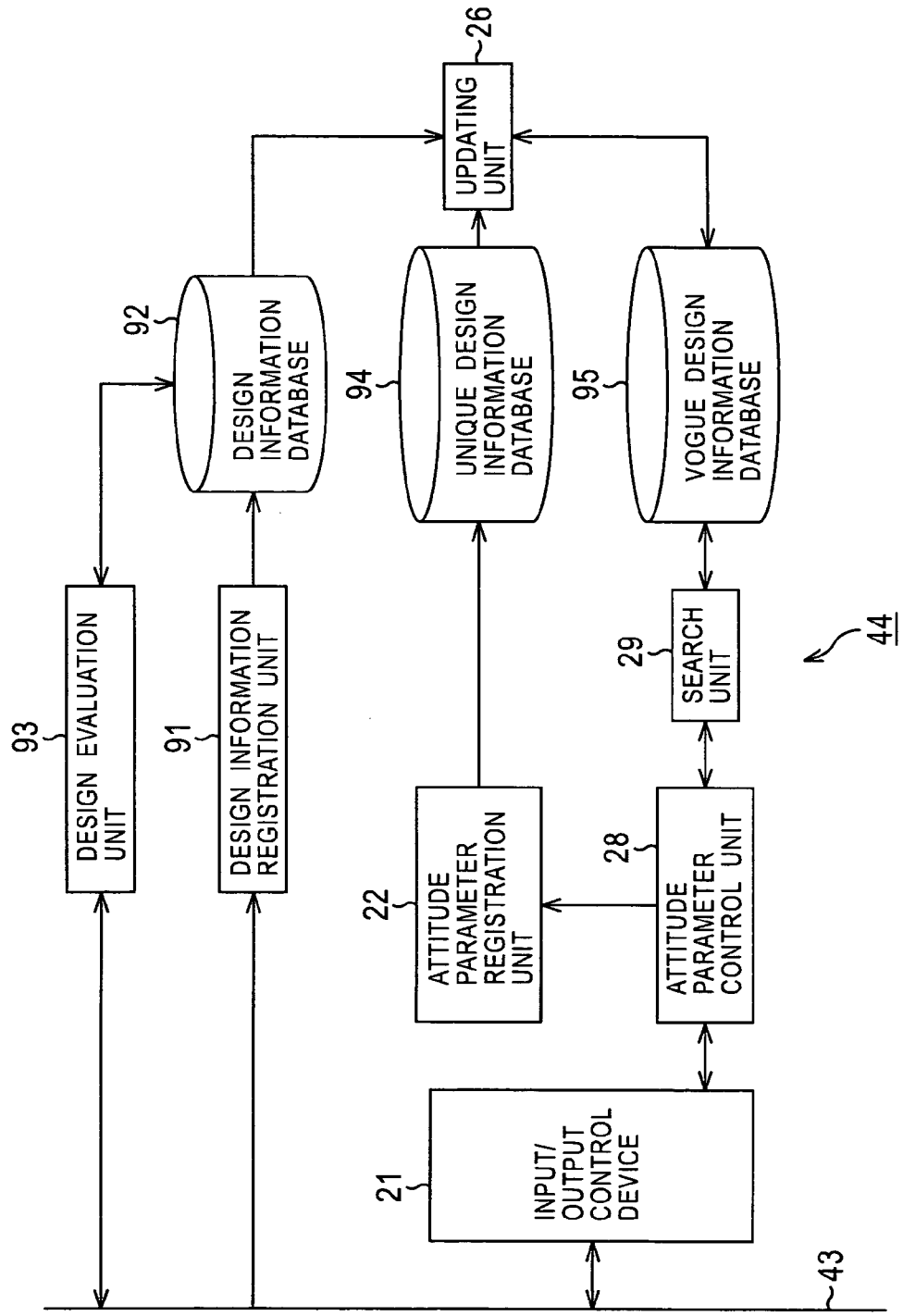
FIG. 17 is a block diagram illustrating an electrical configuration example of a super designer database unit 44.

Next, FIG. 17 illustrates a configuration example of the super designer database unit 44 shown in FIG. 14. Note that the portions in the drawing which correspond to the super doctor database unit 64 shown in FIG. 9 are denoted with the same reference numerals, and description thereof will be omitted hereafter as appropriate.

A design information registration unit 91 receives design information regarding the PDA designed by each of the users $U_1$ through $U_K$, which is stored in the design information database 78 and transmitted from the input/output control device 80 of the pseudo slave manipulator 41 in FIG. 15 over the network 43, supplies this to a design information database 92, and registers it. Note that transfer of the design information regarding the PDA which the user $U_K$ has designed, from the pseudo slave manipulator 41 to the super designer database unit 44, is performed by the user $U_K$, for example, making operations with the operating unit 12 of the master manipulator 42 so as to register his/her own PDA design.

The design information database 92 stores design information from the design information registration unit 91.

A design evaluating unit 93 evaluates the PDA design determined according to design information stored in the design information database 92.

That is to say, the design evaluating unit 93 discloses the external configuration of a PDA determined by the design information stored in the design information database 92, for example, on a web page on the Internet, for example, so as to hold a popularity vote, so that the PDA design is evaluated based on the results of the vote. Or, in the event that the PDA determined by the design information stored in the design information database 92 is already being sold as a product, for example, the PDA design is evaluated by collecting the number of PDA units sold via the network 43, based on the number of units sold.

A unique design information database 94 stores unique design information supplied from the attitude parameter registration unit 22, and the vogue design information database 95 stores the vogue design information supplied from the updating unit 26.

Now, vogue design information means design information stored in the design information database 92 with high evaluation made by the design evaluation unit 93, and unique design information means design information which is off, as if it were, from the vogue design information (hereafter referred to as unique design as appropriate).

Next, FIG. 18 illustrates PDA design information stored in the design information database 78 shown in FIG. 15, the design information database 92 shown in FIG. 17, the unique design information database 94, and the vogue design information database 95.

Figure 18A:
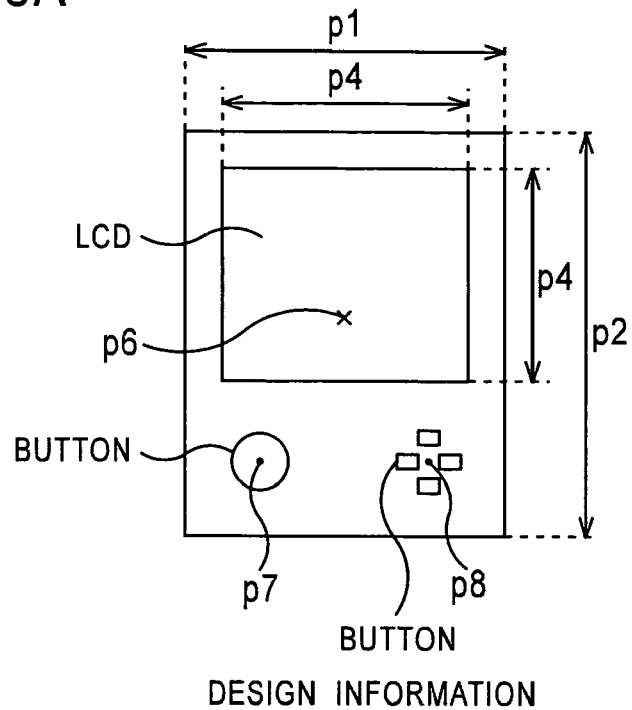
FIG. 18A is a diagram describing design information.

PDA design information which can be employed include, as shown in FIG. 18A, the width-wise length p1 of the PDA, the longitudinal length p2, the width-wise length p3 of the PDA which is the display unit of the PDA, the longitudinal length p4 thereof, the position p6 of the center of gravity of the PDA, the positions p7 and p8 of buttons provided on the PDA, and so forth.

Figure 18B:
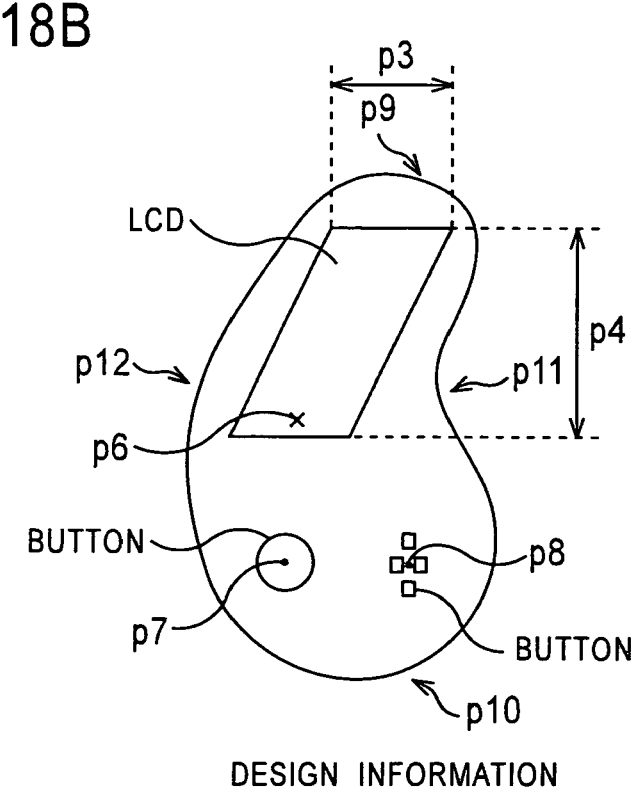
FIG. 18B is a diagram describing design information.

Also, as shown in FIG. 18B, in the event that the PDA has an arc-shaped roundness, the radii of the arcs, p9, p10, p11, p12, and so forth, and be employed as PDA design information.

Next, the processing of the pseudo slave manipulator 41 shown in FIG. 15 will be described with reference to the flowchart shown in FIG. 19.

In step S61, the input/output control device 80 starts transmission of image data generated at the image generating unit 79.

That is to say, Upon the user $U_k$ of the master manipulator $42_k$ (FIG. 16) so as to start designing, an operating signal corresponding to the operation thereof (hereafter referred to as start signal) is transmitted from the input/output control device 54 to the pseudo slave manipulator 41 and super designer database unit 44 via the network 43.

The start signal from the master manipulator $42_k$ is received by the input output control device 80 of the pseudo slave manipulator 41, and in this case, the input output control device 80 supplies this to the image generating unit 79 to generate the image data of the user $U_k$. Accordingly, the image generating unit 79 starts generating of image data of the user $U_k$, and the input output control device 80 starts transmission of image data generated for the user $U_k$ (hereafter referred to as user $U_k$ image data where appropriate). Note that the transmission of the image data is continued until the operating panel 12 of the maser manipulator $42_k$ (FIG. 16) is subsequently operated so as to stop the transmission thereof, for example.

Further, in step S61, the slave manipulator control device 51 transmits the attitude parameters at the virtual tip of the pseudo slave manipulator unit 77 to the super designer database unit 44.

That is to say, at the slave manipulator control device 51, the control mechanism unit 73 receives signals relating to the state of the virtual tip which the pseudo slave manipulator unit 77 outputs (hereafter referred to as state signals as appropriate), and supplies these to the control unit 71. The control unit 71 obtains the attitude parameters of the virtual tip of the pseudo slave manipulator unit 77 based on the state signals supplied from the control mechanism unit 73, and supplies these to the communication unit 74. The communication unit 74 transmits the attitude parameters from the control unit 71 to the super designer database unit 44 via the network 43.

Subsequently, as described later, attitude parameters are transmitted from the super designer database unit 44 through the network 43, so the communication unit 74 of the slave manipulator control device 51 awaits the transmission of the attitude parameters from the super doctor database unit 64, the flow proceeds to step S62, and the attitude parameters are received.

The attitude parameters are supplied from the communication unit 74 to the control unit 71, and the control unit 71 controls the pseudo slave manipulator unit 77 in step S63 so that the virtual tip of the pseudo slave manipulator unit 77 assumes an attitude corresponding to the attitude parameters.

Specifically, the control unit 71 of the slave manipulator control device 51 supplies the attitude parameters from the communication unit 74 to the attitude transition mechanism unit 72. The attitude transition mechanism unit 72 generates attitude transition information for causing the attitude of the virtual tip of the pseudo slave manipulator unit 77 to make transition from the current attitude to the attitude corresponding to the attitude parameters supplied from the control unit 71, and supplies these to the control mechanism unit 73.

The control mechanism unit 73 generates control signals according to the attitude transition information from the attitude transition mechanism unit 72, and transmits these to the pseudo slave manipulator unit 77. The pseudo slave manipulator unit 77 changes the attitude of the virtual tip according to the control signals from the control mechanism unit 73, so as to assume an attitude corresponding to the attitude parameters received by the communication unit 74.

The flow then proceeds to step S64, where the slave manipulator control device 51 transmits the force F1 and torque T1 externally applied (from the virtual PDA which is the object of design) due to the virtual tip of the pseudo slave manipulator unit 77 changing the attitude thereof in the control in step S63 to the super designer database unit 44 via the network 43, along with the attitude parameters of the virtual tip thereof.

That is to say, at the slave manipulator control device 51, the control mechanism unit 73 supplies state signals output from the pseudo slave manipulator unit 77 to the control unit 71, and the control unit 71 calculates the force F1 and torque T1 which the virtual tip has externally received, and the attitude parameters of the virtual tip, from the state signals. Further, the control unit 71 supplies the force F1 and torque T1, and the attitude parameters, to the communication unit 74, and the communication unit 74 transmits the force F1 and torque T1, and the attitude parameters, to the super designer database unit 44 via the network 43.

Subsequently, the flow returns to step S62, and the same processing is repeated hereafter.

Accordingly, at the pseudo slave manipulator 41, the PDA is subjected to being design by the attitude of the virtual tip of the pseudo slave manipulator unit 77 changing according to the attitude parameters transmitted from the super designer database unit 44.

Note that in step S64, an arrangement may be made wherein the force F1 and the torque T1 are calculated assuming that the PDA is formed of plastic foam or ABS (Acrylonitrile Butadiene Styrene) resin or the like used as material for models, for example.

Next, the processing of the master manipulator 42 shown in FIG. 16 will be described with reference to the flowchart shown in FIG. 20.

As described later, the super designer database unit 44 transmits image data transmitted from the pseudo slave manipulator 41 to the master manipulator 42 via the network 43, so in step S71, reception of the image data is started.

That is to say, in step S71, the input/output control device 54 receives image data transmitted from the super designer database unit 44 via the network 43, and supplies the image data to the monitor 10. Accordingly, the monitor 10 displays an image illustrating the way in which the pseudo slave manipulator unit 77 (FIG. 15) performs processing on the PDA.

Further, as describe later, the super designer database unit 44 transmits the attitude parameters of the virtual tip, transmitted from the pseudo slave manipulator 41, to the master manipulator 42 via the network 43, so in step S71, the master manipulator control device 53 receives the attitude parameters, and controls the attitude of the operating unit 9 of the master manipulator unit 8 based on the attitude parameters.

That is, at the master manipulator control device 53, the communication unit 84 receives the attitude parameters of the virtual tip of the pseudo slave manipulator unit 77 transmitted from the super designer database unit 44 via the network 43, and supplies these to the control unit 81. The control unit 81 receives the attitude parameters from the communication unit 84, and supplies these to the attitude transition mechanism unit 82. The attitude transition mechanism unit 82 generates attitude transition information for causing the attitude of the operating unit 9 of the master manipulator unit 8 to make transition from the current attitude to the attitude corresponding to the attitude parameters supplied from the control unit 81, and supplies this to the control mechanism unit 83. The control mechanism unit 83 generates control signals according to the attitude transition information from the attitude transition mechanism unit 82, and sends these to the master manipulator unit 82. The actuator 86 of the master manipulator unit 8 is driven according to these control signals, and accordingly, the operating unit 9 changes in attitude so as to assume the same attitude as the attitude of the virtual tip of the pseudo slave manipulator unit 77.

Subsequently, in step S72, the attitude parameters of the operating unit 9 of the master manipulator unit 8 are transmitted to the super designer database unit 44 via the network 43.

Specifically, at the master manipulator control device 53, the control mechanism unit 83 receives the output of the sensor 85 of the master manipulator unit 8, and supplies this to the control unit 81. The control unit 81 calculates the attitude parameters of the operating unit 9 of the master manipulator unit 8 from the output of the sensor 85, and supplies these to the communication unit 84. The communication unit 84 transmits the attitude parameters of the operating unit 9 from the control unit 81 to the super designer database unit 44 via the network 43.

Due to the processing in this step S72, the attitude parameters representing the attitude of the operating unit 9 of the master manipulator unit 8 changed owing to user operations are transmitted to the super designer database unit 44.

The flow then proceeds to step S73, where the communication unit 84 of the master manipulator control device 53 receives the attitude parameters of the virtual tip of the pseudo slave manipulator unit 77 transmitted from the super designer database unit 44 via the network 43, as reference attitude parameters, and then the flow proceeds to step S74. In step S74, the communication unit 84 of the master manipulator control device 53 receives the force F1 and the torque T1 which the virtual tip has externally received, transmitted from the super designer database unit 44 along with the attitude parameters of the virtual tip. The attitude parameters regarding the virtual tip, and the force F1 and torque T1, are supplied from the communication unit 84 to the control unit 81, and the flow proceeds from step S74 to S75.

In step S75, the control unit 81 calculates the difference between the attitude parameters of the operating unit 9 obtained in step S72 and the reference attitude parameters obtained in step S73, and the flow proceeds to step S76.

In step S76, the control unit 81 calculates the force F2 and torque T2 of a magnitude proportionate to the difference (offset) between the attitude parameters of the operating unit 9 and the reference attitude parameters calculated in step S75, but in a direction opposite to the direction of offset, and the flow proceeds to step S77.

In step S77, the control unit 81 adds force and torque proportionate to the force F1 and the torque T1 obtained in step S74, to each of the force F2 and torque T2 calculated in step S76, thereby calculating force F0 and torque T0 to be sensed by the user U operating the operating unit 9. That is to say, the control unit 81 calculates the force T0 and torque T0 according to the above-described Expression (1), for example.

Subsequently, in step S78, the master manipulator unit 8 is controlled such that the user $U_k$ operating the operating unit 9 of the master manipulator unit 8 senses the force F0 and torque T0 calculated in step S77.

That is to say, the control unit 81 supplies the reference attitude parameters obtained In step S73 and the force F0 and torque T0 obtained in step S76 to the attitude transition mechanism unit 82. The attitude transition mechanism unit 82 generates something which is attitude transition information for moving the attitude of the operating unit 9 of the master manipulator unit 8 so as to make transition from the current attitude to the attitude corresponding to the reference attitude parameters supplied from the control unit 81, further including information of acceleration (including angular acceleration as described above) whereby the user can be made to sense the force F0 and torque T0, and supplies this to the control mechanism unit 83. The control mechanism unit 83 generates control signals following the attitude transition information from the attitude transition mechanism unit 82, and sends this to the master manipulator unit 8. The actuator 86 of the master manipulator unit 8 is driven according to these control signals, and accordingly, the operating unit 9 changes the attitude thereof with a predetermined acceleration, and assumes the same attitude as the virtual tip of the pseudo slave manipulator unit 77 while causing the user U to sense the force F0 and torque T0.

Subsequently, the flow returns to step S72, and thereafter, the same processing is repeated.

As described above, the force F0 and torque T0 to be sensed by the user U are the added values of the force F2 and torque T2 in the opposite direction to the offset with a magnitude proportionate to the magnitude of the offset calculated in step S75, and the force and torque proportionate to the force F1 and torque T1 which the virtual tip of the pseudo slave manipulator unit 77 has received, thereby enabling the user U to be caused to be conscious of the offset between the attitude parameters of the operating unit 9 and the referenced attitude parameters, and the reactive force at the virtual tip of the pseudo slave manipulator unit 77.

Accordingly, in the event that the user $U_k$ operates the operating unit 9 of the master manipulator unit 8 so as to assume an attitude different from the attitude corresponding to the reference attitude parameters, the greater the difference in attitude is, a great reactive force is received, so the user can recognize in a sensory manner how far his/her operations are from the actual attitude of the virtual tip of the pseudo slave manipulator unit 77.

Figure 21:
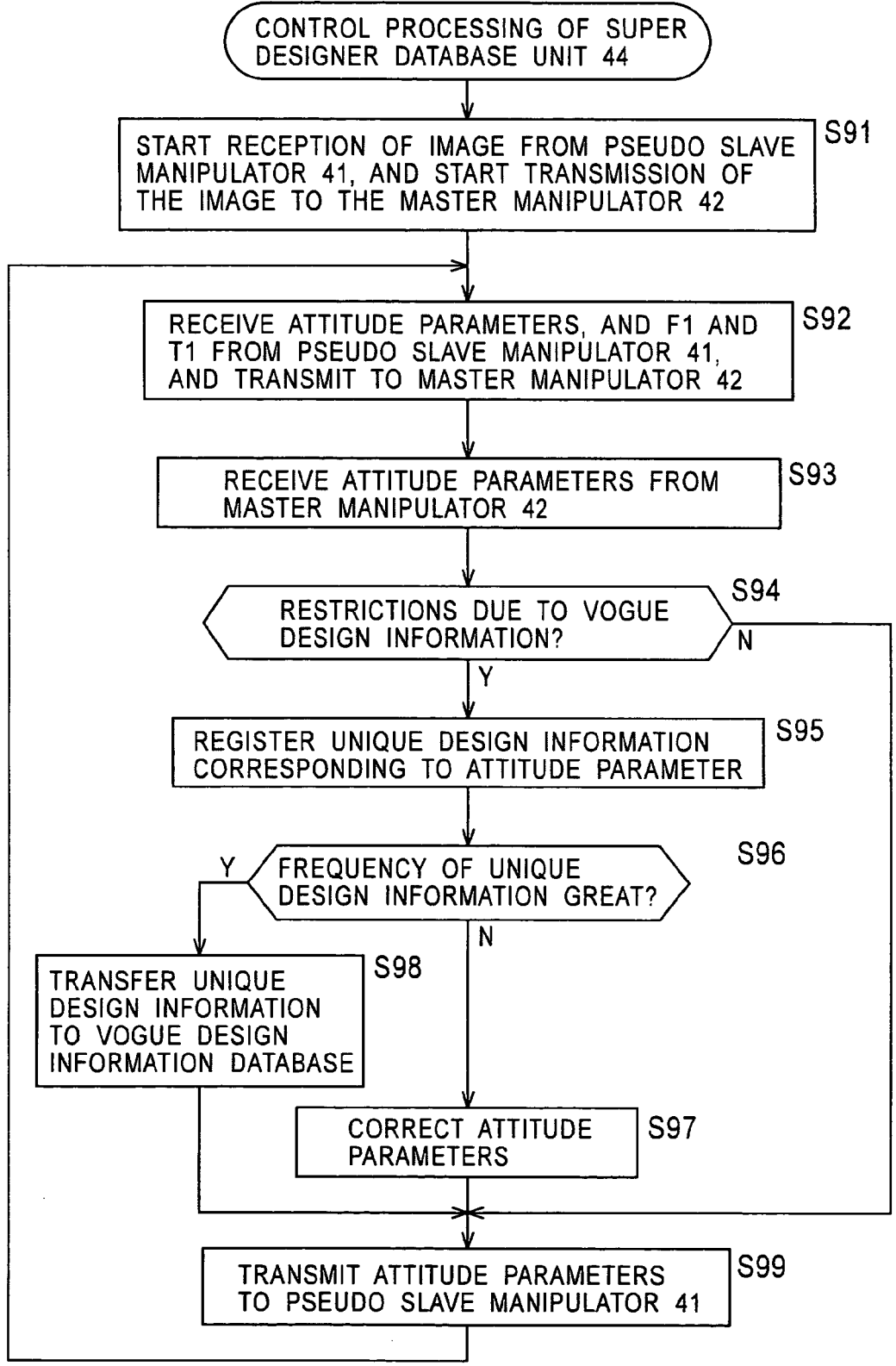
FIG. 21 is a flowchart describing processing of the super designer database unit 44 (control processing).

Next, the processing of the super designer database unit 44 shown in FIG. 17 will be described with reference to the flowchart in FIG. 21. Note that the super designer database unit 44 performs processing for each master manipulator $42_k$ transmitting start signals thereto, so as to control the master manipulator 42k and the pseudo slave manipulator 41, according to the flowchart shown in FIG. 17 (hereafter referred to as control processing, as appropriate). Accordingly, the above processing is performed for each master manipulator $42_k$ which has transmitted a start signal, at the pseudo slave manipulator 41 as well.

First, in step S91, the input/output control device 21 starts reception of image data from the pseudo slave manipulator 41 and transmission of that image data to the master manipulator $42_k$.

Figure 19:
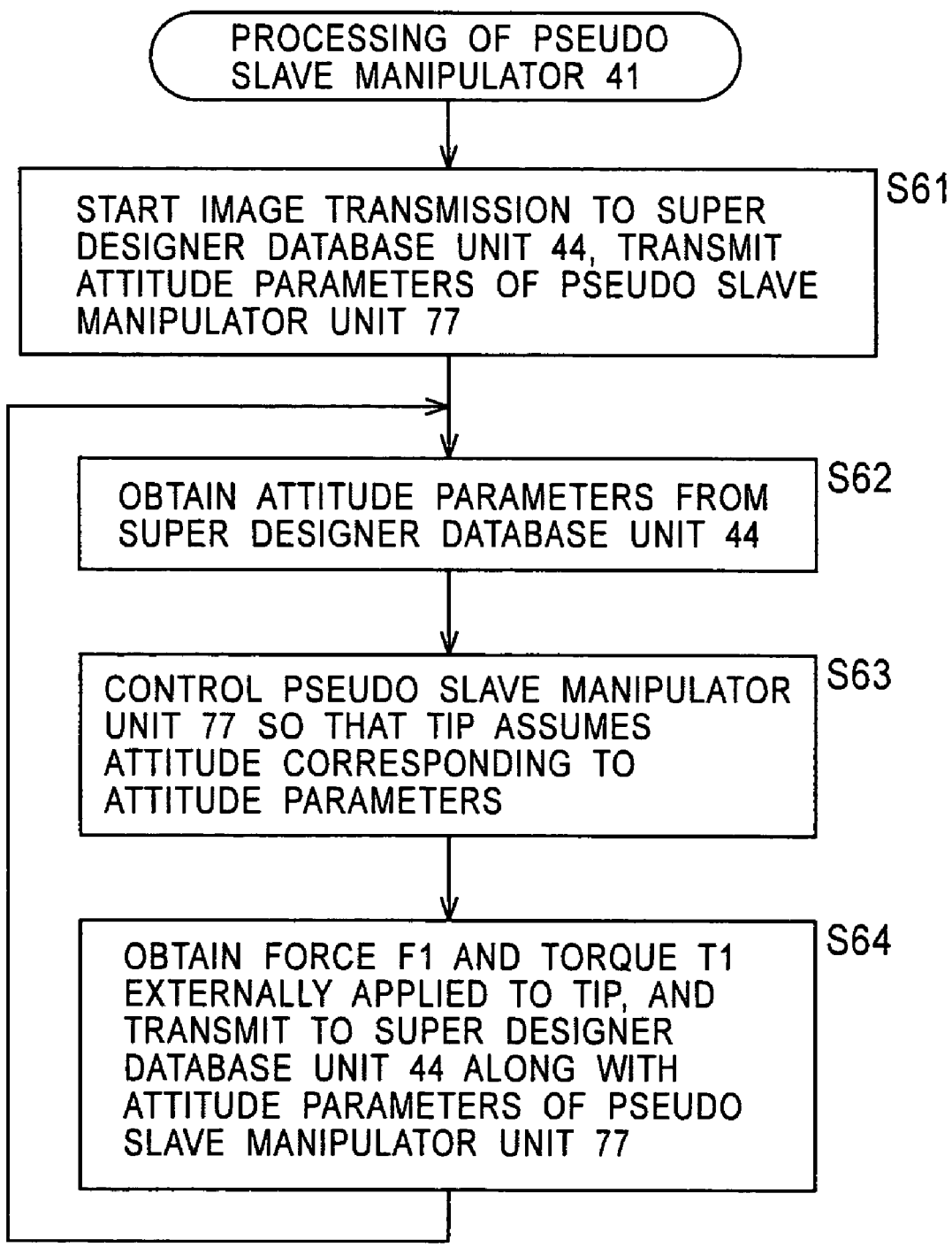
FIG. 19 is a flowchart describing processing of the pseudo slave manipulator 41.

That is, as described with FIG. 19, in step S61, the pseudo slave manipulator 41 (FIG. 15) starts transmission of image data to the super designer database unit 44, so the input/output control device 21 of the super designer database unit 44 starts reception of image data being transmitted thus from the pseudo slave manipulator 41 via the network 43.

Further, the input/output control device 21 starts transmission of the image data received from the pseudo slave manipulator 41 to the maser manipulator $42_k$. Now, at the master manipulator 42, reception of the image data transmitted from the input/output control device in this way is started in step S71 in FIG. 20 described above.

Also, in step S91, the input/output control device 21 receives the attitude parameters transmitted from the pseudo slave manipulator 41 in step S61 in FIG. 19 (the attitude parameters of the virtual tip of the pseudo slave manipulator 77), and transmits the attitude parameters as reference attitude parameters to the master manipulator $42_k$. Here, the reference attitude parameters are received by the master manipulator $42_k$ in step S71 in FIG. 20 above, whereby the operating unit 9 (the operating unit 9 of the maser manipulator unit 8) assumes an attitude corresponding to the reference attitude parameters, i.e., the same attitude as the virtual tip of the pseudo slave manipulator unit 77.

Subsequently, the flow proceeds to step S92, where the input/output control device 21 awaits and receives the attitude parameters regarding the virtual tip and the force F1 and torque T1 transmitted from the pseudo slave manipulator 41 (the attitude parameters of the virtual tip of the pseudo slave manipulator unit 77) in step S64 in FIG. 19, and transmits the attitude parameters as reference attitude parameters along with the force F1 and torque T1 to the master manipulator $42_k$. Now, at the master manipulator $42_k$, the attitude parameters regarding the virtual tip are received in step S73 in FIG. 20, and the force F1 and torque T1 regarding the virtual tip are received in step S74 in FIG. 20.

Figure 20:
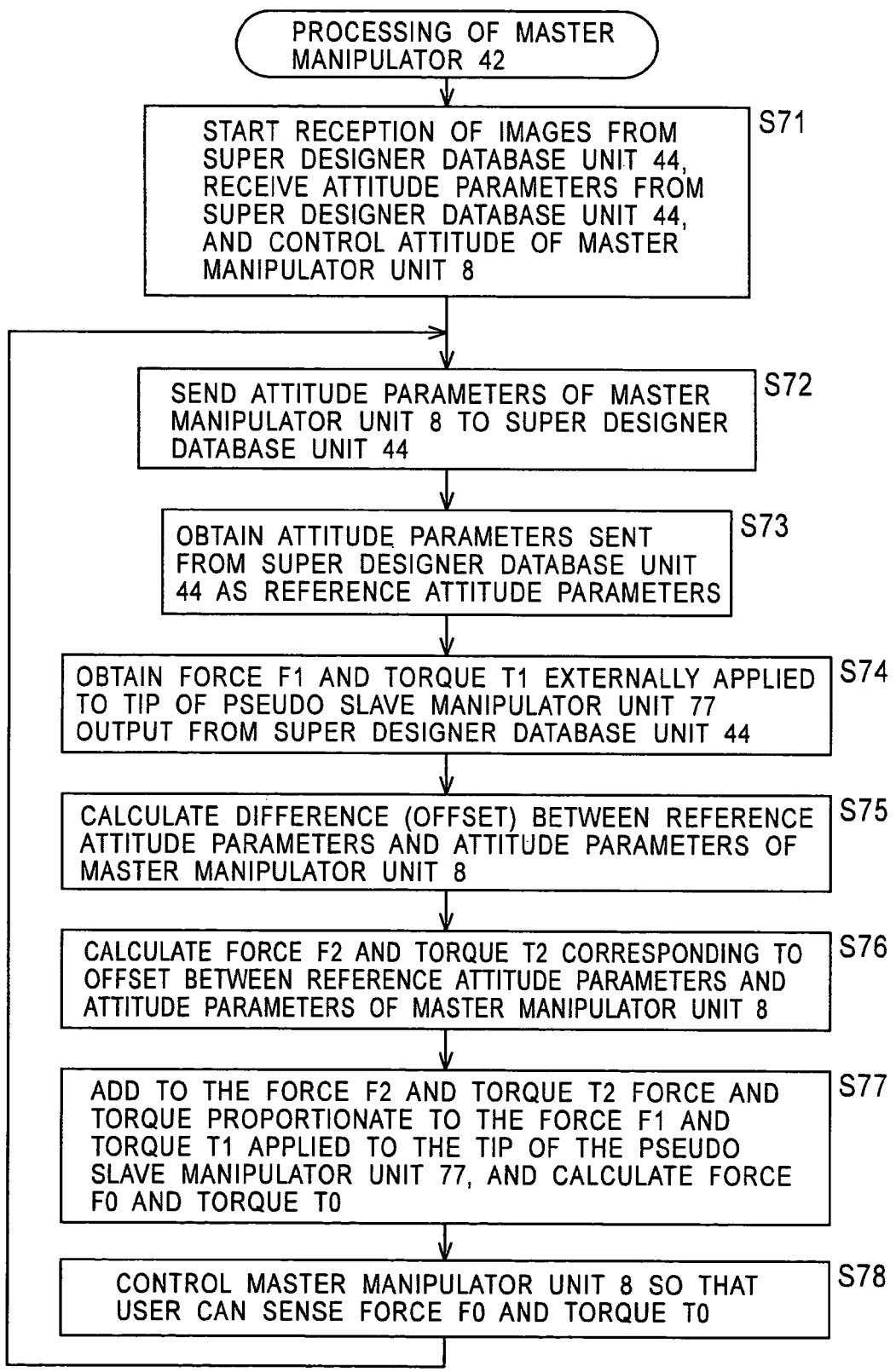
FIG. 20 is a flowchart describing processing of the master manipulator 42.

The flow then proceeds to step S93, where the input/output control device 21 receives the attitude parameters of the operating unit 9 transmitted from the master manipulator $42_k$ in step S72 of FIG. 20, and supplies these to the attitude parameter control unit 28 and the flow proceeds to step S94.

In step S94, the attitude parameter control unit 28 causes the search unit 29 to search the vogue design information database 95, to determine whether or not there is registered in the vogue design information database 95 any vogue design information which would restrict design according to attitude parameters received from the master manipulator $42_k$ in step S93.

In step S94, in the event that determination is made that there is no vogue design information which would restrict design according to attitude parameters received from the master manipulator $42_k$ registered in the vogue design information database 95, i.e., in the event that the design according to the attitude parameters do not markedly deviate (unique design) from that which is en vogue, represented by the vogue design information, the flow proceeds to step S99, where the attitude parameter control unit 28 supplies the attitude parameters from the master manipulator $42_k$ to the input/output control device 21, and the input/output control device 21 transmits the attitude parameters from the attitude parameter control unit 28 to the pseudo slave manipulator 41. Subsequently, the flow returns to step S92, and the same processing is repeated thereafter.

Accordingly, in this case, the movement of the virtual tip of the pseudo slave manipulator 41 follows the operations of the user $U_k$ of the master manipulator $42_k$.

On the other hand, in step S94, in the event that determination is made that there is vogue design information which would restrict design according to attitude parameters received from the master manipulator $42_k$ registered in the vogue design information database 95, i.e., in the event that the design according to the attitude parameters deviate (unique design) from that which is en vogue, represented by the vogue design information (in the event that the design is far-fetched in light of that which is currently en vogue), the flow proceeds to step S95, where the attitude parameter control unit 28 controls the attitude parameter registration unit 22 such that the design information from the master manipulator $42_k$ representing unique design is registered in the unique design information database 94, and the flow proceeds to step S96.

In step S96, the updating unit 26 determines whether the frequency of the unique design information registered in the unique design information database 94 in the immediately-prior step S95 (hereafter referred to as immediately-prior unique design information, as appropriate), is greater than a predetermined threshold value.

In step S96, in the event that the frequency of the immediately-prior unique design information is determined not to be greater than the predetermined threshold value, i.e., in the event that operations for carrying out unique design which the immediately-prior unique design information indicates, is not being performed very much by one or more users, the flow proceeds to step S97, and the attitude parameter control unit 28 corrects the attitude parameters from the master manipulator $42_k$ based on the vogue design information for restricting the design according to those attitude parameters, so as to come within the range of restriction under the vogue design information. The flow then proceeds to step S99, where the attitude parameter control unit 28 transmits the corrected attitude parameters to the pseudo slave manipulator 41 via the input/output control device 21, the flow returns to step S92, and subsequently, the same processing is repeated.

Accordingly, in this case, the movement of the virtual tip of the pseudo slave manipulator 41 follows a movement wherein the operations of the user $U_k$ of the master manipulator $42_k$ have been corrected based on the vogue design information, i.e., wherein the outlandish design (unique design) which the user was attempting is corrected so as to be not too far removed from the design en vogue.

On the other hand, in step S96, in the event that the frequency of the immediately-prior unique design information is determined to be great, i.e., in the event that operations for carrying out unique design which the immediately-prior unique design information indicates, is being performed frequently by one or more users, and as a result, the design currently en vogue is changing into a design which the immediately-prior unique design information indicates, the flow proceeds to step S98, where the updating unit 26 reads out the immediately-prior unique design information from the unique design information database 94, and transfers this to the vogue design information database 95 to be stored as vogue design information.

Subsequently, the flow proceeds to step S99, the attitude parameter control unit 28 transmits the attitude parameters from the master manipulator $42_k$ to the input/output control device 21, and the input/output control device 21 transmits the attitude parameters from the attitude parameter control unit 28 to the pseudo slave manipulator 41. Subsequently the flow returns to step S92, and the same processing is repeated thereafter.

Accordingly, in this case, the movement of the virtual tip of the pseudo slave manipulator 41 follows the operations of the user $U_k$ of the master manipulator $42_k$.

That is to say, in the event that the design according to the attitude parameters from the master manipulator $42_k$ is a unique design which deviates from the design that is en vogue as indicated by the vogue design information (in the event that the design is far-fetched in light of that which is currently en vogue), operations to perform such a unique design are corrected based on the vogue design information at first. However, even if the deign is a unique design at first, in the event that many operations are made to carry out that unique design, the unique design is assumed to have been accepted by many, such that the design currently en vogue has shifted to that unique design. Accordingly, in this case, the unique design is additionally stored in the vogue design information database 95 as vogue design information, and further, operations of users for carrying out this unique design are no loner restricted (corrected) by vogue design information.

Consequently, while the virtual tip of the pseudo slave manipulator 41 does not follow operations for carrying out the unique design, the virtual tip of the pseudo slave manipulator 41 comes follow operations for carrying out the unique design as the unique design comes to be accepted by many. That is, in the event that a PDA design such as shown in FIG. 18A is en vogue, attempts to operate the master manipulator 42 so as to carry out design of a PDA such as shown in FIG. 18B are restricted at first, but as many such operations are carried out, the restrictions not made any more, so that a PDA design such as shown in FIG. 18B becomes possible.

As described above, with the SHARN design system shown in FIG. 14, the vogue design information database 95 is updated based on designs performed by each of the users $U_1$ through $U_K$ operating the master manipulators $42_1$ through $42_K$ (additional storage of unique design information in the case described above), but this SHARN design system is further arranged such that the vogue design information database 95 is updated based on evaluations of other general users.

Figure 22:
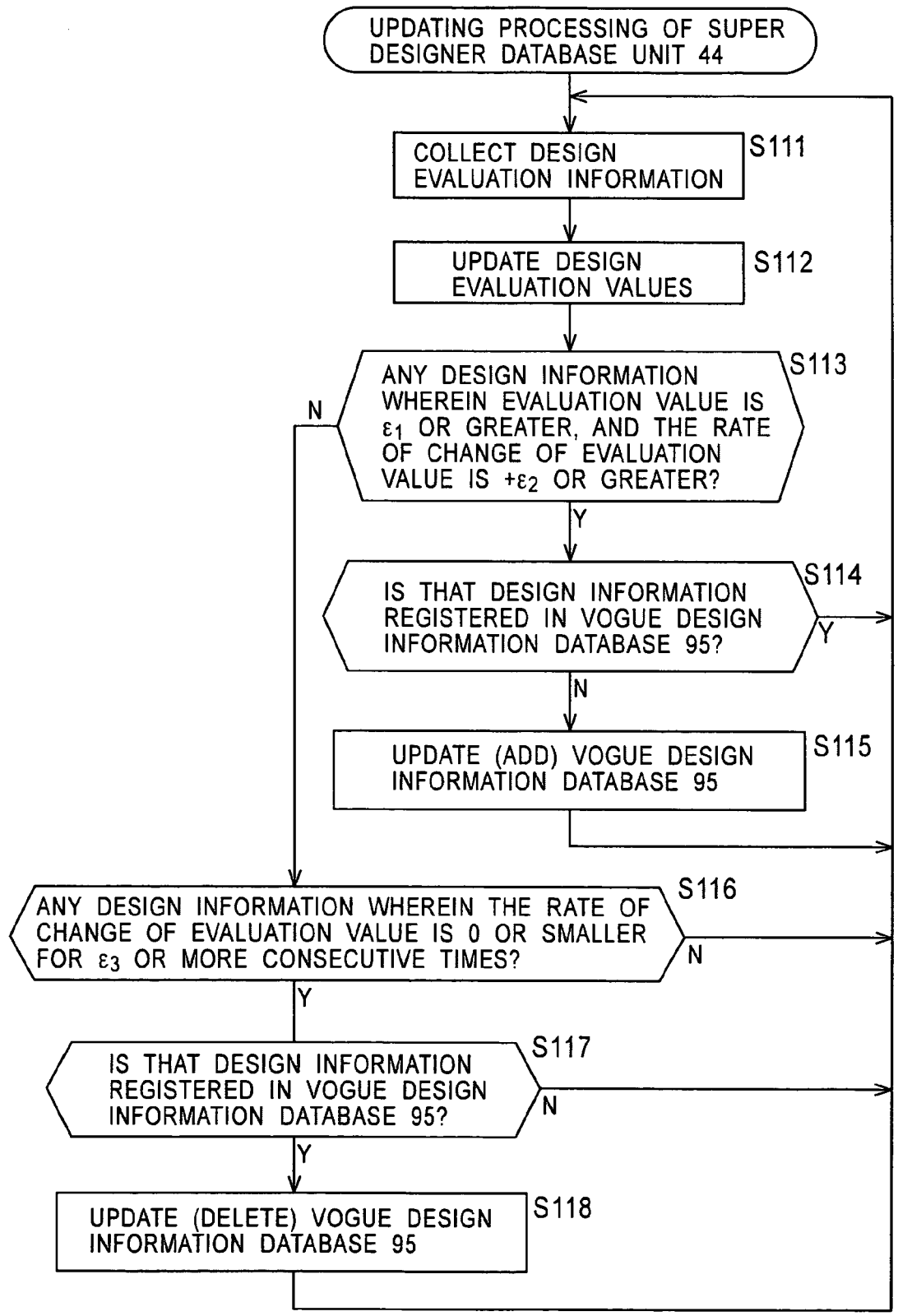
FIG. 22 is a flowchart describing processing of the super designer database unit 44 (updating processing).

Accordingly, the processing of updating the vogue design information database 95 based on evaluations of other general users will be descried, with reference to the flowchart in FIG. 22.

First, in step S111, the design evaluation unit 93 collects evaluation information evaluating designs according to the design information registered in the design information database 92 by the design information registration unit 91.

That is to say, the design evaluation unit 93 collects as evaluation information, via the network 43, the results of popularity votes cast by general users regarding design information, by means of a web page disclosing the design information stored in the design information database 92, for example. Also, the design evaluation unit 93 collects the number of PDA units determined according to design information stored in the design information database 92, as evaluation information, via the network 43.

The flow then proceeds to step S112, where the design evaluation unit 93 calculates the evaluation values for each design information stored in the design information database 92, based on the evaluation information collected in step S111, and updates the design information database 92 based on the evaluation values.

That is to say, the design information database 92 has design information stored in a manner correlated with the evaluation values obtained in the previous updating processing (hereafter referred to as previous evaluation value, as appropriate), and in step S112, the evaluation values (previous evaluation values) correlated to each design information, are updated according to evaluation values newly calculated with regard to the design information (hereafter referred to as current evaluation value, as appropriate).

Now, the evaluation value is a value of 0 or greater, and the greater the value is, the higher the evaluation level is.

Subsequently, the flow proceeds to step S113, where the updating unit 26 determines whether or not there is design information with an evaluation value of a predetermined threshold value $\epsilon_1$ or greater with a rate of change in the evaluation value equal to or greater than the threshold value+$\epsilon_2$ in the design information database 92.

In step S113, in the event that determination is made that there is design information with an evaluation value of a predetermined threshold value $\epsilon_1$ or greater with a rate of change in the evaluation value equal to or greater than the threshold value+$\epsilon_2$ in the design information database 92, that is to say, in the event that there is design information wherein the evaluation value itself is great, and further, the change in evaluation value (the increase) is also great (hereafter referred to as popular design information, as appropriate), the flow proceeds to step S114, and the updating unit 26 determines whether the popular design information is already registered as vogue design information in the vogue design information database 95.

In the event that determination is made in step S114 that the popular design information is already registered as vogue design information in the vogue design information database 95, the flow returns to step S111, and the same processing is repeated.

In the event that determination is made in step S114 that the popular design information has not yet been registered as vogue design information in the vogue design information database 95, the flow proceeds to step S115, where the updating unit 26 reads out the popular design information from the design information database 92, and supplies and additionally stores this to the vogue design information database 95 as vogue design information, thereby updating the vogue design information database 95, and the flow returns to step S111.

In step S113, in the event that determination is made that there is no design information with an evaluation value of a predetermined threshold value $\epsilon_1$ or greater with a rate of change in the evaluation value equal to or greater than the threshold value+$\epsilon_2$ in the design information database 92, that is to say, in the event that there is no popular design information, the flow proceeds to step S116, where the updating unit 26 determines whether there is design information registered in the design information database 92 of which the rate of change of the evaluation value has been 0 or less of a predetermined threshold value $\epsilon_3$ number of times or more.

In the event that determination is made in step S116 that there is design information of which the rate of change of the evaluation value has been 0 or less of a predetermined threshold value $\epsilon_3$ number of times or more, i.e., wherein the evaluation value does not change or only decreases (hereafter referred to as unpopular design information, as appropriate), the flow proceeds to step S117, where the updating unit 26 determines whether there is any unpopular design information registered in the vogue design information database 95 as vogue design information.

In the event that determination is made in step S117 that there is unpopular design information registered in the vogue design information database 95 as vogue design information, the flow proceeds to step S118, where the updating unit 26 deletes the unpopular design information as vogue design information from the vogue design information database 95, thereby updating the vogue design information database 95, and the flow returns to step S111.

Also, in the event that determination is made in step S117 that there is no unpopular design information registered in the vogue design information database 95 as vogue design information, step S118 is skipped, and the flow returns to step S111.

As described above, with the SHARN design system shown in FIG. 14, the vogue design information in the vogue design information database 95 in the super designer database unit 44 is updated into a better one (design matching what is currently en vogue) by attitude parameters based on operations of each of the master manipulators $42_1$ through $42_K$. Further, vogue design information of the vogue design information database 95 in the super designer database unit 44 is updated in to a better one by evaluations made by general users, as well. Further, with the super designer database unit 44, attitude parameters to be provided to the pseudo slave manipulator 41 (reference attitude parameters) are generated from the attitude parameters based on the operations of the master manipulator $42_k$ and the vogue design information, and at the pseudo slave manipulator 41, the attitude of the virtual tip is controlled according to the reference attitude parameters, whereby design is made, while on the other hand, a load is placed on the user $U_k$ operating the operating unit 9 so as to correct, as if it were, the offset between the operations of the user $U_k$ and the reference attitude parameters.

As a result, at the pseudo slave manipulator 41, design is executed in accordance with what is en vogue, in a manner of speaking, based on the design tastes of the user $U_k$, and vogue design information which is made up and is updated according to the design tastes of many other users.

Also, with the master manipulator $42_k$, the operations of the user $U_k$ is corrected based on the vogue design information, so improvement of design skills of the user $U_k$ can be realized in a short time.

Figure 23:
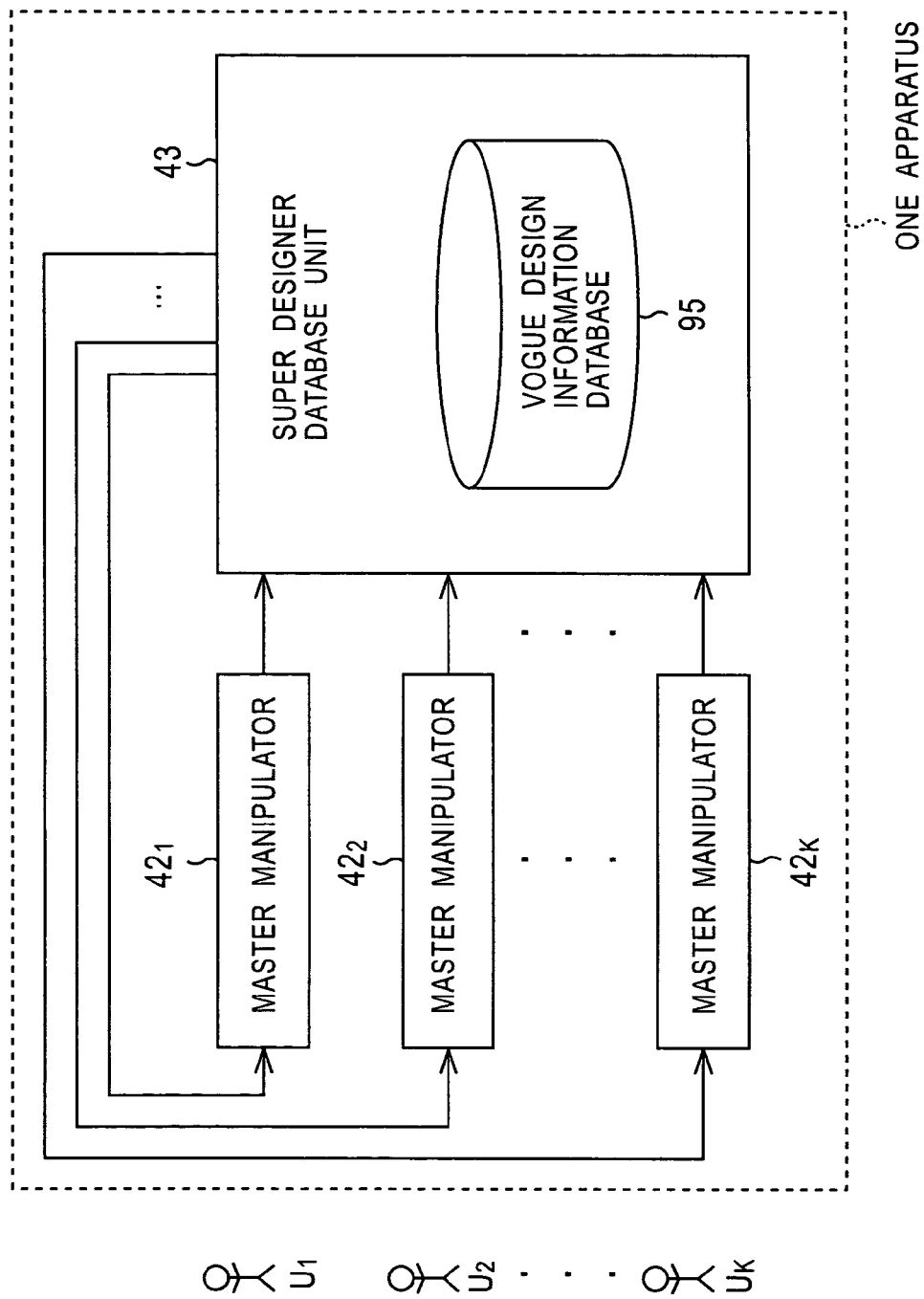
FIG. 23 is a diagram describing collaboration sharing in a SHARN design system.

Now, with the SHARN design system shown in FIG. 14, the vogue design information of the super designer database unit 44 is updated into a better one based on the operations of each of the master manipulators $42_1$ through $42_K$ as shown in FIG. 23, and further, at the master manipulators $42_1$ through $42_K$, feedback is received as if it were regarding vogue design information, so that the user operations are corrected so as to match vogue design information.

Accordingly, at each of the master manipulators $42_1$ through $42_K$, high functionality of improving the design skills of the users $U_1$ through $U_K$ can be realized, which could not be realized individually, due to the master manipulators $42_1$ through $42_K$, and the super designer database unit 44, surrounded by the dotted line in FIG. 23, acting as if they were a single apparatus, with the vogue design information of the super designer database unit 44 being updated into a better one based on the operations of each of the master manipulators $42_1$ through $42_K$, whereby each of the master manipulators $42_1$ through $42_K$ share the processing of updating the vogue design information into a better one through collaboration.

Conversely, in the event that the super designer database unit 44 only stores the operation contents of each of the master manipulators $42_1$ through $42_K$, and gives feedback to the master manipulators $42_1$ through $42_K$, this is only simple sharing of the processing of the master manipulators $42_1$ through $42_K$ supplying the operations made by users to the super designer database unit 44, and accordingly, this cannot realize the high functionality at each of the master manipulators $42_1$ through $42_K$ of the design skills of the users $U_1$ through $_K$ being improved at each of the master manipulators $42_1$ through $42_K$.

Figure 24:
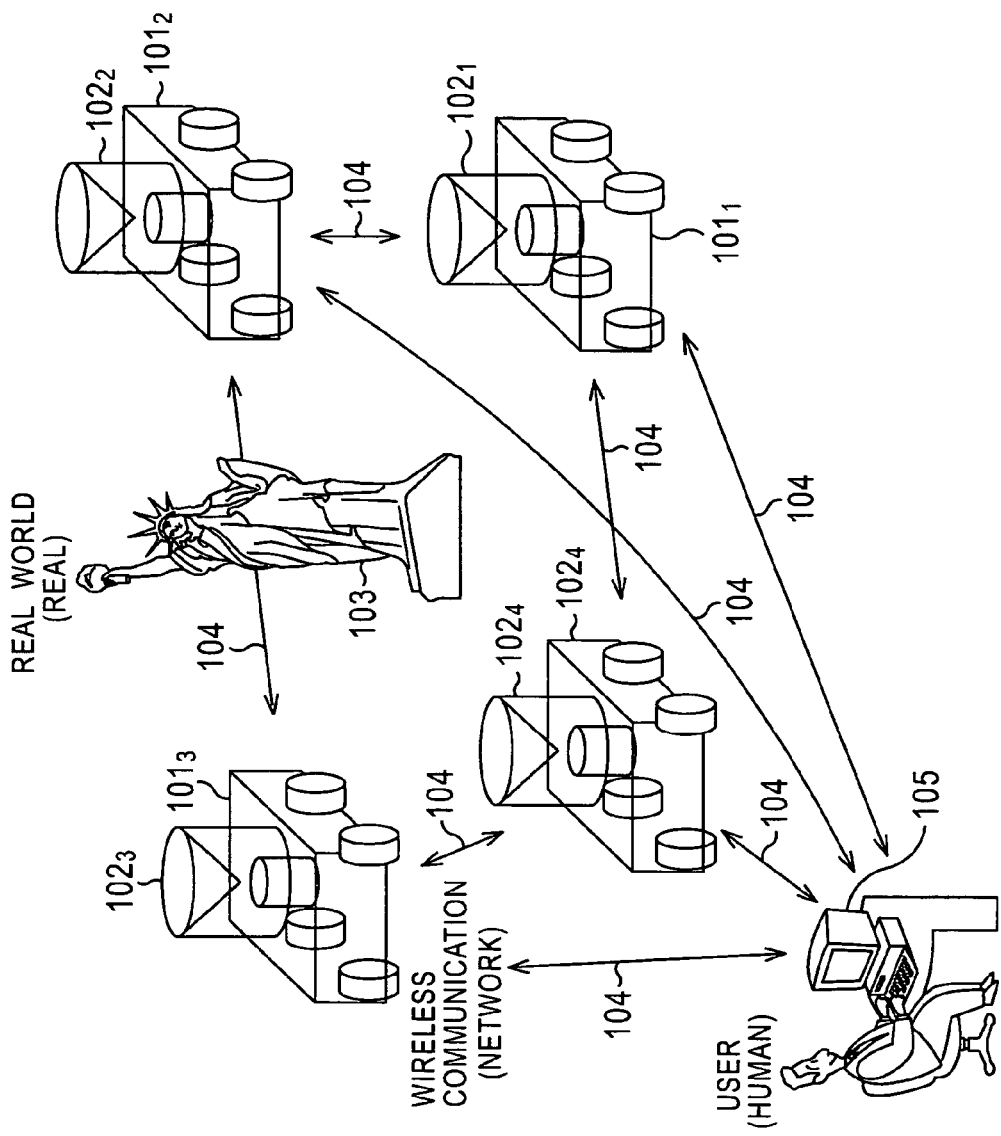
FIG. 24 is a block diagram illustrating a configuration example of an embodiment of a SHARN moving entity system to which the SHARN system has been applied.

Next, FIG. 24 illustrates a configuration example of a SHARN moving entity system serving as a moving entity system to which the SHARN system has been applied.

This SHARN moving entity system is configured of a great number of moving entities (e.g., automobiles or the like) $101_1, 101_2, \ldots$, all-directional cameras $102_k$ mounted on each moving entity $101_k$, and a network 104.

An automobile service as a moving body $101_k$ moves over roads or the like by acting in response to operations made by a user $U_k$ driving. An all-directional camera $102_k$ provided to the moving entity $101_k$ takes (detects) all-directional images centered on itself. Accordingly, an all-directional camera $102_k$ on a moving entity $101_k$ capable of direct-line sight of a subject 103 can take images including the subject 103 even without giving consideration to the direction in which the subject 103 exists. The network 104 is a network enabling wireless communication between arbitrary moving entities $101_k$ and $101_{k'}$.

Now, in the following, the all-directional image obtained by the all-directional camera $102_k$ centered on itself, will be referred to as all direction image, as appropriate.

The moving entity $101_k$ communicates with other moving entities $101_{k'}$ via the network 104. The moving entity $101_k$ receives image data taken with other moving entities $101_{k'}$ via the network 104, and processes that image data, thereby generating added-value added image data.

Now, with the embodiment shown in FIG. 24, the moving entity $101_k$ corresponds to the operating unit 1003, actuator 1005, synthesizing integrating unit 1002, driving control unit 1004, and signal processing unit 1006 in FIG. 1 (and FIG. 2), the all-directional cameral $102_k$ corresponds to the sensor 1007 in FIG. 1, and the network 104 corresponds to the network 1001 in FIG. 1.

Note that communication with a moving entity $101_{k'}$ is not restricted to only the moving entity $101_k$, and an information processing device 105 serving as a fixed station can also perform this. The information processing device 105 which is the fixed station can receive image data taken with other moving entities $101_{k'}$ via the network 104, and processes that image data, thereby generating added-value added image data, as with the moving entity $101_k$.

Next, the functions of the SHARN moving entity system shown in FIG. 24 will be briefly described with reference to FIG. 25.

With the SHARN moving entity system, as a first function, a moving entity $101_8$ for example, which is a desired moving entity, is specified by an unshown moving entity $101_k$, so as to obtain the all-directional image data taken by the all-directional camera $102_8$ at the location of the moving entity $101_8$, via the network 104.

Also, as a second function, the moving entity $101_k$ can specify a moving entity situated in a desired line-of view direction v with regard to a subject 103 (the moving entity $101_7$ in FIG. 25), and obtain the all-directional image data taken by the all-directional camera $102_7$ at the location of the moving entity $101_7$, via the network 104. In this case, the all-directional image data includes an image viewing the subject 103 from the predetermined line-of view direction v.

Further, as a third function, the moving entity $101_k$ can obtain all-directional image data including images viewing the subject 103 from a great number of viewpoint directions, taken by each of multiple moving entities (in FIG. 25, the moving entities $101_1, 101_2, 101_3, 101_4, 101_5$, and $101_6$, positioned on the dotted line circle surrounding the subject 103), via the network 104, and process the multiple sets of all-directional image data, thereby instantaneously obtain an image viewing the subject 103 while changing viewpoints (an image as if the subject 103 had been circled while being taken) (hereafter referred to as viewpoint-variable image as appropriate).

Now, the third function is realized by sharing processing for obtaining the viewpoint-variable image with the moving entities $101_1, 101_2, 101_3, 101_4, 101_5$, and $101_6$, through collaboration, a point which will be described in detail later.

Figure 26:
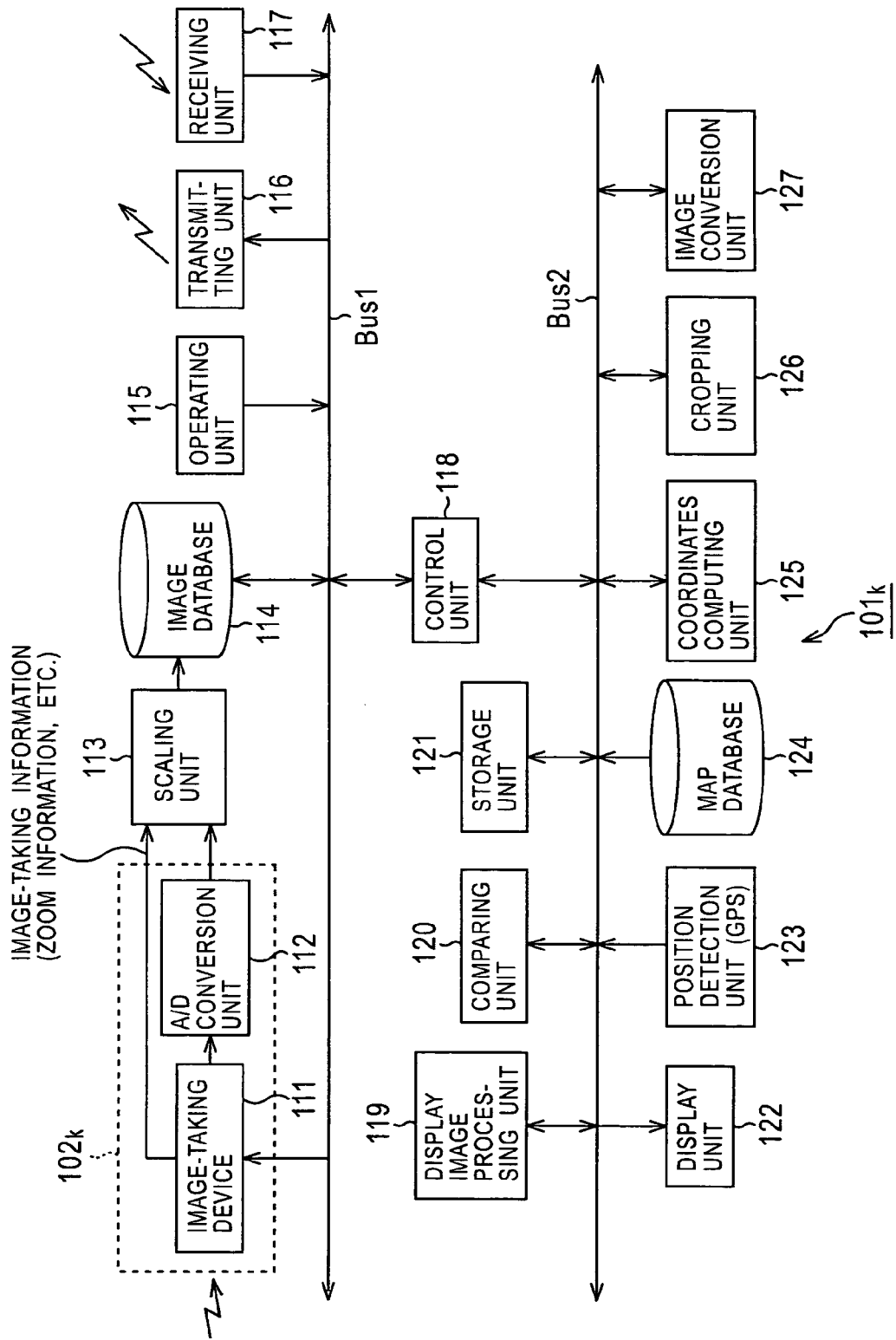
FIG. 26 is a block diagram illustrating an electrical configuration example of a moving entity $101_k$.

Next, FIG. 26 illustrates a configuration example of a moving entity $101_k$.

The all-directional camera $102_k$ is configured of an image-taking device 111 and an A/D (Analog/Digital) converting unit 112.

The image-taking device 111 takes (photographs) all-directional images according to control signals supplied from the control unit 118 via a bus Bus1, and supplies the analog image signals obtained as a result thereof to the A/D converting unit 112. Also, the image-taking device 111 supplies zoom information and the like relating to zooming at the time of taking the all-directional image, to a scaling unit 113.

The A/D converting unit 112 performs A/D conversion of the analog signals from the image-taking device 111, and accordingly obtains digital all-directional image data, which is supplied to the scaling unit 113.

The scaling unit 113 converts the scale of the all-directional image data supplied from the all-directional camera $112_k$ (the A/D converting unit 112 thereof) based on zoom information supplied from the same all-directional camera $112_k$ (the image-taking device 111 thereof).

That is, the scaling unit 113 converts the all-directional image data taken at an arbitrary zoom magnification at the all-directional camera $102_k$ into that taken with a predetermined zoom magnification.

The all-directional image data processed at the scaling unit 113 is supplied to an image database 114, and the image database 114 stores the all-directional image data from the scaling unit 113 so as to be correlated with necessary information. Also, the image database 114 also stores (registers) image data and the like supplied from the control unit 118 via the bus Bus1, as described later.

An operating unit 115 is operated for inputting predetermined information (e.g., the zoom magnification of the image-taking device 111 or the like) or commands, and the input is processed by being supplied to the control unit 118 via the bus Bus1. Also, the operating unit 115 also includes the steering wheel, accelerator, brake, etc., for controlling the moving body $101_k$ as well.

A transmission unit 116 transmits the information supplied via the bus Bus1 via the network 104 (FIG. 24). A receiving unit 117 receives the information transmitted via the network 104, and outputs onto the bus Bus1.

The control unit 118 is connected to busses Bus1 and Bus2, and controls the blocks connected to the busses Bus1 and Bus2.

A display image processing unit 119 performs processing of the image data supplied via the bus Bus2 so as to generate an image to be displayed on a display unit 112, and outputs to the bus bus2.

A comparing unit 120 makes reference to a storage unit 121 and position detecting unit 123 via the bus Bus2, compares the information stored in the storage unit 121 and information output from the position detecting unit 123, and notifies the control unit 118 of the comparison results via the bus Bus2.

The storage unit 121 temporarily stores the information and the like supplied from the control unit 118 via the bus Bus2.

A display unit 122 is configured of an LCD (Liquid crystal Display) or CRT (Cathode Ray Tube) or the like for example, and displays images according to image data supplied via the bus Bus2.

The position detecting unit 123 is configured of a GPS (Global Positioning System) or the like for example, and detects the current location of the moving entity $101_1$, and outputs to the bus Bus2.

A map database 124 stores map data which is electronic map data, and is referred to by other blocks via the bus Bus2.

A coordinates computing unit 125 computes predetermined coordinates and so forth according to control signals supplied from the control unit 118 via the bus Bus2.

A cropping unit 126 crops out a predetermined region from image data supplied via the bus Bus2 under the control of the control unit 118, and outputs onto the bus Bus2.

An image conversion unit 127 converts the image data supplied via the bus Bus2 under control of the control unit 118 into image data from which later-described distortion has been removed, and outputs onto the bus bus2.

Figure 27:
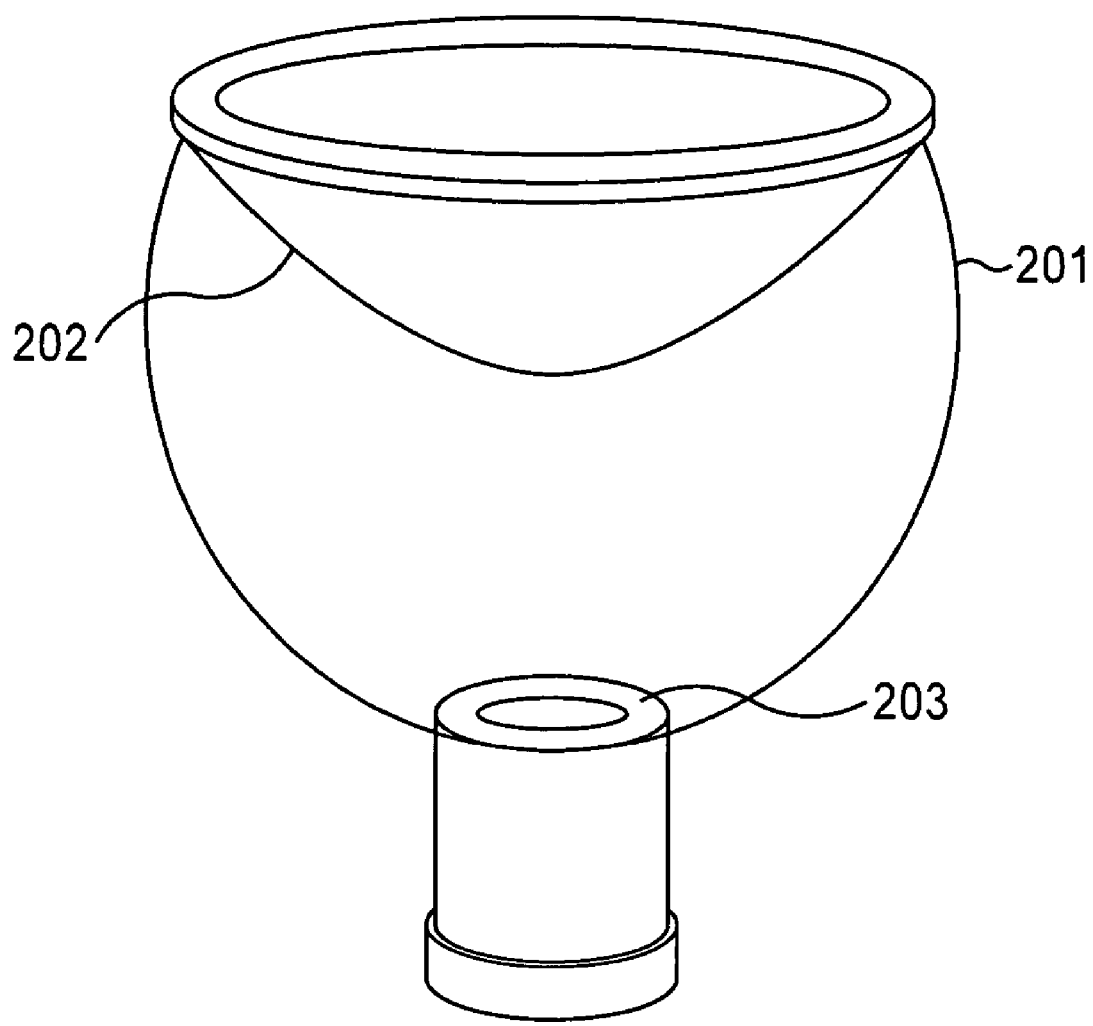
FIG. 27 is a perspective view illustrating a configuration example of an image-taking device 111.

Next, FIG. 27 illustrates a configuration example of the image-taking device 111 shown in FIG. 26.

The image-taking device 111 has a configuration wherein a condensing unit 202 is supported by a supporting unit 201 disposed above an image-taking unit 203, so as to be able to take images in 360° directions around the condensing unit 202.

The supporting member 201 is formed of a transparent material with low reflectivity such as glass or the like, and is a spherical face with the later-described focal point of the condensing unit 202 as the center thereof such that the incident light is orthogonal to the glass face, in order to minimize refraction of light at the glass face.

The condensing unit 202 has a hyperboloidal form, which reflects the surrounding light cast in through the supporting member 201 in the direction of the image-taking unit 203.

The image-taking unit 203 is configured of an electro-optical converting device such as a CCD or the like, for example, and converts light cast therein into image signals as electric signals. The image signals obtained at the image-taking unit 203 are supplied to the A/D conversion unit 112 shown in FIG. 26 as the output of the image-taking device 111.

Now, the configuration of condensation principle of the image-taking device 111 making up the all-directional camera $102_k$ is disclosed in, for example, "Development of All-Directional Visual Sensor for Moving Robot", Automation Technology Vol. 29, No. 6 (1997) (hereafter referred to as Document 1 as appropriate), so the description made here will be brief.

Figure 28:
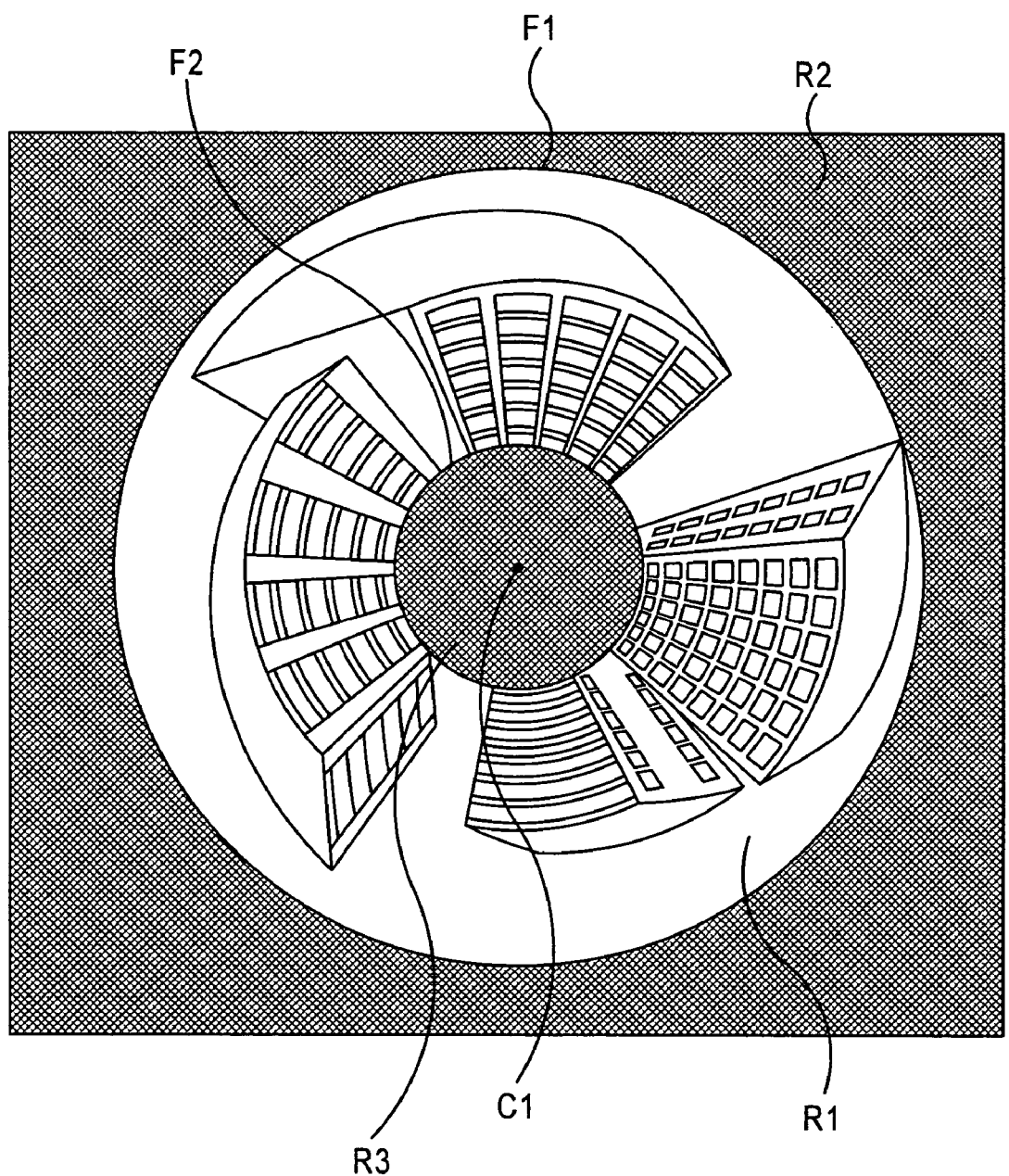
FIG. 28 is a diagram illustrating all-directional image data.

FIG. 28 illustrates an example of all-directional image data taken by the image-taking device 111 shown in FIG. 27.

The all-directional image data is sectioned by the perimeters F1 and F2 of two circles centered on a center point C1. Note that in FIG. 28, the perimeter F1 has a greater radius than the perimeter F2.

That is to say, the all-directional image data is configured of a region (inner region) R3 between a region R1 which is within the larger perimeter F1 and outside the smaller perimeter F2, and a region R2 outside the larger perimeter F1.

Of the three regions R1 through R3, the image data corresponding to the surrounding light reflected at the condensing unit 202 is taken in the region R1, and the portion outside of the condensing unit 202 is taken in the region R2. The image-taking unit 203 itself is taken in the region R3.

Further, with the embodiment shown in FIG. 28, multiple buildings have been taken in the region R1, with the tops of the buildings toward the direction closer to the perimeter F1 and the bottoms of the buildings toward the direction closer to the perimeter F2.

Next, the hyperboloid making up the condensing unit 202 shown in FIG. 27 will be described with reference to FIG. 29.

The condensing unit 202 is configured of part of a hyperboloid, and is formed by forming a mirror face on a convex face of the convex tip of a hyperboloid obtained by cutting a hyperboloid along a plane perpendicular to the axis of the hyperboloid.

Figure 29:
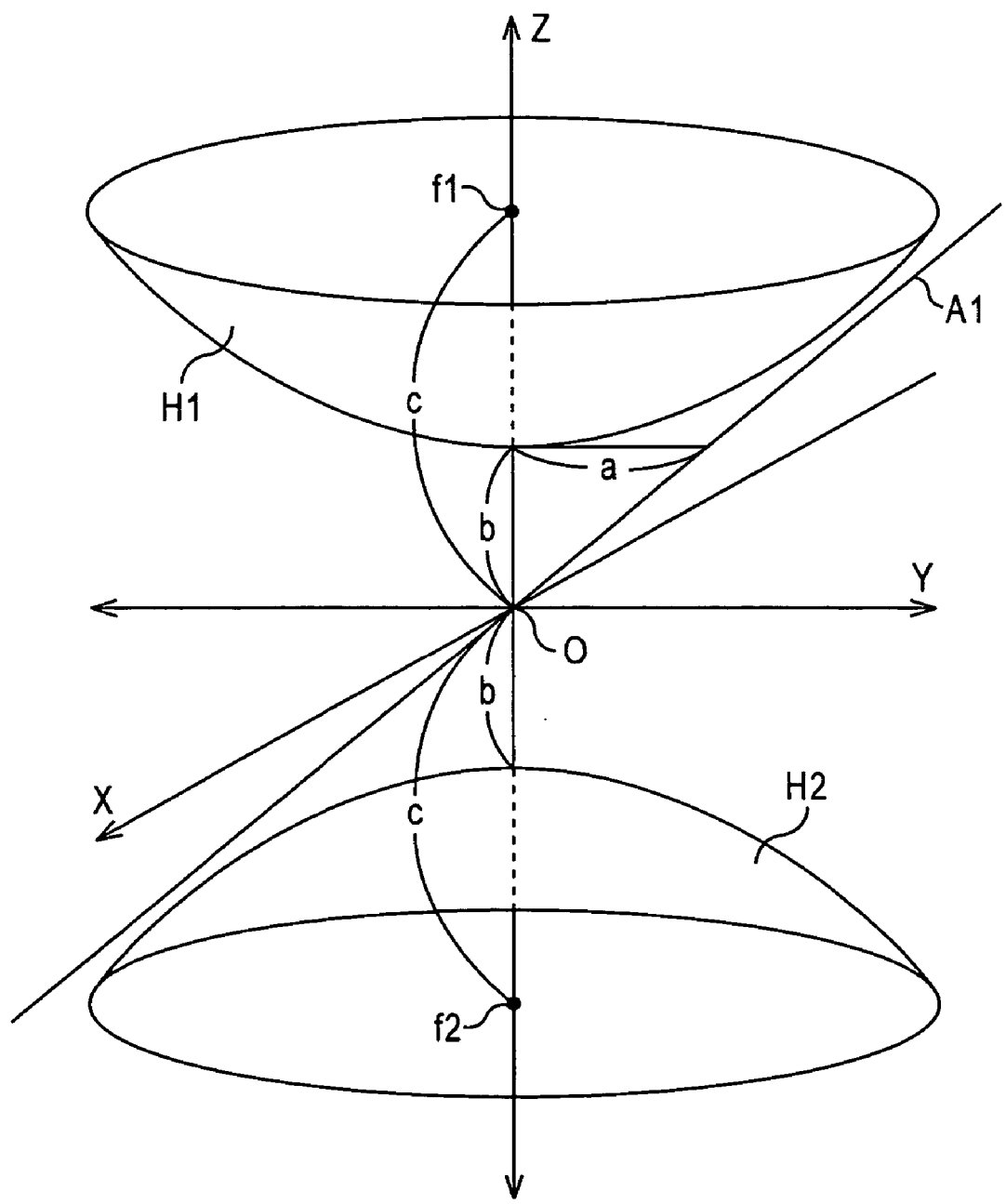
FIG. 29 is a diagram describing a hyperboloid making up a condensing unit 202.

A hyperboloid of two sheets, which is a type of hyperboloid, can be used for the condensing unit 202, and as shown in FIG. 29, a hyperboloid of two sheets is a curved surface obtained by rotating a hyperbolic curve on the axis (Z axis), and is configured of a downward convex hyperboloid H1 existing in a Z>0 region and an upward convex hyperboloid H2 existing in a 0>Z region.

Of the hyperboloid of two sheets, H1 and H2, the hyperboloid H1 in the Z>0 region is used for the condensing unit 202. Note that hereafter, the Z axis will be referred to as the center axis of the hyperbolic curve, or simply as axis, whenever appropriate.

In the three-dimensional orthogonal coordinates system of X, Y, and Z, shown in FIG. 29, the hyperboloid of two sheets, H1 and H2, are represented as shown in Expression (2).

$$\frac{X^2 + Y^2}{a^2} - \frac{Z^2}{b^2} = -1 \tag{2}$$

Here, the constants a and b in Expression (2) are constants for defining the shapes of the hyperboloids H1 and H2. That is to say, the constant b represents the distance from the point of origin O to the intersection between the hyperboloid H1 (H2) and Z axis. Also, the constant a represents the radius inscribed by the intersecting line of a plane which passes through that intersection and is parallel to the XY face and asymptotic face A1 of the hyperboloid H1 (H2).

Further, in Expression (2), a constant c is a constant for defining the position of the focal point of the hyperboloids H1 and H2. That is to say, the position +c on the Z axis (0, 0, +c) is the focal point f1 of the hyperboloid H2, and the position −c on the Z axis (0, 0, −c) is the focal point f2 of the hyperboloid H1.

The constants a, b, and c have a relation represented by the following expression.

$$c = \sqrt{a^2 + b^2} \quad (3)$$

Figure 30:
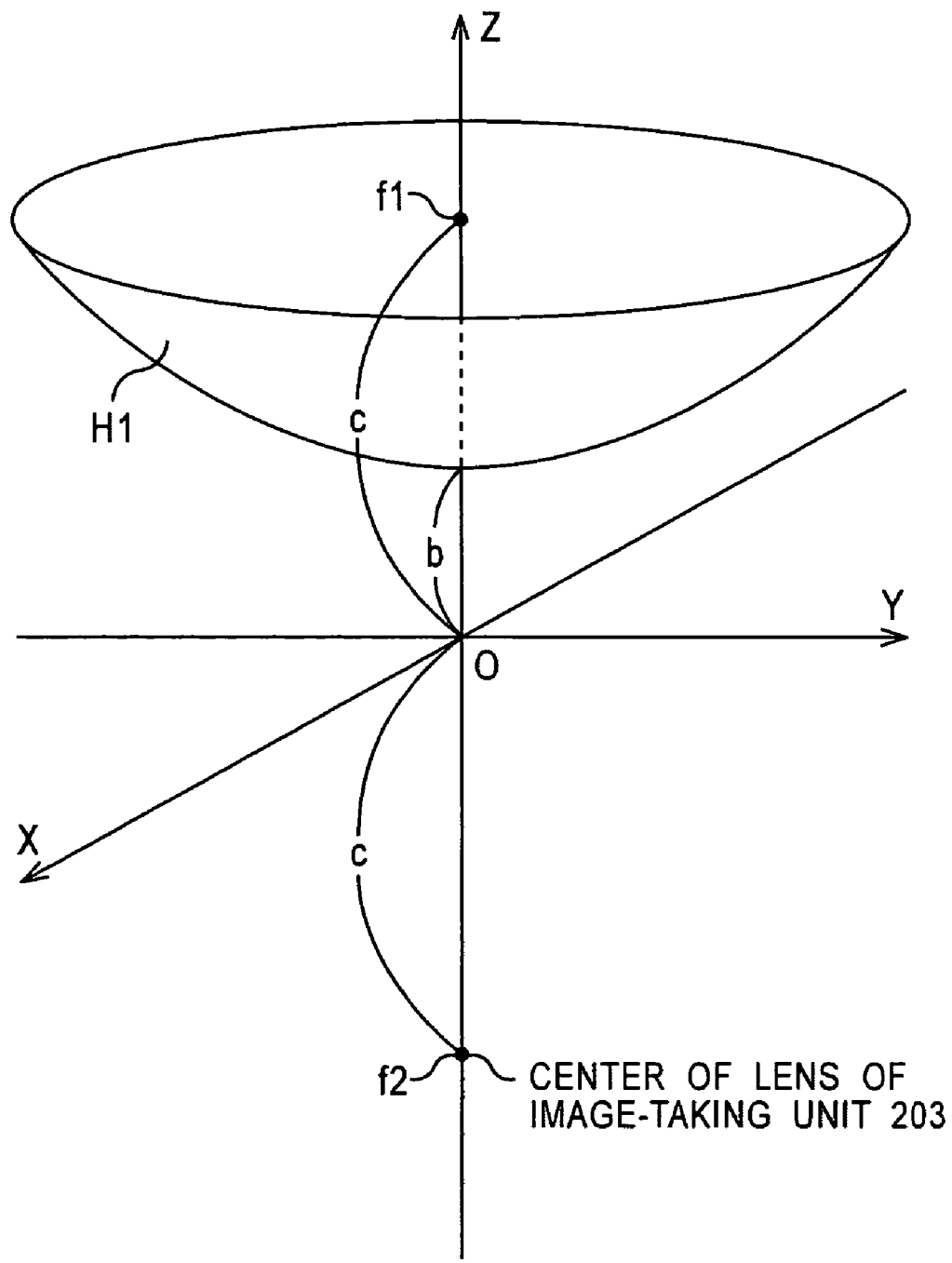
FIG. 30 is a diagram for describing the positional relation between the condensing unit 202 and an image-taking unit 203.

In the event that the condensing unit 202 is configured of a hyperboloid H1 such as described in FIG. 29, the image-taking unit 203 is positioned such that the center axis of the lens matches the Z axis, and such that the center of the lens matches the focal point f2 of the hyperboloid H1, as shown in FIG. 30.

Figure 31:
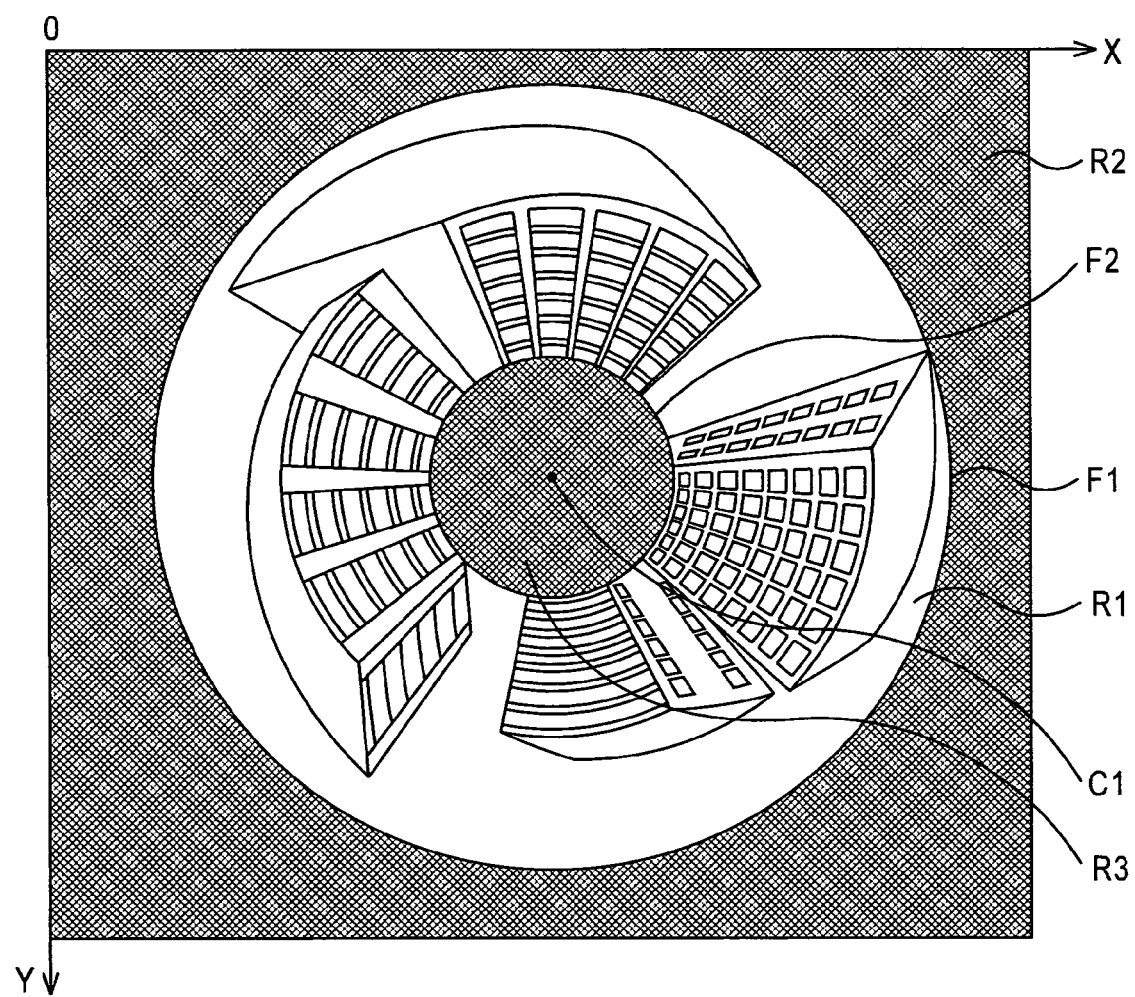
FIG. 31 is a diagram illustrating all-directional data.

Next, the all-directional image data output by the image-taking unit 203 is such as shown with FIG. 28 described above; now, with regard to this all-directional image data, a two-dimensional orthogonal coordinates system is defined wherein the point of origin O is at the upper left portion thereof, and with the x axis from the left to right direction and the y axis from the top to bottom direction, as shown in FIG. 31.

In this case, with the coordinates of the center point C1 of the circle for the perimeter F1 and the circle for the perimeter F2 as $(X_0, Y_0)$, and the radius of the circle of the perimeter F1 as $r_{F1}$ and the radius of the circle of the perimeter F2 as $r_{F2}$, the point (x, y) making up the region R2 outside of the perimeter F1 is expressed by Expression (4), and the point (x, y) making up the region R3 inside of the perimeter F2 is expressed by Expression (5).

$$(x - X_0)^2 + (y - Y_0)^2 > r_{F1}^2 \quad (4)$$

$$(x - X_0)^2 + (y - Y_0)^2 < r_{F2}^2 \quad (5)$$

Before converting the scale of the all-directional data, the scaling unit 113 shown in FIG. 26 first converts the pixel values making up the region R2 expressed by Expression (4) and the pixel values making up the region R3 expressed by Expression (5) into, for example, 0.

Now, at the time of conversion of the pixel values, the coordinates $(X_0, Y_0)$ of the center point C1, and the radii $r_{F1}$ and $r_{F2}$ are necessary, and this information is arranged to be supplied to the scaling unit 113 from the image-taking device 111 along with the zoom information. Note that the image-taking device 111 (FIG. 26) is arranged so as to output to the scaling unit 113 information related to settings of the image-taking device 111, such as the exposure time for image-taking, the aperture, and so forth, besides the zoom information, the coordinates $(X_0, Y_0)$ of the center point C1, the radii $r_{F1}$ and $r_{F2}$, as image taking information.

Here, let us assume that the exposure time and aperture are fixed, in order to simplify description.

Now, with regard to the all-directional image data which is the image data of region R1 shown in FIG. 28 and FIG. 31, there are cases wherein only part of the all-directional data is necessary, such as a portion where a desired subject is displayed, and so forth.

Figure 32:
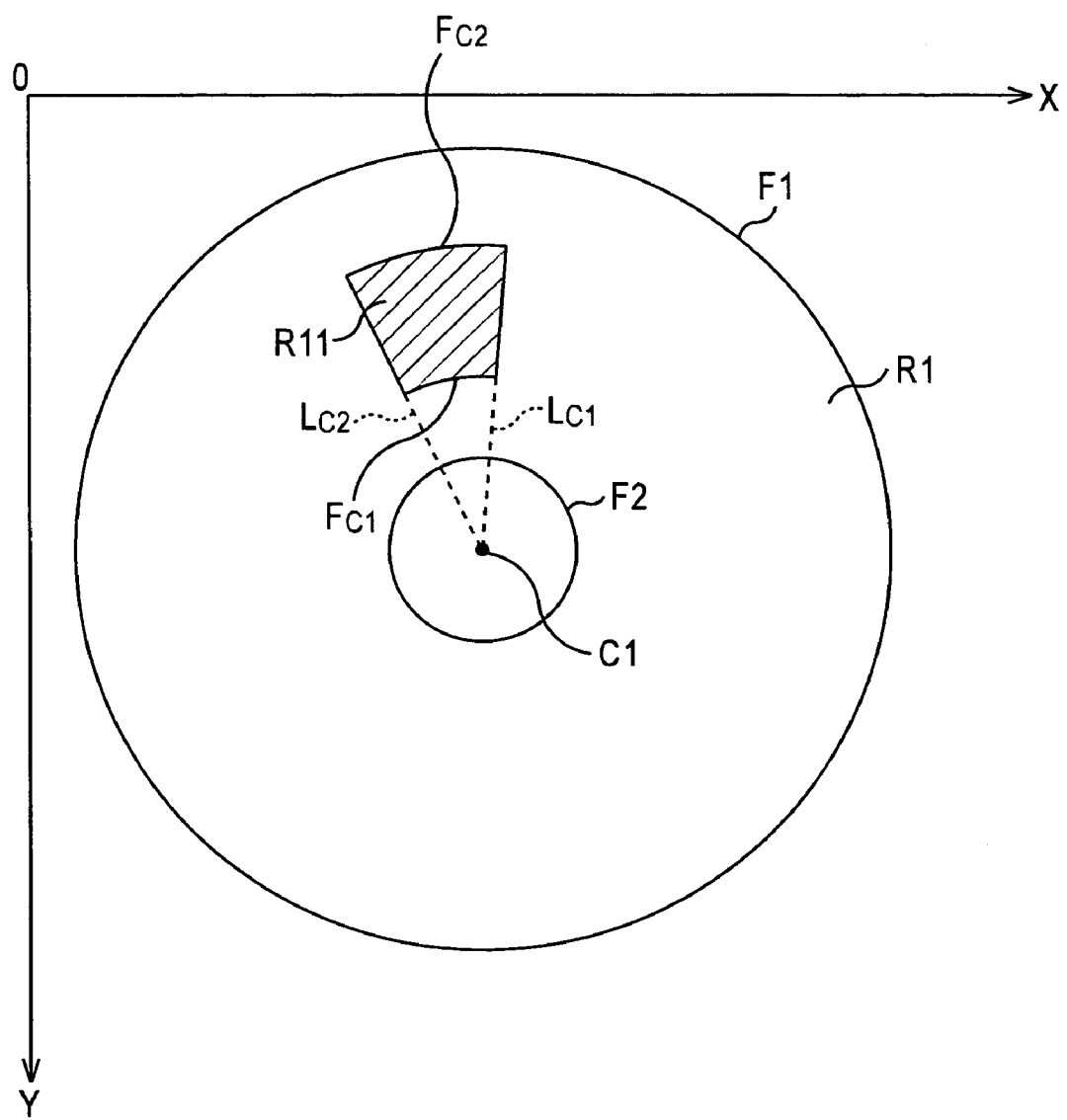
FIG. 32 is a diagram describing cropping from all-directional data.

The cropping unit 126 shown in FIG. 26 is arranged to crop out a part of the all-directional image data, with the cropping being performed as shown in FIG. 32.

That is to say, the cropping unit 126 crops out the image data in a fan-shaped region R11 which is surrounded by the two lines $L_{c1}$ and $L_{c2}$ in the radial direction which pass through the center point C1, and surrounded by the two perimeters $F_{c1}$ and $F_{c2}$ centered on the center point C1.

Next, the all-directional image data has distortion which becomes narrower the closer to the center point C1, and conversely wider the farther from the center point C1, as shown in FIG. 28 and FIG. 31. This is the same for the fan-shaped image data to be cropped out from the all-directional image data by the cropping unit 126, so such image data with distortion needs to be converted into with no distortion, to be displayed on the display unit 122 shown in FIG. 26 or the like.

The distortion of the all-directional image data such as described above, output from the all-directional camera 102, came be considered separately regarding the circumferential direction of the circle passing through the center point C1, and distortion in the radial direction.

Now, first considering the distortion in the circumferential direction, the scale of the all-directional image data in FIG. 28 and FIG. 31 is constant on the perimeter of a certain circle centered on the center point C1, and accordingly, there is no distortion.

Figure 33:
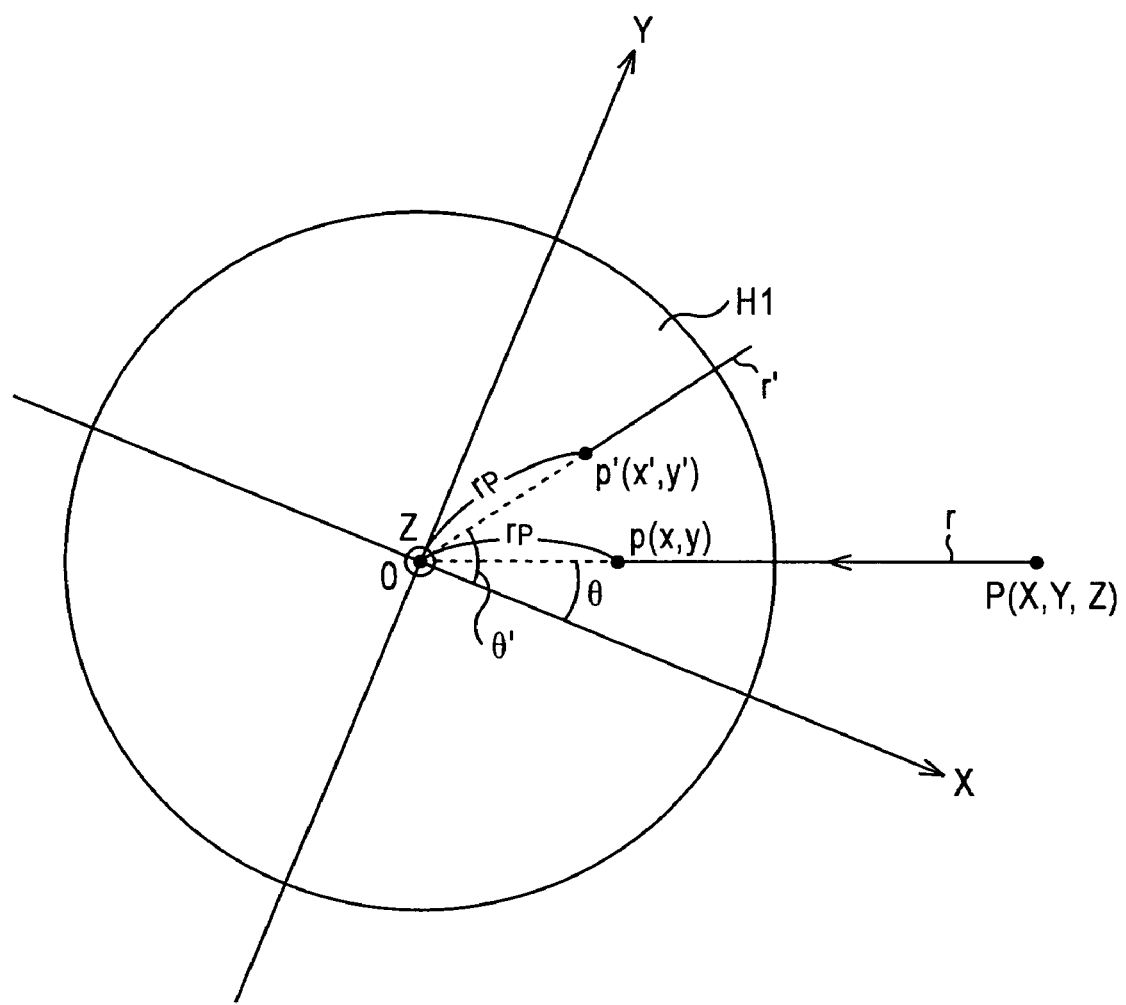
FIG. 33 is a diagram for describing deformation in the circumferential direction.

That is to say, FIG. 33 illustrates the hyperboloid H1 which is the condensing unit 202 viewed from the Z-axial direction.

In FIG. 33, a ray r is cast in from a point P (X, Y, Z) on a subject, toward the Z axis, such that there is an angle θ as to the X axis (XZ plane). The ray r is reflected at the hyperboloid H1, and reaches a point p (x, y) on a photo-reception face (image face) A3 of the image-taking unit 203 shown in FIG. 34 described later. In this case, the point p (x, y) assumes the same angle θ as to the X axis (XZ plane) as the ray r as to the X axis.

Also, considering a ray r' toward the Z axis assuming an angle θ' as to the X axis, this ray r' is also reflected at the hyperboloid H1, and reaches a point p' (x', y') on the photo-reception face (image face) A3. In this case as well, the point p' (x', y') assumes the same angle θ' as to the X axis (XZ plane) as the ray r' as to the X axis.

Also, in the event that the elevation angle (described later) of the rays r and r' are the same as to the Z axis, the rays r and r' are received at different points on the photo-reception face A3, at the same distance $r_p$ from the Z axis.

Thus, each of the multiple rays with the same elevation angle as to the Z axis are points at the same distance from the Z axis on the photo-reception face A3, and are received at points where the rays and X axis form the same angle with the X axis.

Accordingly, multiple rays with the same elevation angle as to the Z axis and the same angle as to the X axis are cast onto the perimeter of the photo-reception face A3 centered on the Z axis at constant intervals, so, with the all-directional image data, there is no distortion in the circumferential direction of a circle centered on the center point C1 which is the intersection of the photo-reception face A3 and the Z axis.

On the other hand, on a straight line in the radial direction of the all-directional image data shown in FIG. 28 and FIG. 31 passing through the center point C1, the closer to the center point C1 the smaller the scale is, and the farther from the center point C1 the greater the scale is, so the all-directional image data has distortion in the radial direction.

Figure 34:
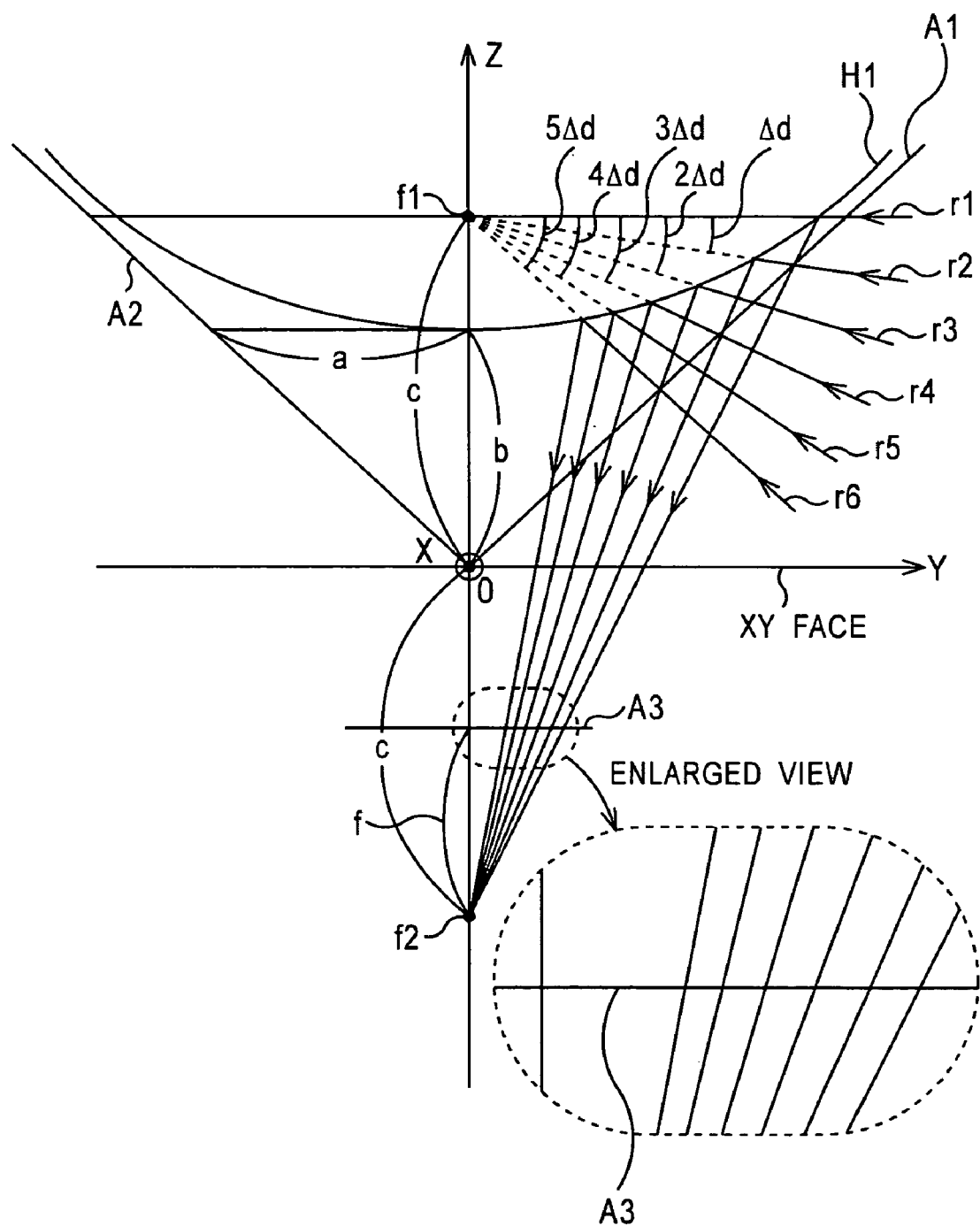
FIG. 34 is a diagram for describing deformation in the radial direction.

That is to say, FIG. 34 shows the hyperboloid H1 as the condensing unit 202 as viewed from the X-axial direction.

In FIG. 34, a ray r1 cast in toward a focal point f1 at an elevation angle of 0° as to the Z axis is reflected at the hyperboloid H1, travels toward a focal point f2, and is received at the photo-reception face (image face) A3 of the image-taking unit 203.

Now, the elevation angle as to the Z axis means an angle created between a plane which passes through the focal point f1 on the Z axis and is parallel with the XY plane, and a ray cast in toward the focal point f1. Also, with the focal distance of the image-taking device 111 as f, the photo-reception face A3 of the image-taking unit 203 is positioned a distance f away from the focal point f2 along the Z axis in the direction of the point of origin O.

A ray r2 cast in toward the focal point f1 at an elevation angle of Δd° as to the Z axis is reflected at the hyperboloid H1, travels toward the focal point f2, and is received at the photo-reception face (image face) A3 of the image-taking unit 203. A ray r3 cast in toward the focal point f1 at an elevation angle of 2Δd° as to the Z axis is reflected at the hyperboloid H1, travels toward the focal point f2, and is received at the photo-reception face (image face) A3 of the image-taking unit 203. Rays r4, r5, and r6, with elevation angles increasing by Δd° each are also received at the photo-reception face A3 in the same way.

Thus, the intervals between points received at the photo-reception face A3 for each of the rays r1 through r6 having elevation angles differing by Δd° are not at equal intervals as shown in the enlarged drawing in FIG. 34, but rather the closer the points are to the Z axis the narrow the intervals are (the farther the points are from the Z axis the wider the intervals are). That is to say, the greater the elevation angle of rays are, the narrower the intervals therebetween are (the smaller the elevation angle of rays are, the wider the intervals therebetween are).

Since the intervals between points received on the photo-reception face A3 are not equal with regard to rays with differing elevation angles, as described above, there is distortion in the all-directional image data in the radial direction.

Accordingly, to remove the distortion of the all-directional image data in the radial direction, the intervals between the photo-reception points on the photo-reception face A3 should be made equal for rays with equal angles for the elevation angle.

Figure 35:
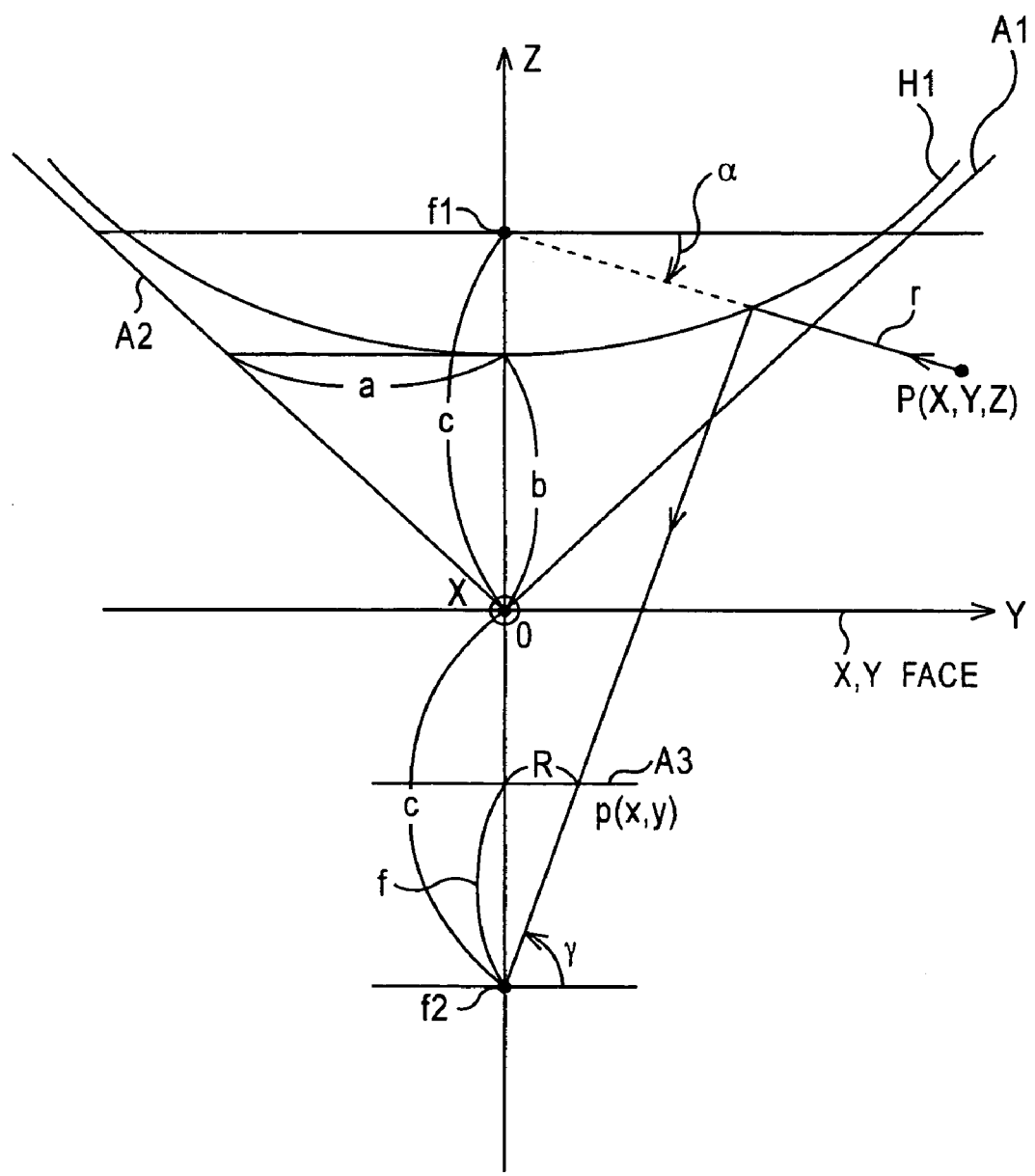
FIG. 35 is a diagram for describing a method for removing deformation in the radial direction.

Accordingly, let us now consider a ray r which is cast in toward the focal point f1 from a point P (X, Y, Z) on a subject at an elevation angle of α° as shown in FIG. 35.

This ray r is reflected at the hyperboloid H1 serving as the condensing unit 202, travels toward the focal point f2, and is received at the photo-reception face A3, in the same way as described with FIG. 34.

In this case, the angle which the ray r heading toward the focal point f2 forms with a plane which passes through the focal point f2 and is parallel to the XY plane is γ°. Further, in the two-dimensional orthogonal coordinates system defined by the X axis and Y axis, the point p where the ray r is received by the photo-reception face A3 (photo-reception point) is represented with the coordinates (x, y), and the distance between the point p (x, y) and the Z axis is represented by R.

The angle α in FIG. 35 can be expressed with the following Expression, by obtaining the coordinates of the point where the ray r is reflected at the hyperboloid H1 expressed by Expression (2).

$$\alpha = \tan^{-1} \frac{(b^2 + c^2)\sin\gamma - 2bc}{(b^2 - c^2)\cos\gamma} \quad (6)$$

From Expression (6), tan α can be obtained by the following Expression.

$$\tan\alpha = \frac{(b^2 + c^2)\sin\gamma - 2bc}{(b^2 - c^2)\cos\gamma} \quad (7)$$

Here, cos γ is defined as in the next Expression.

$$\cos\gamma = X \quad (8)$$

Substituting Expression (8) into Expression (7) yields the following Expression.

$$\{(b^2 - C^2)\tan\alpha\} \cdot X = (b^2 + c^2)\sqrt{1 - X^2} - 2bc \quad (9)$$

Expression (9) is modified to yield Expression (10).

$$\frac{(b^2 - c^2)\tan\alpha}{b^2 + c^2} \cdot X + \frac{2bc}{b^2 + c^2} = \sqrt{1 - X^2} \quad (10)$$

On the other hand, A and B are each defined as in Expressions (11) and (12).

$$A = \frac{(b^2 - c^2)\tan\alpha}{b^2 + c^2} \quad (11)$$

$$B = \frac{2bc}{b^2 + c^2} \quad (12)$$

Substituting Expressions (11) and (12) into Expression (10) yields Expression (13).

$$AX + B = \sqrt{1 - X^2} \quad (13)$$

Expression (13) can be formed as the following quadratic equation regarding X.

$$(A^2 + 1)X^2 + 2ABX + B^2 - 1 = 0 \quad (14)$$

Solving the quadratic equation of Expression (14) yields the following Expression.

$$X = \frac{-AB + \sqrt{A^2 - B^2 + 1}}{A^2 + 1} \quad (15)$$

Accordingly, the angle γ can be obtained from Expression (8) from the following Expression.

$$\gamma = \cos^{-1}(X) \quad (16)$$

Note however that in Expression (16), X is defined in Expression (15), and also, A and B in Expression (15) are defined in Expressions (11) and (12).

Also, the angle γ can be obtained from the coordinates of the point p shown in FIG. 35, from the following Expression.

$$\gamma = \tan^{-1}\left(\frac{f}{R}\right) \quad (17)$$

On the other hand, the distance R between the Z axis and point p (x, y) in FIG. 35 is expressed as $\sqrt{(x^2 + y^2)}$, and accordingly Expression (17) can be modified as in the following Expression.

$$R = \sqrt{x^2 + y^2} = \left(\frac{f}{\tan\gamma}\right) \quad (18)$$

From the above, obtaining the angle γ with Expression (16) and using the angle γ to calculate Expression (18) allows calculation of the distance R from the Z axis of the point p (x, y) where the ray r, cast in toward the focal point f1 at an elevation angle of α° as to the Z axis is received at the photo-reception face A3.

Accordingly, the distortion of the all-directional image data in the radial direction can be removed by dividing a predetermined range of elevation angle as to the Z axis (e.g., 0° through 80° or the like) into equal angles Δd, calculating distances $R_{p1}, R_{p2}, R_{p3}, \ldots$ from the Z axis for each of the points p1, p2, p3 . . . where the incident rays at the elevation angles Δd, 2Δd, 3Δd, . . . are received on the photo-reception face A3, and the all-directional image data output by the image-taking device 111 is converted so that the difference in distance between the adjacent points, $|R_{p1}-R_{p2}|$, $|R_{p2}-R_{p3}|$, . . . is constant.

Note that the conversion of the all-directional image data is performed by the image conversion unit 127 shown in FIG. 26, to remove this distortion.

Figure 36:
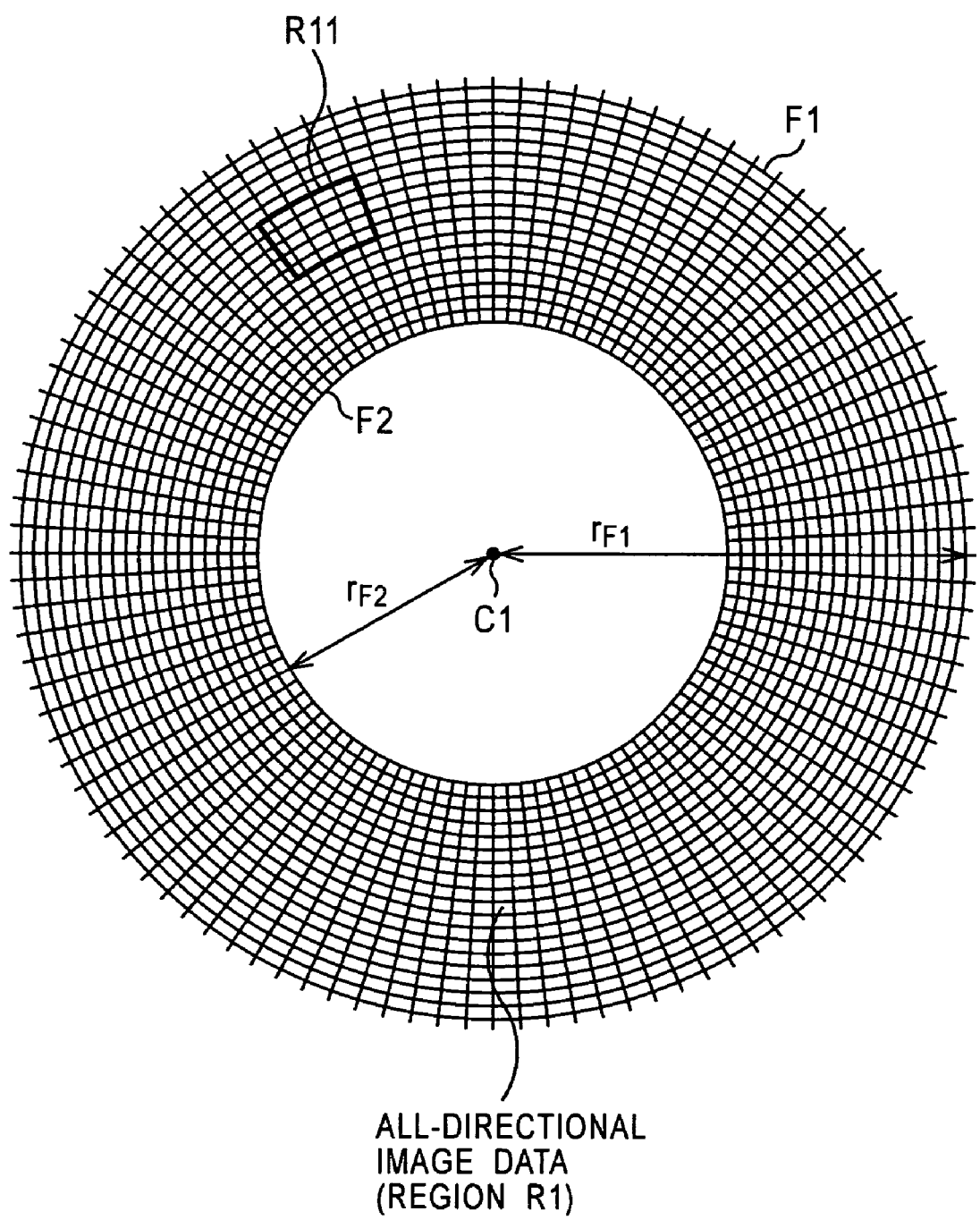
FIG. 36 is a diagram for describing a method for removing deformation in the radial direction.

That is to say, the image conversion unit 127 receives the all-directional image data with the distortion in the radial direction described above (hereafter referred to as distorted all-directional image data, as appropriate) from the control unit 118 as shown in FIG. 36, and also receives the center point C1, and the radius of the circle of the perimeter F1 as $r_{F1}$ and the radius of the circle of the perimeter F2 as $r_{F2}$.

The image conversion unit 127 then draws multiple concentric circles within the range R1 between the perimeter F1 of the circle with the radius $r_{F1}$ centered on the center point C1 and the perimeter F2 of the circle with the radius $r_{F2}$ centered on the center point C1, having the above described radii $R_{p1}$, $R_{p2}, R_{p3}, \ldots$. Further, the image conversion unit 127 draws multiple straight lines passing through the center point C1, equally dividing the multiple concentric circles. Accordingly, the image conversion unit 127 yields a great number of intersections formed between the multiple concentric circles and the multiple lines in the region R1.

Now, the great number of intersections formed between the multiple concentric circles and the multiple lines will hereafter be referred to as conversion object points, as appropriate.

From the above, the conversion object points are placed so that the adjacent ones are each at equal intervals, whereby the all-directional image data with distortion can be converted into image data from which the distortion has been removed.

Accordingly, let us now consider converting the image data of the region R11 in FIG. 36 having the same fan-shaped form as shown in FIG. 32, to that with no distortion.

Figure 37A:
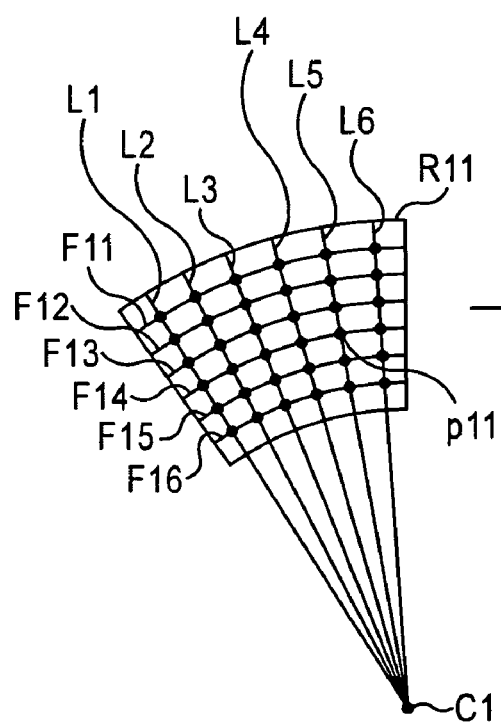
FIG. 37A is a diagram illustrating all-directional image data before removing deformation in the radial direction.
Figure 37B:
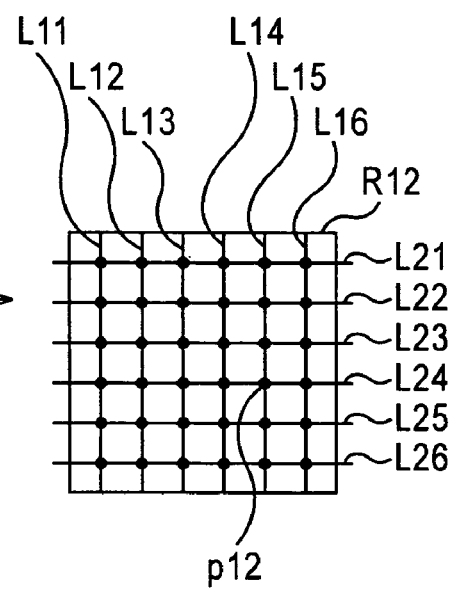
FIG. 37B is a diagram illustrating image data after removing deformation in the radial direction from the all-directional image data.

Within the region R11 there are a great number of conversion object points, which are the intersections between each of the multiple concentric arcs F11, F12, F13, F14, F15, and F16, centered on the center point C1, and each of the multiple straight lines L1, L2, L3, L4, L5, and L6, as shown in FIG. 37A. The image conversion unit 127 arrays the great number of conversion object points existing within the region R11 such that the adjacent ones are at equal intervals, as shown in FIG. 37B.

That is to say, the image conversion unit 127 assumes equidistantly placed horizontal straight lines L21, L22, L23, L24, L25, and L26, corresponding to each of the arcs F11, F12, F13, F14, F15, and F16, shown in FIG. 37A, and equidistantly placed vertical straight lines L11, L12, L13, L14, L15, and L16, corresponding to each of the multiple straight lines L1, L2, L3, L4, L5, and L6, as shown in FIG. 37A, and converts (assigns) corresponding object points on the intersection points between each of the horizontal straight lines L21 through L26 and each of the vertical straight lines L11 through L16.

Accordingly, in FIG. 37A for example, the conversion object point p11 which is the intersection between the arc F14 and the straight line L5 is converted into the intersection p12 between the straight line L24 corresponding to the arc 14 and the straight line L15 corresponding to the straight line L5.

Now, as described above, the image conversions unit 127 converts the image data having the distortion in the radial direction into image data from which the distortion has been removed, by performing conversion (changing) of the position of the conversion object points, with the conversion object points being the intersections between circles centered on the center point C1 and straight lines passing through the center C1, as described above. Accordingly, the conversion object points do not necessarily match the pixel centers of the pixels making up the photo-reception face A3 (FIG. 34, FIG. 35) of the image-taking unit 203 (FIG. 27), and rather, generally, these often do not match.

In this way, the conversion object points are generally off from the pixel centers, so there is the need for the image conversion unit 127 to obtain the pixel values at the conversion object points before converting the positions of the conversion object points.

Accordingly, the image conversion unit 127 is arranged so as to obtain the pixel values at the conversion object points as follows, for example.

Figure 38:
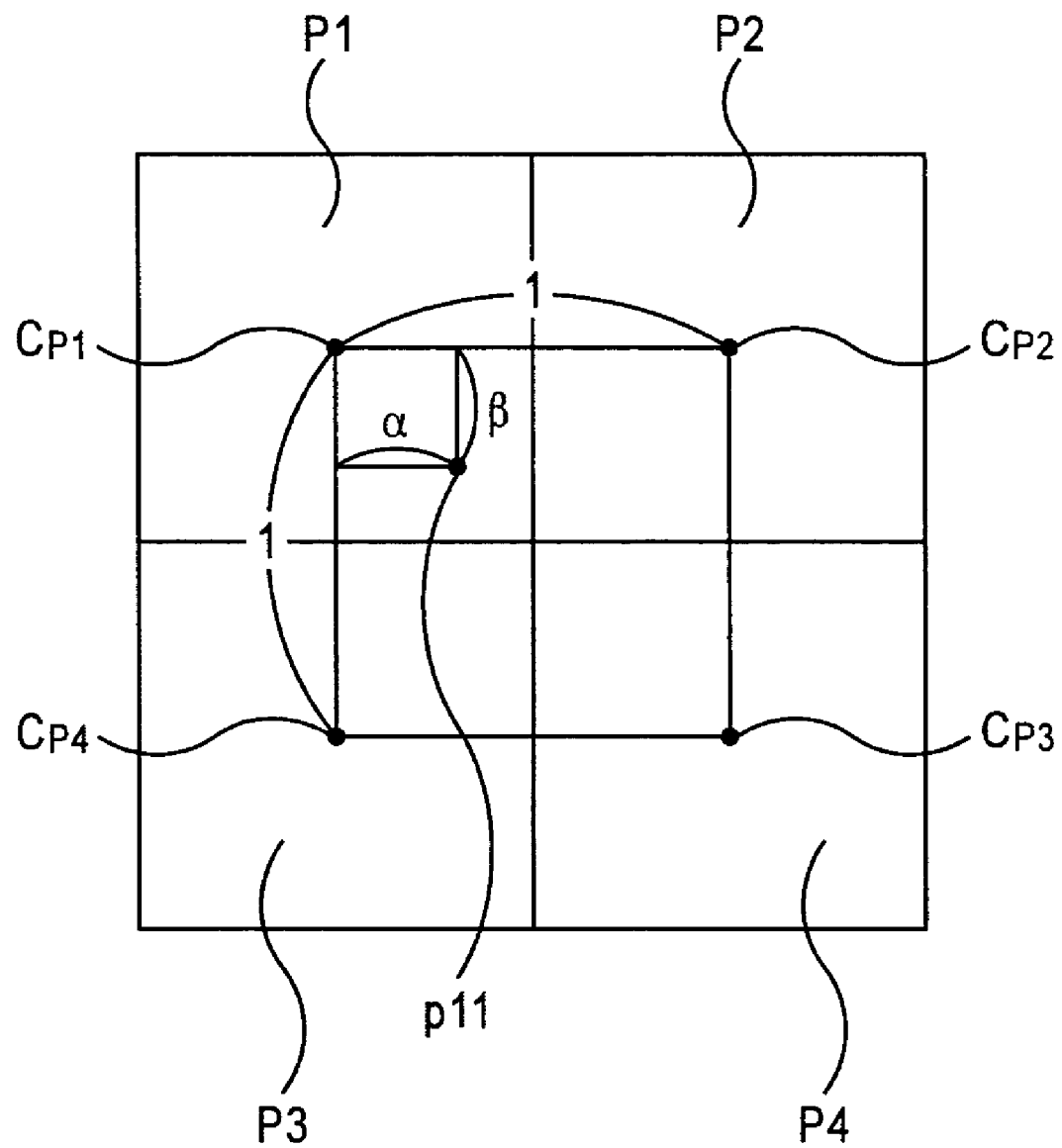
FIG. 38 is a diagram for describing how to obtain pixel values at a point to be converted.

That is to say, let us say that the conversion object point p11 shown in FIG. 37 is within the range of a rectangle (square) having vertexes of $C_{P1}$, $C_{P2}$, $C_{P3}$, and $C_{P4}$, which are pixel centers of the four pixels P1, P2, P3, and P4, which are adjacent on two-by-two fashion on the photo-reception face A3 as shown in FIG. 38. In the embodiment shown in FIG. 38, the distance between vertically and horizontally adjacent pixel centers is 1.

In the event that the conversion object point p11 is a point which is to the right of the center pixel $C_{P1}$ by a distance α and down by a distance β, the image conversion unit 127 takes a pixel value $S_s$ obtained with the following Expression, for example, as the pixel value of the conversion object point p11.

$$S_s = \{S_a \cdot (1-\alpha) + \alpha \cdot S_b\}(1-\beta) + \beta \cdot \{S_c \cdot (1-\alpha) + \alpha \cdot S_d\} \quad (19)$$

In Expression (19), $S_a$, $S_b$, $S_c$, and $S_d$ each represent the pixel values of the pixels P1, P2, P3, and P4. Also, in expression (19), α and β are values within the range of 0 or greater and 1 or smaller, corresponding to the position of the conversion object point p11.

Next, the scaling unit 113 shown in FIG. 26, as described above, converts the all-directional image data taken with the all-directional camera $102_k$ with an arbitrary zoom magnification, into that taken with a predetermined zoom magnification. This zoom magnification conversion may be realized by simple pixel interpolation and thinning, and necessary filtering such as low-pass filter and the like, but in order to improve magnification, the class classification adaptation processing already proposed by the present applicant, for example, may be used instead of simple pixel interpolation.

Class classification adaptation processing is made up of class classification processing and adaptation processing, wherein the data is divided into classes based on the nature thereof in the class classification processing, and adaptation processing is implemented for each class.

Now, the adaptation processing will be described, with regard to an example of a case of converting an image of low magnification (hereafter referred to as low-magnification image, as appropriate) into an image of high magnification (hereafter referred to as high-magnification image, as appropriate).

In this case, with the adaptation processing, linear combination of pixels making up a low-magnification image (hereafter referred to as low-magnification pixels, as appropriate) and predetermined tap coefficients yields prediction values of pixels of a high-magnification image wherein the spatial resolution of the low-magnification image has been improved, thereby obtaining an image wherein the magnification of the low-magnification image has been raised.

Specifically, for example, let us consider taking a high-magnification image as tutor data and a low-magnification image wherein the resolution of the high-magnification image has been deteriorated as student data, and obtaining a prediction value E[y] of a pixel value y of a pixel making up the high-magnification image (hereafter referred to as high-magnification pixel, as appropriate), by a linear combination model stipulated by linear combination of the pixel values $x_1$, $x_2$, ... of several low-magnification pixels (pixels making up a low-resolution image) and predetermined tap coefficients $w_1$, $w_2$, .... In this case, the prediction value E[y] can be expressed with the following Expression.

$$E[y] = w_1 x_1 + w_2 x_2 + \quad (20)$$

In order to generalize Expression (20), defining a matrix W of a group of tap coefficients $w_j$, a matrix X of a group of student data $x_{ij}$, and a matrix Y' of a group of prediction values $E[y_j]$, as $$X = \begin{pmatrix} x_{11} & x_{12} & \dots & x_{1J} \\ x_{21} & x_{22} & \dots & x_{2J} \\ \dots & \dots & \dots & \dots \\ x_{I1} & x_{I2} & \dots & x_{IJ} \end{pmatrix}$$

$$W = \begin{pmatrix} W_1 \\ W_2 \\ \dots \\ W_J \end{pmatrix}, Y' = \begin{pmatrix} E[y_1] \\ E[y_2] \\ \dots \\ E[y_I] \end{pmatrix}$$

yields the following observational equation $$XW = Y' \quad (21)$$

Here, the component $x_{ij}$ of the matrix X means the j'th student data in the i'th student data group (the group of student data used for prediction of the i'th tutor data $y_i$), and the component $w_j$ of the matrix W means the tap coefficient of which the product with the j'th student data in the student data group is computed. Also, $y_i$ means the i'th tutor data, and accordingly, $E[y_i]$ means the prediction value of the i'th tutor data. Note that the y to the left side of Expression (20) has the suffix i of the matrix Y component $y_i$ omitted, and also, the $x_1$, $x_2$, ... to the right side of Expression (20) have the suffix i of the matrix X component $x_{ij}$ omitted.

Let us consider obtaining a prediction value E[y] close to the pixel value y of the high-magnification pixel by applying the leas-square method to the observational equation of Expression (21). In this case, defining a matrix Y of a group of true pixel values y of high-magnification pixels to serve as the tutor data, and a matrix E of a group of the residual error e of the prediction value E[y] as to the pixel value y of the high-magnification pixel, as $$E = \begin{pmatrix} e_1 \\ e_2 \\ \dots \\ e_I \end{pmatrix}, Y = \begin{pmatrix} y_1 \\ y_2 \\ \dots \\ y_I \end{pmatrix}$$

Establishes the following residual equation from Expression (21).

$$XW = Y + E \quad (22)$$

In this case, the tap coefficient $w_j$ for obtaining the prediction value E[y] close to the pixel value y of the high-magnification pixel can be obtained by minimizing the squared error $$\sum_{i=1}^{I} e_i^2$$

Accordingly, in the event that differentiation of the above squared error by the tap coefficient $w_j$ yields 0, this means that the tap coefficient $w_j$ which satisfies the following Expression is the optimal value for obtaining the prediction value E[y] close to the pixel value y of the high-magnification pixel.

$$e_1 \frac{\partial e_1}{\partial w_j} + e_2 \frac{\partial e_2}{\partial w_j} + \dots e_I \frac{\partial e_I}{\partial w_j} = 0 \ (j = 1, 2, \dots, J) \quad (23)$$

Accordingly, first, differentiation of the Expression (22) with the tap coefficient $w_j$ establishes the following expression.

$$\frac{\partial e_i}{\partial w_1} = x_{i1}, \frac{\partial e_i}{\partial w_2} = x_{i2}, \dots, \frac{\partial e_i}{\partial w_J} = x_{iJ}, (i = 1, 2, \dots, I) \quad (24)$$

Expression (23) and Expression (24) yield Expression (25).

$$\sum_{i=1}^{I} e_i x_{i1} = 0, \sum_{i=1}^{I} e_i x_{i2} = 0, \dots \sum_{i=1}^{I} e_i x_{iJ} = 0 \quad (25)$$

Further, taking into consideration the relation between the student data $x_{ij}$, tap coefficient $w_j$, tutor data $y_i$, and residual error $e_i$ in the residual error expression of Expression (22), the following normal equations can be obtained from Expression (25).

$$\begin{cases} \left(\sum_{i=1}^{I} x_{i1}x_{i1}\right) w_1 + \left(\sum_{i=1}^{I} x_{i1}x_{i2}\right) w_2 + \dots + \left(\sum_{i=1}^{I} x_{i1}x_{iJ}\right) w_J = \left(\sum_{i=1}^{I} x_{i1}y_i\right) \\ \left(\sum_{i=1}^{I} x_{i2}x_{i1}\right) w_1 + \left(\sum_{i=1}^{I} x_{i2}x_{i2}\right) w_2 + \dots + \left(\sum_{i=1}^{I} x_{i2}x_{iJ}\right) w_J = \left(\sum_{i=1}^{I} x_{i2}y_i\right) \\ \dots \\ \left(\sum_{i=1}^{I} x_{iJ}x_{i1}\right) w_1 + \left(\sum_{i=1}^{I} x_{iJ}x_{i2}\right) w_2 + \dots + \left(\sum_{i=1}^{I} x_{iJ}x_{iJ}\right) w_J = \left(\sum_{i=1}^{I} x_{iJ}y_i\right) \end{cases} \quad (26)$$

Further, the normal equations of Expression (26) can be expressed as $$AW = v \quad (27)$$

by defining the matrix (convariance matrix) A and vector v as $$A = \begin{pmatrix} \sum_{i=1}^{I} x_{i1}x_{i1} & \sum_{i=1}^{I} x_{i1}x_{i2} & \cdots & \sum_{i=1}^{I} x_{i1}x_{iJ} \\ \sum_{i=1}^{I} x_{i2}x_{i1} & \sum_{i=1}^{I} x_{i2}x_{i2} & \cdots & \sum_{i=1}^{I} x_{i2}x_{iJ} \\ \sum_{i=1}^{I} x_{iJ}x_{i1} & \sum_{i=1}^{I} x_{iJ}x_{i2} & \cdots & \sum_{i=1}^{I} x_{iJ}x_{iJ} \end{pmatrix}$$

$$v = \begin{pmatrix} \sum_{i=1}^{I} x_{i1}y_{i} \\ \sum_{i=1}^{I} x_{i2}y_{i} \\ \vdots \\ \sum_{i=1}^{I} x_{iJ}y_{i} \end{pmatrix}$$

and defining the vector W as in Expression 20.

As many normal equations of Expression (26) can be provided as the number J of the tap coefficient $w_j$ to be obtained, by preparing a certain number of sets of student data $x_{ij}$ and tutor data $y_i$, and accordingly, solving Expression (27) with regard to the vector W allows an optimal tap coefficient $w_j$ to be obtained (however, the matrix A in Expression (27) needs to be a regular matrix in order to solve Expression (27)). Note that sweeping (Gauss-Jordan elimination) or the like, for example, may be used for solving Expression (27).

Using student data and tutor data to learn an optimal tap coefficient $w_j$ beforehand, and further using the tap coefficient $w_j$ to obtain the prediction value E[y] close to the tutor value y, as described above, is the adaptation processing.

Note that adaptation processing is different from simple interpolation with regard to the point that components not contained in the low-magnification image but contained in the high-magnification image are reproduced. That is to say, adaptation processing may seem to be the same as simple interpolation using a so-called interpolation filter just from looking at Expression (20), but the tap coefficient w equivalent to the tap coefficient of the interpolation filter can be obtained by learning, as if it were, using the tutor data y, so components contained in the high-magnification image can be reproduced. Accordingly, it can be said that the adaptation processing has image creating (resolution creating) actions, as if it were.

Figure 39:
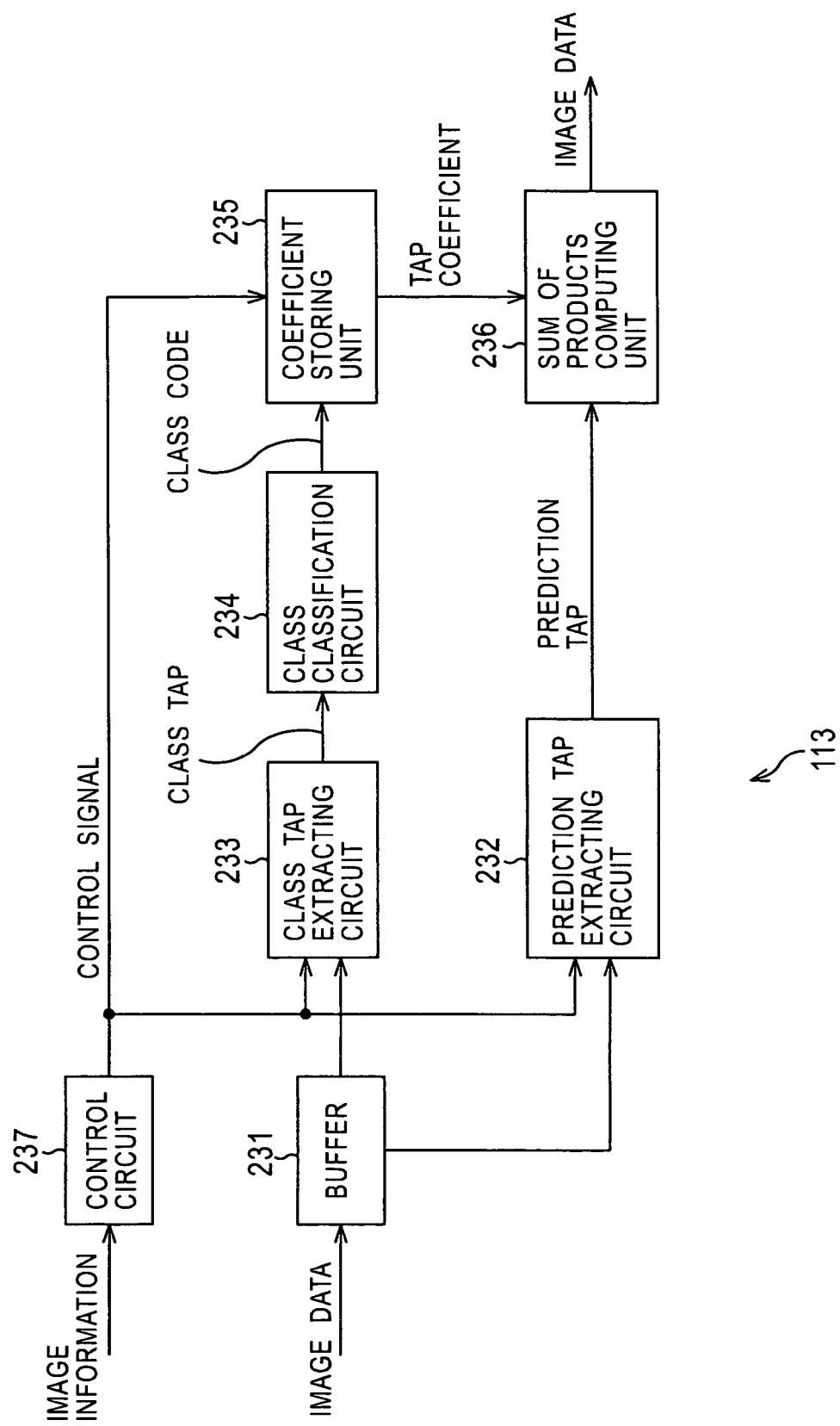
FIG. 39 is a block diagram illustrating an electrical configuration example of a scaling unit 113.

Next, FIG. 39 illustrates a configuration example of the scaling unit 113 realized by a class classification adaptation processing circuit which performs class classification adaptation processing such as described above. Here, the scaling unit 113 converts the all-directional image data into image data with a predetermined fixed magnification, and in the event that the all-directional image data is of a magnification lower than the predetermined fixed magnification, the all-directional image data is converted into image data with the fixed magnification higher than that magnification, and conversely, in the event that the magnification of the all-directional image data is higher than the predetermined fixed magnification, the all-directional image data is converted into image data with the predetermined fixed magnification lower than that magnification, with FIG. 39 illustrating a class classification adaptation processing circuit making up the part for converting the all-directional image data into the image data with the fixed magnification higher than that magnification.

The low-magnification image data which is image data (all-directional image data) output from the all-directional camera $102_k$ is supplied to the buffer 231, and the buffer 231 temporarily stores the low-magnification image data supplied thereto.

A prediction tap extracting circuit 232 sequentially takes pixels of image data of the fixed magnification to be obtained with a later-described sum of products computing circuit 236 (hereafter referred to as fixed magnification pixel, as appropriate) as pixels of interest, and further extracts from the buffer 231 pixels of the low-magnification image data to be used for predicting the pixel of interest, and takes these as prediction taps.

That is, the prediction tap extracting circuit 232 reads out from the buffer 231 several low-magnification pixels near the position corresponding to the fixed magnification pixel serving as the pixel of interest, for example, as a prediction tap.

Upon the prediction tap extracting circuit 232 obtaining a prediction tap, the prediction tap regarding that pixel of interest is supplied to the product of sums computing circuit.

Now, control signals are supplied to the prediction tap extracting circuit 232 from the control circuit 237, and the prediction tap extracting circuit 232 determines the low-magnification pixels to configure the prediction tap with, i.e., the structure of the prediction tap, according to the control signals from the control circuit 237.

That is to say, image-taking information output from the image-taking device 111 of the all-directional camera $102_k$ is supplied to the control circuit 237, and the control circuit 237 generates, based on zoom information, control signals for ensuring processing suitable for the magnification which the zoom information, for example, of the image-taking information, represents, which is supplied to the prediction tap extracting circuit 232, class tap extracting circuit 233, and coefficient storage unit 235.

Specifically, the control circuit 237 generates control signals which instruct configuring the prediction tap using low-magnification pixels that are at positions closer to the position corresponding to the pixel of interest the smaller the zoom magnification which the zoom information indicates is, for example (control signals which instruct configuring the prediction tap using low-magnification pixels that are at positions farther from the position corresponding to the pixel of interest the greater the zoom magnification is), and supplies to the prediction tap extracting unit 232.

Accordingly, the prediction tap extracting unit 232 configures prediction taps of different structures according to the zoom magnification of the low-magnification image, according to such control signals.

On the other hand, the class tap extracting unit 233 extracts low-magnification pixels used for class classification for classifying the pixel of interest into one of several classes, from the buffer 231, and takes this as a class tap.

Now, the class tap extracting unit 233 also determines the low-magnification pixels to configure the prediction tap with, i.e., the structure of the class tap, according to the control signals from the control circuit 237.

That is to say, the control circuit 237 supplies control signals to the class tap extracting circuit 233 in the same way as to the prediction tap extracting circuit 232, and accordingly the class tap extracting circuit 233 configures the class tap using low-magnification pixels that are at positions closer to the position corresponding to the pixel of interest the smaller the zoom magnification which the zoom information indicates is (configures the class tap using low-magnification pixels that are at positions farther from the position corresponding to the pixel of interest the greater the zoom magnification is)

Now, in order to simplify description here, let us say that the prediction tap obtained at the prediction tap extracting circuit 232 and the class tap obtained at the class tap extracting circuit 233 have the same tap structure, for example. However, it is needless to say that the prediction tap and class tap can have independent (separate) tap structures.

A class tap regarding a pixel of interest obtained by the class tap extracting circuit 233 is supplied to the class classification circuit 234. The class classification circuit 234 performs class classification of the pixel of interest based on the class tap from the class tap extracting circuit 233, and outputs a class code corresponding to the consequently obtained class.

Now, ADRC (Adaptive Dynamic Range Coding) or the like, for example, can be used for the class classification method.

With a method using ADRC, pixel values of pixels making up a class tap are subjected to ADRC processing, and the class of the pixel of interest is determined according to the ADRC code obtained as a result thereof.

In K-bit ADRC, the maximum value MAX and minimum value MIN of multiple pixel values making up a class tap are detected for example, DR=MAX−MIN is taken as a local dynamic range of a group, and the pixels making up the class tap are re-quantized into K bits based on the dynamic range DR. That is to say, the smallest value MIN is subtracted from the pixel value of each of the pixels making up the class tap, and the subtracted value thereof is divided by $DR/2^K$ (quantization). The pixel values of each of the K bits making up the class tap that are obtained as described above are arrayed into a bit string according to a predetermined order, which is output as ADRC code. Accordingly, fir example, in the event that a class tap is subjected to 1-bit ADRC processing, the pixel value of each pixel making up the class tap have the minimum value MIN subtracted therefrom, and then are divided by the average value of the maximum value MAX and minimum value MIN, so that the pixel value of each pixel is 1 bit (binarized). A bit string wherein the 1-bit pixel values are arrayed in a predetermined order is output as the ADRC code.

Now, while the level distribution (pixel value distribution) pattern of the pixels making up the class-tap, for example can be output from the class classification circuit 234 without change, in this case, in the event that the class tap is made up of N pixels and K bits are assigned to each pixel, the number of versions of class codes which the class classification circuit 234 outputs is $(2^N)^K$, which is a great number increasing exponentially according to the number of pixel bits K.

Accordingly, the class classification circuit 234 preferably performs class classification after subjecting the amount of information of the class tap to compressing by the above-described ADRC processing or vector quantization or the like.

Also, while the arrangement here performs class classification using low-magnification pixels alone, but class classification may be performed using zoom information or exposure time or the like contained in the image-taking information, along with the low-magnification pixels (or instead of the low-magnification pixels), as class taps.

The class code output by the class classification circuit 234 is provided to the coefficient storage unit 235 as an address.

The coefficient storage unit 235 stores tap coefficients obtained by learning processing being performed, and outputs tap coefficients stored at addresses corresponding to the class codes output by the class classification circuit 234 to the sum of products computing circuit 236.

Note that the coefficient storage unit 235 stores multiple sets of tap coefficients obtained by performing learning using multiple sets of tutor data and student data, as described later. At the coefficient storage unit 235, which set of tap coefficients to use from the multiple sets of tap coefficients is determined according to control signals from the control circuit 237.

That is to say, the coefficient storage unit 235 is configured of multiple banks, for example, with each of the banks storing corresponding sets of the multiple sets of tap coefficients obtained by performing learning for each range of multiple zoom magnifications. The control circuit 237 generates control signals for instructing the bank corresponding to the zoom magnification indicated by the zoom information, based on the zoom information in the image-taking information, and supplies to the coefficient storage unit 235. The coefficient storage unit 235 switches banks according to control signals from the control circuit 237, and outputs from the tap coefficient sets stored in the selected bank, one which corresponds to the class code supplied from the class classification circuit 234 to the sum of products computing circuit 236.

The sum of products computing circuit 236 obtains the production tap output by the prediction tap extracting circuit 232 and the tap coefficient output by the coefficient storage unit 235, performs the linear prediction computation (sum-of-product computation) shown in Expression (20) using the prediction tap and the tap coefficient, and outputs the computation results as the pixel value of the fixed magnification pixel which is the pixel of interest.

Figure 40:
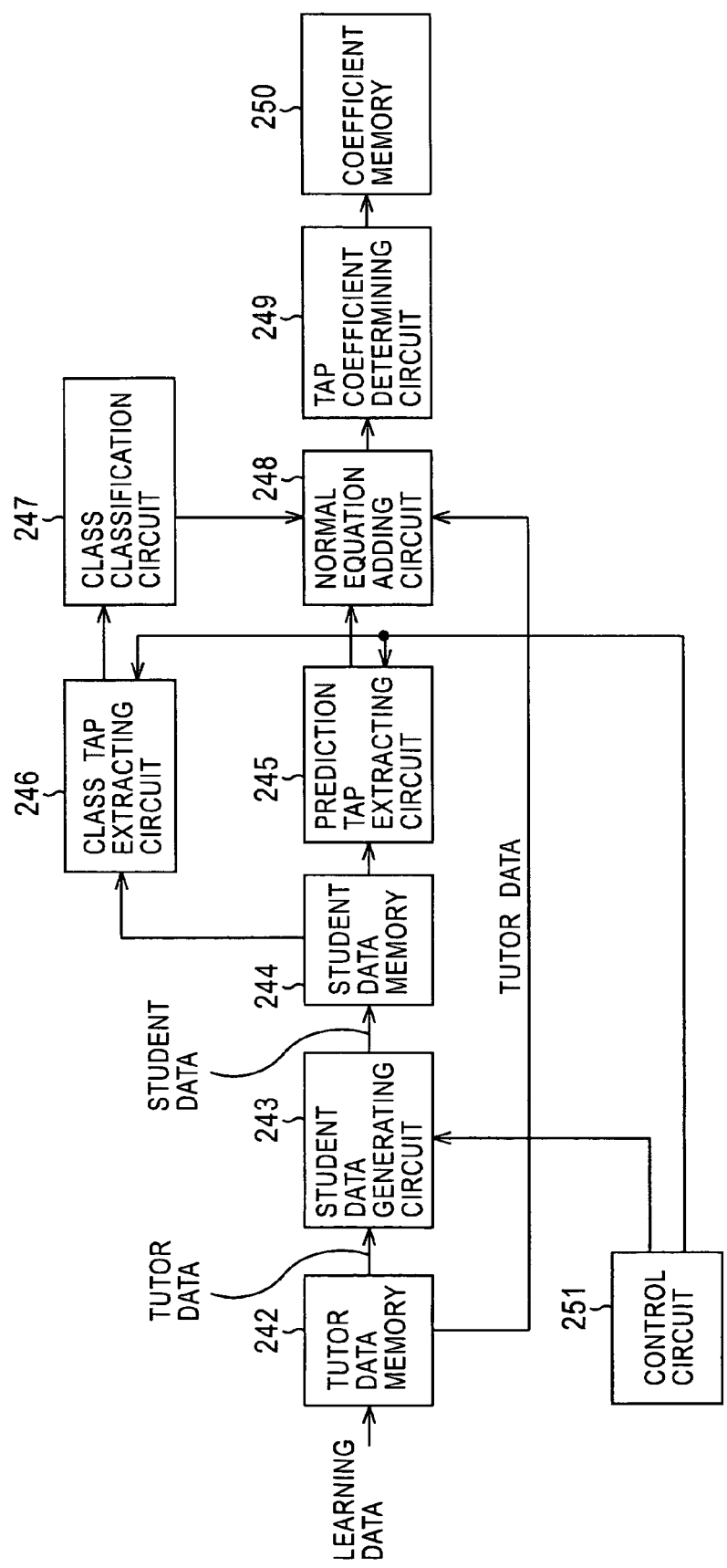
FIG. 40 is a block diagram illustrating an electrical configuration example of a learning device for learning tap coefficients.

Next, FIG. 40 illustrating a configuration example of a learning device which performs learning of tap coefficients to be stored in the coefficient storage unit 235 shown in FIG. 39.

Learning data used for learning is supplied to tutor data memory 242. Now, image data of a fixed magnification (hereafter referred to as fixed-magnification image data, as appropriate) is used as learning data.

The tutor data memory 242 stores the fixed-magnification image data supplied thereto as tutor data to serve as the tutor in the learning. A student data generating circuit 243 generates student data to serve as the student in the learning from the tutor data stored in the tutor data memory 242, according to the control signals supplied from a control circuit 251.

That is to say, the control circuit 251 has multiple zoom magnification ranges set, and the control circuit 251 selects one of the multiple zoom magnification ranges as a range of interest. The control circuit 251 then determines a representative value of the zoom magnification of the range of interest (e.g., a central value of the zoom magnification of the range of interest), and generates control signals based on the representative value of the zoom magnification, which is supplied to the student data generating circuit 243, prediction tap extracting circuit 245, and class tap extracting circuit 246.

Specifically, the control circuit 251 calculates thinning out ratio for making the fixed-magnification image data serving as the tutor data stored in the tutor data memory 242 to be image data having the zoom magnification of the representative value, and supplies control signals to the student data generating circuit 243 which instruct thinning out of the tutor data at that thinning out ratio.

The student data generating circuit 243 thins out the tutor data stored in the tutor data memory 242 according to the above-described control signals, and accordingly generates image data of the zoom magnification of the representative value as student data. The student data is supplied from the student data generating circuit 243 to the student data memory 244, and is stored.

Upon student data being requested regarding the tutor data stored in the tutor data memory 242 and stored in the student data memory 244, the prediction tap extracting circuit 245 sequentially takes the tutor data stored in the tutor data memory 242 as a pixel of interest, and further extracts the student data to be used for predicting the pixel of interest from the student data memory 244, which is used as a prediction tap.

Now, the control circuit 251 generates control signals in the same way as with the control circuit 237 in FIG. 39, based on the zoom magnification of the representative value, and supplies this to the prediction tap extracting circuit 245. The prediction tap extraction circuit 245 then makes up a prediction tap which is the same as the case of the prediction tap extracting circuit 232 shown in FIG. 39, based on the control signals supplied from the control circuit 251.

Thus, the prediction tap obtained by the prediction tap extracting circuit 245 is supplied to a normal equation adding circuit 248.

On the other hand, the class tap extracting circuit 246 extracts student data to be used for class classification of pixels of interest from the student data memory 244, and supplies to the class classification circuit 247 as class taps.

Now, the control circuit 251 generates control signals which are the same as those of the control circuit 237 shown in FIG. 39 based on the zoom magnification of the representative value, and supplies this to the class tap extracting circuit 246. The class tap extracting circuit 246 configures class taps the same as the case of the class tap extracting circuit 233 shown in FIG. 39, according to the control signals supplied from the control circuit 251.

Upon receiving supply of a class tap regarding a pixel of interest from the class tap extracting circuit 246, the class classification circuit 247 uses the class tap to perform the same class classification as the class classification circuit 234 shown in FIG. 39, and supplies the class code representing the class of the pixel of interest to the normal equation adding circuit 248.

The normal equation adding circuit 248 reads out the tutor data serving as the pixel of interest from the tutor data memory 242, and performs adding to the student data making up the prediction tap from the prediction tap extracting circuit 245 and the tutor data serving as the pixel of interest, for each class supplied from the class classification circuit 247.

That is, the normal equation adding circuit 248 performs computation equivalent to multiplication ($x_{in}$ $x_{im}$) and summation ($\Sigma$) of student data one with another, which are the components of the matrix A in Expression (27), using the prediction taps (student data) for each class corresponding to the class code supplied from the class classification circuit 247.

Further, the normal equation adding circuit 248 performs computation equivalent to multiplication ($x_{in}$ $y_i$) and summation ($\Sigma$) of student data and tutor data, which are the components of the vector v in Expression (27), using the prediction taps (student data) and pixel of interest (tutor data) for each class corresponding to the class code supplied from the class classification circuit 247, in the same way.

The normal equation adding circuit 248 performs the above-described adding in as pixels of interest for all tutor data sorted in the tutor data memory 242, and accordingly establishes normal equations for each class, as shown in Equation (27).

Subsequently, a tap coefficient determining circuit 249 solves the normal equations generated for each class at the normal equation adding circuit 248, thereby obtaining tap coefficients for each class, which is supplied to addresses corresponding to each class in the coefficient memory 250. Accordingly, the coefficient memory 250 stores the tap coefficients for each of the classes supplied from the tap coefficient determining circuit 249.

Now, depending on the image data prepared as learning data, there may be a case wherein there is a class regarding which the necessary number of normal equations for obtaining tap coefficients cannot be obtained at the normal equation adding circuit 248, but for such classes, the tap coefficient determining circuit 249 outputs, for example, a default tap coefficient.

Thus, upon tap coefficient sets being obtained regarding the zoom magnification of the range of interest, the control circuit 251 changes the range of interest to another zoom magnification range, and the same processing is repeated with the learning device shown in FIG. 40. Accordingly, the tap coefficient sets corresponding to each of the multiple zoom magnification ranges set by the control circuit 251 are obtained.

Figure 41:
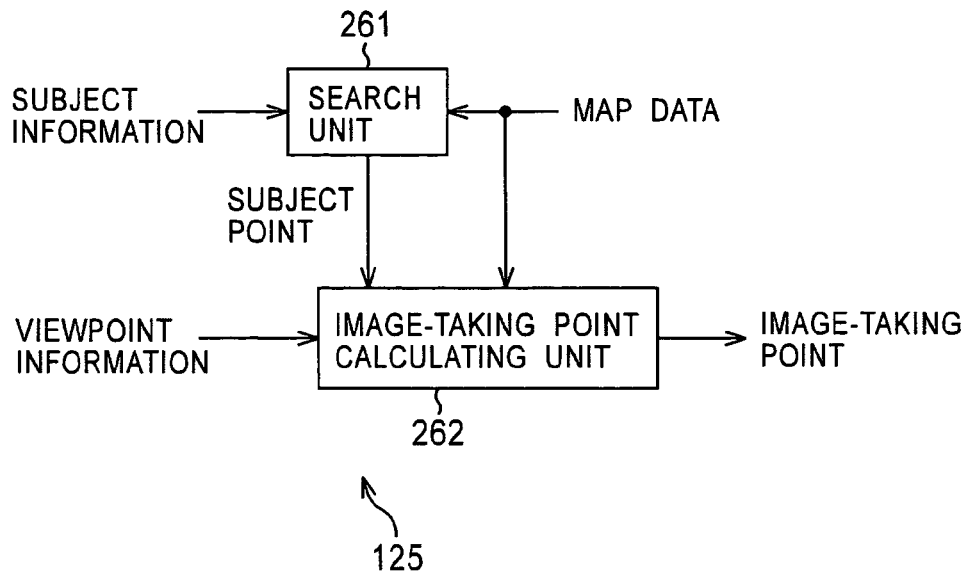
FIG. 41 is a block diagram illustrating an electrical configuration example of a coordinates computing unit 125.

Next, FIG. 41 illustrates a configuration example of the coordinates calculating unit 125 shown in FIG. 26.

The coordinates calculating unit 125 is configured of a search unit 261 and image-taking point calculating unit 262, and calculates image-taking points to serve as the position (coordinates) for taking a desired subject (e.g., latitude and longitude, etc.), in response to request from the control unit 118 (FIG. 26).

That is to say, subject information is supplied to the search unit 261. This subject information is input by, for example, the operating unit 115 being operated by the user, and is supplied to the search unit 261 via the control unit 118. Now, subject information is information for distinguishing a desired subject, and the name of the subject (e.g., "Tokyo Tower", "Diet Building", etc.), address, etc., can be used.

Upon receiving subject information, the search unit 261 makes reference to the map data stored in the map database 124 and searches for the position (coordinates) of the subject distinguished by the subject information thereof (e.g., latitude and longitude, etc.). The search unit 261 then supplies the position of the subject (hereafter referred to as subject point, as appropriate) to the image-taking point calculating unit 262.

Figure 25:
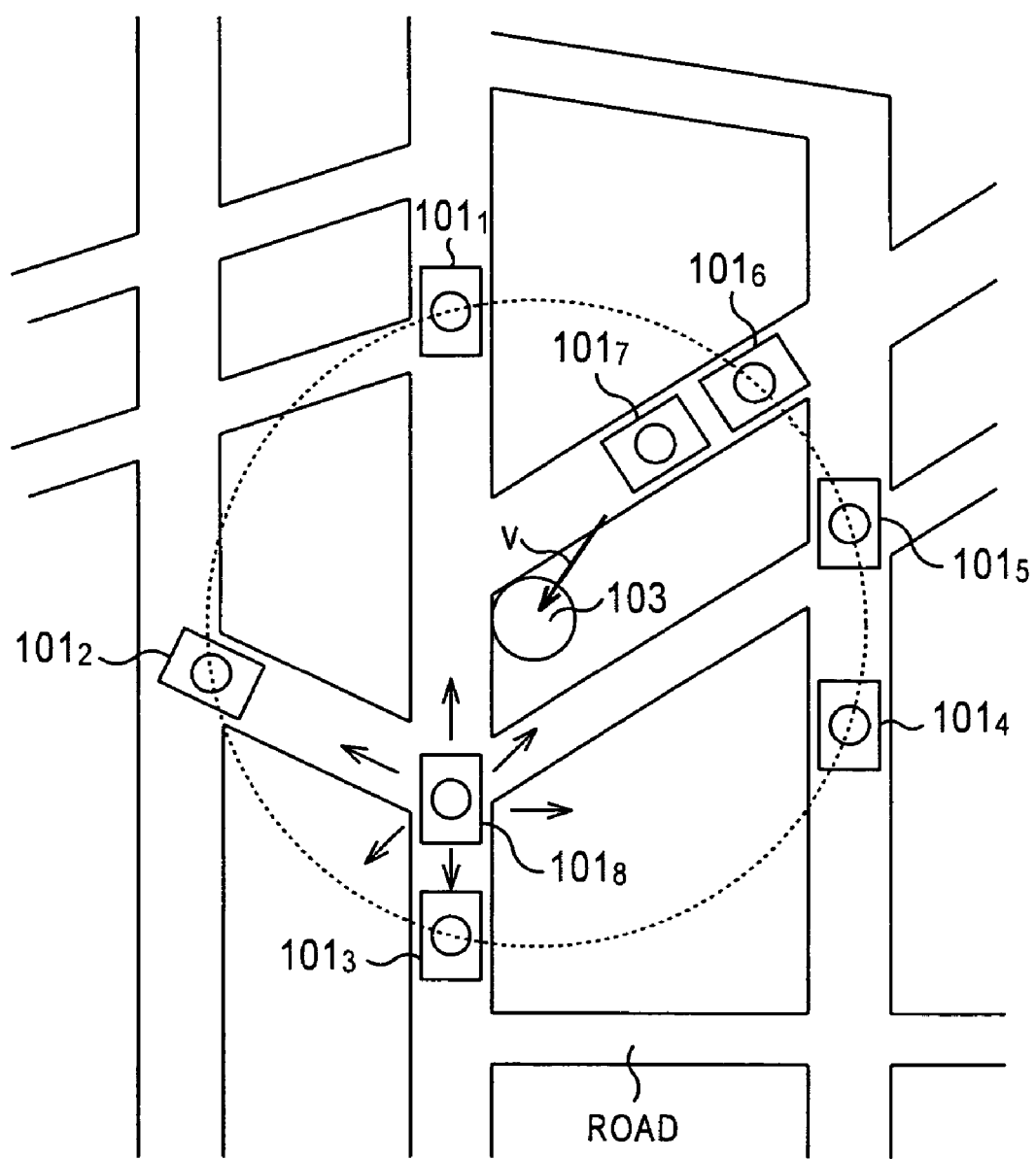
FIG. 25 is a diagram describing the overview of the functions of the SHARN moving entity system.

Here, as described in FIG. 25, the three functions of the first through third functions are realized with the SHARN moving entity system. Of the first through third functions, there is no need to determine the image-taking point for the first function, and the only time that there is the need to determine the image-taking point is a case of realizing the second and third functions.

In the event of realizing the second function, i.e., in the vent of obtaining an image wherein the desired subject is viewed from a desired viewpoint direction v, the image-taking position is determined as follows.

That is to say, in this case, viewpoint information representing the desired viewpoint direction v regarding the desired subject is input by the user operating the operating unit 115.

This viewpoint information is supplied to the image-taking point calculating unit 262 via the control unit 118.

In the event of realizing the second function, the image-taking point calculating unit 262 calculates the image-taking point as a position suitable for taking images of the subject at the position of the subject point from the viewpoint direction v which the viewpoint information represents, from the search unit 261.

That is to say, the image-taking point calculating unit 262 makes reference to the map data stored in the map database 124, and thereby sets the range of a place suitable for taking images of the subject as a so-called doughnut-shaped range (hereafter referred to as suitable range, as appropriate), which is away from the subject point by a distance $R_{p2}$ or more, but closer than a distance $R_{p2}$.

Further, the image-taking point calculating unit 262 detects, of the intersections between line segments from the viewpoint direction v represented by the viewpoint information toward the subject point, and roads or the like over which the moving entity $101_k$ can move, all of those which are within the suitable range, as image-taking point candidates.

The image-taking point calculating unit 262 then selects one arbitrary point from the image-taking point candidates for example, and supplies the selected image-taking point to the control unit 118.

Here, only one position on the viewpoint direction v is taken as an image-taking point for realizing the second function, in order to simplify description, but multiple points on the viewpoint direction v may be taken as image-taking points. Also, examples of methods for selecting one image-taking point from the multiple image-taking point candidates include selecting the closest or farthest from the subject point, and so forth.

Also, in the event of realizing the third function, that is, in the event of obtaining a viewpoint-variable image wherein the desired subject is viewed over which changing the viewing, the image-taking points are obtained as follows.

That is, in the event of realizing the third function, the image-taking point calculating unit 262 makes reference to the map data stored in the map database 124, thereby obtaining a circle which is centered on the subject point supplied from the search unit 261 and which has a radius R suitable for taking images of the subject (e.g., the average of the distances $R_{p1}$ and $R_{p2}$ in FIG. 42, or the like), and obtains the intersections between that circle (perimeter) and roads and the like over which the moving entity $101_k$ is capable of traveling. The image-taking point calculating unit 262 then obtains all of the intersections as image-taking points, and supplies these to the control unit 118.

Now, in the event of obtaining a viewpoint-variable image wherein the subject is viewed over while changing the viewpoints, ideally, images are necessary wherein the subject is being taken from directions 360° around, that is to say, taken from all over.

However, there is no guarantee that all positions from which the subject can be viewed from directions 360° around, can be obtained as intersections between the circle having the radius R centered on the subject point, and the roads and the like over which the moving entity $101_k$ can travel.

That is to say, in the event of taking intersections between the circle having the radius R centered on the subject point, and the roads and the like over which the moving entity $101_k$ can travel as the image-taking points, while image-taking points which are the same distance from the subject point can be obtained, there may be cases wherein the subject cannot be viewed from a certain direction, depending on the state of presence of roads.

Figure 43A:
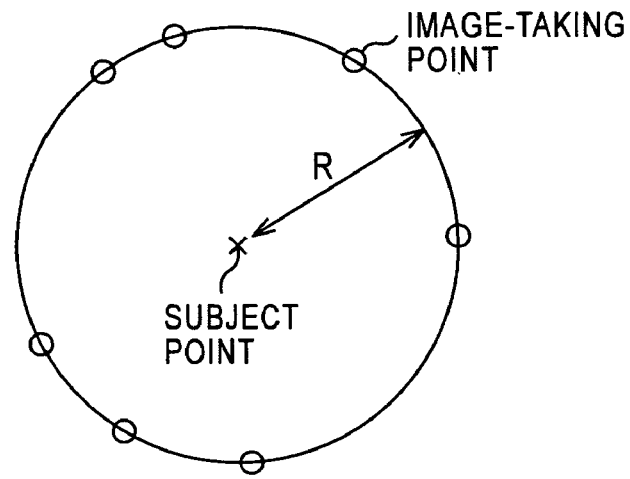
FIG. 43A is a diagram for describing how to obtain image-taking points.
Figure 43B:
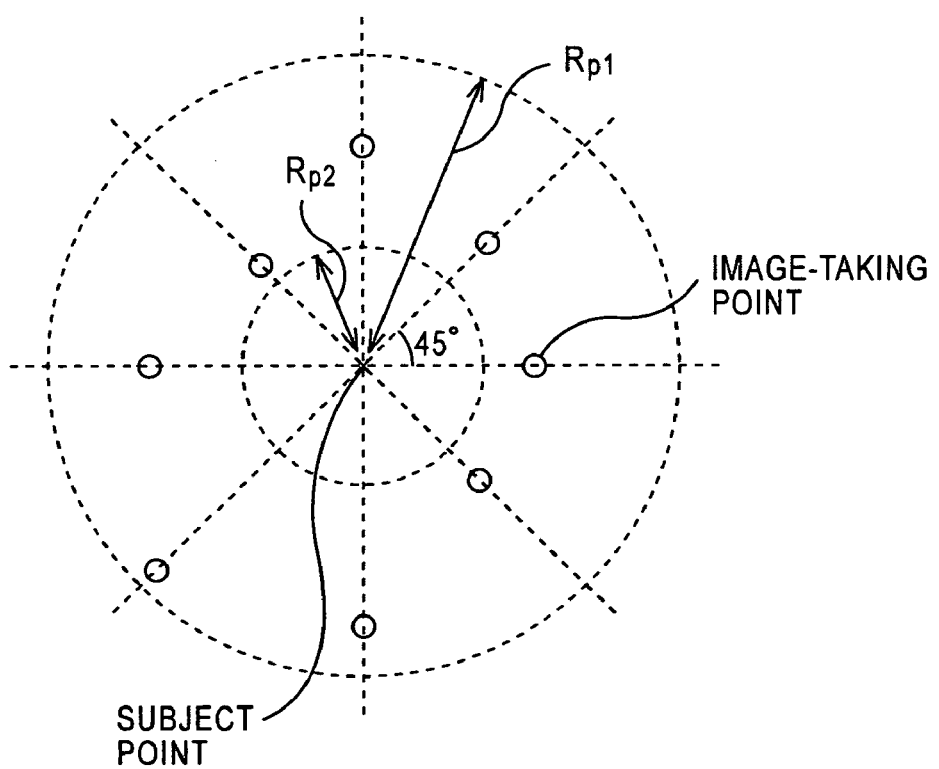
FIG. 43B is a diagram for describing how to obtain image-taking points.

Accordingly, in the event of realizing the third function, the image-taking point calculating unit 262 can obtain the image-taking points as shown in FIG. 43B, for example.

That is, in this case, the image-taking point calculating unit 262 equally divides the directions 360° around the subject point as the center, into several directions. Here, with the embodiment in FIG. 43B, the 360° direction centered on the subject point is equally divided into eight directions which differ by 45° each.

Figure 42:
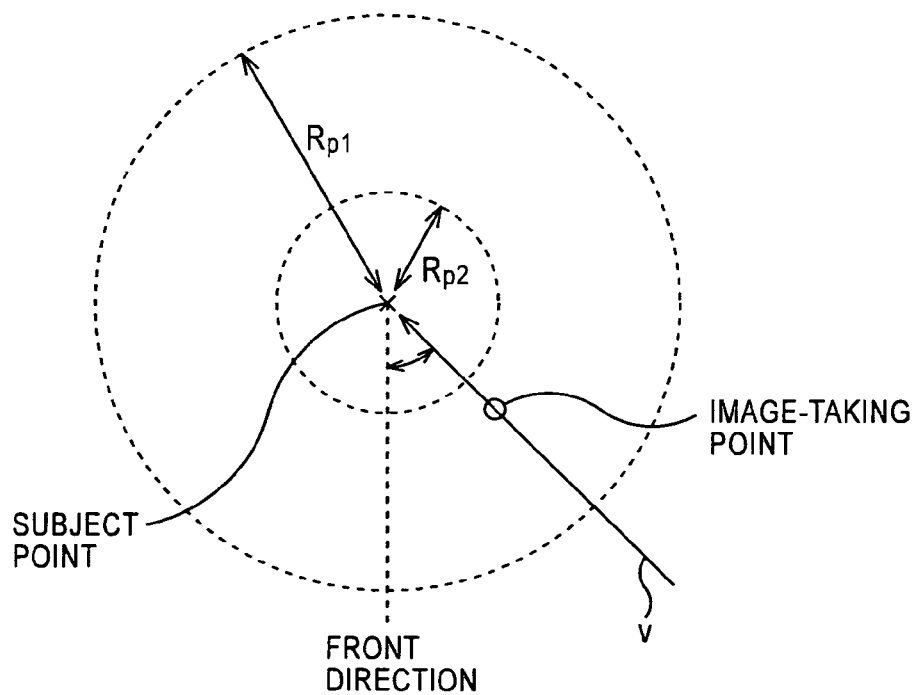
FIG. 42 is a diagram for describing how to obtain image-taking points.

The image-taking point calculating unit 262 then calculates image-taking points in the same way as described in FIG. 42 for the eight directions, with each of the eight directions as viewpoint information. In this case, eight image-taking portions capable of viewing the subject from directions differing 45° each can be obtained. That is, in this case, the distances from the subject point to each image-taking point are generally not the same, but image-taking points whereby the subject can be viewed all over from directions 360° around can be obtained.

Figure 44:
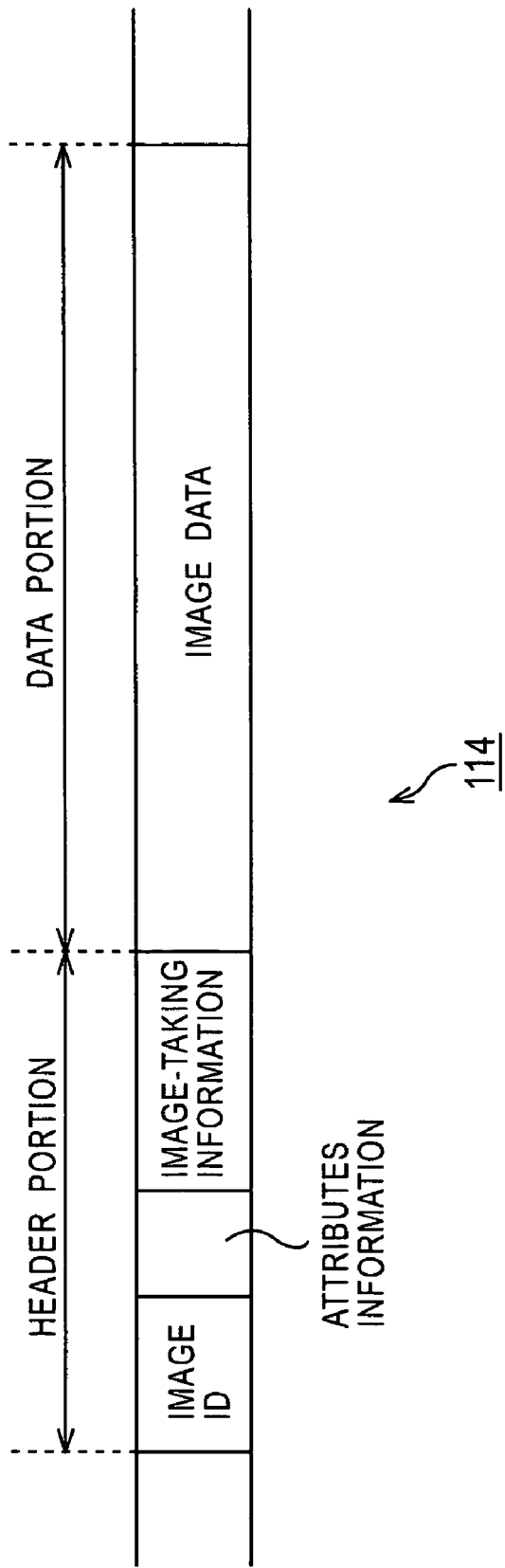
FIG. 44 is a diagram illustrating the storage format of an image database 114.

Next, FIG. 44 illustrates the format of the all-directional image data at the time of being stored in the image database 114 shown in FIG. 26.

In the image database 114, for example, one all-direction image data is managed with a header portion and data portion, as shown in FIG. 44.

The header portion has image ID (Identification) attributes information, image-taking information, and the like, and the data portion has image data (all-directional image data).

The image ID is a unique ID regarding the all-directional image data placed in that data portion, which the control unit 118 registers in the image database 114. As for the image ID, a combination may be used of, for example: the moving entity ID of the moving entity $101_k$ taking the corresponding all-direction image data; the year, month, and date, on which the image was taken; which number in order of images taken on that year, month, and date, the image is, and so forth. Let us say that the control unit 118, for example, stores the moving entity ID of the moving entity $101_k$.

Attributes information represents information of various attributes in the all-directional image data placed in the data portion. Examples of the attributes information include subject information for distinguishing the subject contained in the all-directional image data, the subject point, image-taking point where the all-directional image data was taken, viewpoint information representing the direction of viewing the subject from the image-taking point (viewpoint direction), and so forth. The attributes information is registered in the image database 114 by the control unit 118.

Image-taking information is information relating to settings of the image-taking device 111, output from the image-taking device 111 as described above, and is registered in the image database 114 by the scaling unit 113.

Note that the moving entity $101_k$ is capable of receiving image data taken by the all-directional camera $102_k$ of another moving entity $101_{k'}$, and image data which the moving entity $101_{k'}$ has received from yet another moving entity $101_{k''}$ and registered in the image database 114 thereof (the image database 114 of the moving entity $101_{k'}$), so that in addition to the image data taken with its own all-directional camera $102_k$, image data received from other moving entities $101_{k'}$ is also stored in the image database 114 of the moving entity $101_k$, as described above.

Figure 45:
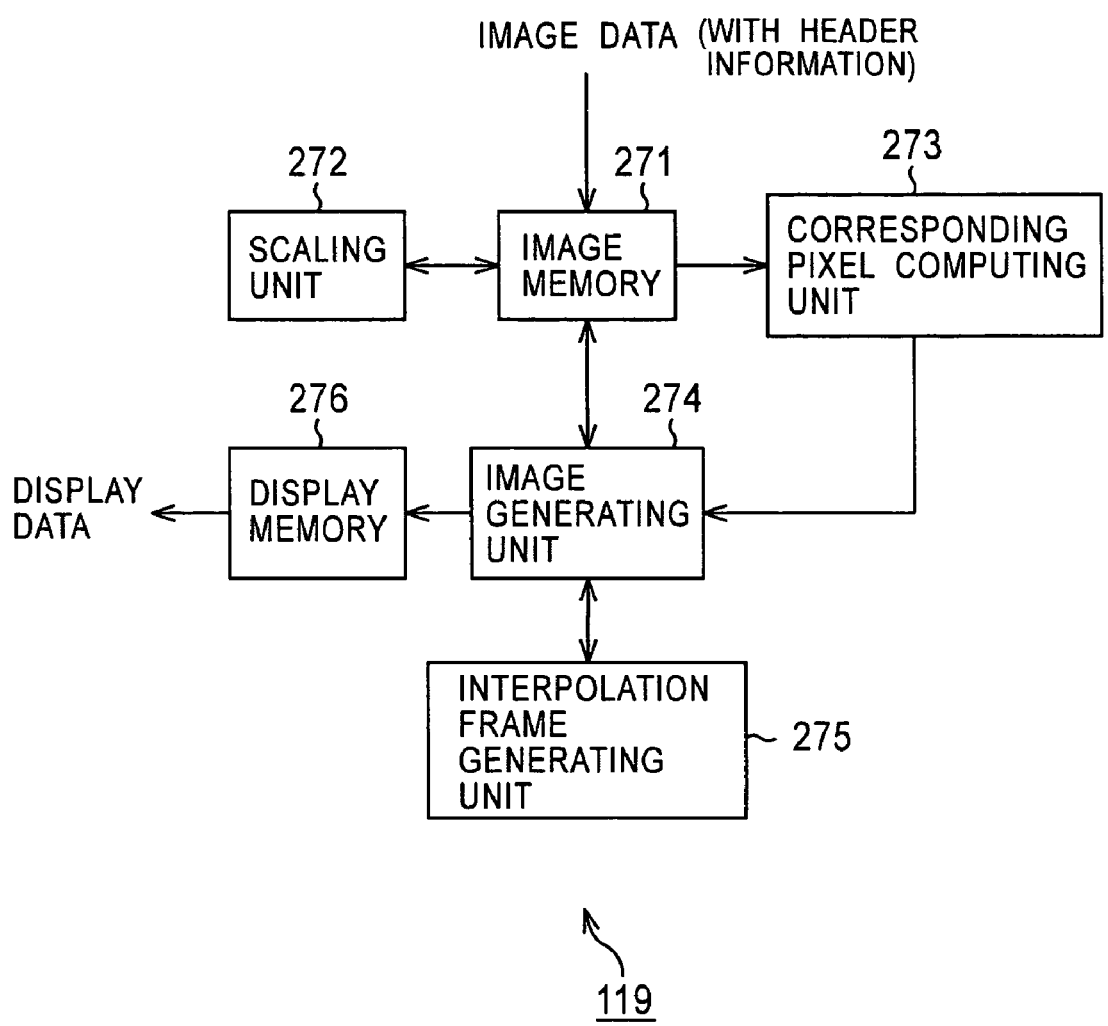
FIG. 45 is a block diagram illustrating an electrical configuration example of a display image altering unit 119.

Next, FIG. 45 illustrates a configuration example of the display image processing unit 119 shown in FIG. 26.

Image data is supplied from the control unit 118 to the image memory 271, and the image memory 271 stores the image data.

Note that information placed in the header portion shown in FIG. 44 regarding the image data (hereafter referred to as header information as appropriate) is supplied to the image memory 271 along with the image data, and the image memory 271 stores the image data along with the header information.

Also, the image memory 271 has storage capacity capable of storing multiple sets of all-directional image data (including header information).

The scaling unit 272 is configured in the same way as the scaling unit 113 in FIG. 26 for example, and enlarges or reduces the image data stored in the image memory 271 according to control by the control unit 118.

That is to say, in the event that the user has instructed enlarging or reducing of the image by operating the operating unit 115, the control unit 118 controls the scaling unit 272 according to the instructions, thereby enlarging or reducing the image data stored in the image memory 271.

Also, in the event that multiple sets of image data are sorted in the image memory 271, the scaling unit 272 enlarges or reduces the size of the subject displayed in multiple sets of image data if necessary, so that the subject is displayed the same size.

That is with the third function, multiple sets of image data taking the same subject from multiple directions as described in FIG. 43 is stored in the image memory 271, in order to generate a viewpoint-variable image wherein the desired subject is viewed over while changing the viewpoints.

In the event that the multiple sets of image data taking the same subject from multiple directions (hereafter referred to as different-direction image data) have been taken from image-taking points distanced from the subject point by the same distance, as shown in FIG. 34A, even if the zoom magnification at the time of image-taking at each image-taking point differs, this is converted into image data with the same zoom magnification (fixed magnification) by the scaling unit 113, and accordingly, the size of the subject in the different-direction image data is the same.

However, in the event that the multiple different-direction image data sets have been taken from image-taking points distanced from the subject point by different distances as shown in FIG. 43B, converting the zoom magnification of the multiple different-direction image data sets at the scaling unit 113 does not make the size of the subject in the different-direction image data sets the same size. That is to say, the size of the subject in the different-direction image data sets depends on how far the image-taking points where the different-direction image data has been taken are from the subject point.

Accordingly, in the event that multiple different-direction image data sets have been stored in the image memory 271, the scaling unit 272 enlarges or reduces the different-direction image data stored in the image memory 271 so that the subject in the different-direction image data is the same size (scales).

Note that in this case, the enlargement ratio or reduction ratio of each of the different-direction image data sets is determined such that the size (scale) of the same subject in the multiple different-direction image data sets stored in the image memory 271 is the same, based on the distance between the image-taking points and the subject point, contained in the header thereof.

Thus, upon enlarging or reducing the image data stored in the image memory 271, the scaling unit 272 writes the enlarged or reduced image data to the image memory 271, by overwriting the original image data, for example.

A corresponding pixel computing unit 273 detects corresponding pixels in the multiple different-direction image data sets stored in the image memory 271, in the event of realizing the third function under control of the control unit 118.

That is, the corresponding pixel computing unit 273 makes reference to the viewpoint information within the header information of each of the sets of the different-direction image data stored in the image memory 271, thereby recognizing the order in which the viewpoint directions which the viewpoint information represents are clockwise or counter-clockwise with a certain direction as the reference direction (hereafter referred to as viewpoint direction order, as appropriate). Further, the corresponding pixel computing unit 273 detects which pixels of the subject in the i'th different-direction image data that each pixel of the subject in the i+1'th different-direction image data correspond to.

Note that this corresponding pixel detection can be performed using, for example, so-called block matching or the like.

Upon detecting the correlation of pixels regarding the multiple sets of different-direction image data stored in the image memory 271, the corresponding pixel computing unit 273 supplies the correlation of the pixels to the image generating unit 274.

In the event of realizing the first function or second function, the image generating unit 274 reads out the image data stored in the image memory 271, and supplies this to the display memory 276.

Also, in the event of realizing the third function, the image generating unit 274 uses the multiple different-direction image data sets stored in the image memory 271 to generate the viewpoint-variable image data viewing the subject over while changing the viewpoint in the clockwise or counter-clockwise direction.

That is to say, the image generating unit 274 generates viewpoint-variable image data as moving image data which would have been taken if the subject had been taken while changing the viewpoint in the clockwise or counter-clockwise direction, by arranging the different-direction image data in order of viewpoint direction as moving image frames, while positioning in the spatial direction so as to correlate corresponding pixels, based on the correlation of pixels supplied from the corresponding pixel computing unit 273.

Note that in the event that the viewpoint-variable image data is generated as moving image data by positioning the multiple different-direction image data sets stored in the image memory 271 sequentially as the first frame, second frame . . . , in the viewpoint direction order, the viewpoint-variable image data may not become a smooth moving picture depending on the number of sets of different-direction image data and the density of image-taking points.

Accordingly, the image generating unit 274 is arranged to array the multiple different-direction image data sets stored in the image memory 271 in an order of frames corresponding to the viewpoint direction.

That is to say, in the event of attempting to generate viewpoint-variable image data wherein the subject is circled one time (rotated 360°) in three seconds, with a frame rate of 30 frames/second, for example, the viewpoint-variable image data needs to be configured of 90 frames (=30 frames/second×3 seconds), and further, the change in the viewpoint direction between adjacent frames in the viewpoint-variable image data needs to be 4° (=360°/90 frames).

Accordingly, in this case, the image generating unit 274 positions the different-direction image data closest to 4×(i−1)° in the viewpoint direction, as the i'th frame.

However, in this case, there may be frames regarding which different-direction image data is not placed. Accordingly, the image generating unit 274 performs interpolation for the frames regarding which no different-direction image data is placed (hereafter referred to as unplaced frames, as appropriate) using frames regarding which different-direction image data is placed (hereafter referred to as placed frames, as appropriate), by controlling an interpolation frame generating unit 275, thereby generating image data to be placed in the unplaced frame. That is to say, the interpolation frame generating unit 275 performs interpolation between a placed frame which is closest to the unplaced frame and is ahead time-wise, and a placed frame which follows time-wise, thereby generating image data for the unplaced frame. Note that interpolation for this unplaced frame is performed taking into consideration the time-wise distance from the unplaced frame to the placed frames ahead or following time-wise, that are used for this interpolation.

Now, besides performing simple interpolation using placed frame image data as described above, so as to generate image data for unplaced frames, the interpolation frame generating unit 275 is also capable of generating unplaced frame image data by performing class classification adaptation processing using placed frame image data, for example.

The image generating unit 274 performs necessary interpolation as described above, and finally completes the viewpoint-variable image data as moving picture data, and then supplies the viewpoint-variable image data to the display memory 276 where it is stored.

The image data sorted in the display memory 276 is supplied to and displayed at the display unit 122 (FIG. 26).

Next, processing which the moving entity $101_k$ shown in FIG. 26 performs will be described.

Note that the processing performed by the moving entity $101_k$ can be generally divided into processing wherein the moving entity $101_k$ serves as a master moving entity as if it were (hereafter referred to as master moving entity) and other moving entities $101_{k'}$ serve as slave moving entities as if it were (hereafter referred to as slave moving entities), so as to process various requests with regard to the moving entity $101_{k'}$ serving as the slave moving entity, and processing wherein the other moving entity $101_{k'}$ serves as the master moving entity and processing is performed according to the requests of the master moving entity.

Accordingly, a description will be made wherein the moving entity $101_k$ serves as the master moving entity and the moving entity $101_{k'}$ serves as a slave moving entity, with regard to the processing which the moving entity $101_k$ serving as the master moving entity performs (master moving entity processing) and processing which the moving entity $101_{k'}$ serving as the slave moving entity performs (slave moving entity processing).

Figure 46:
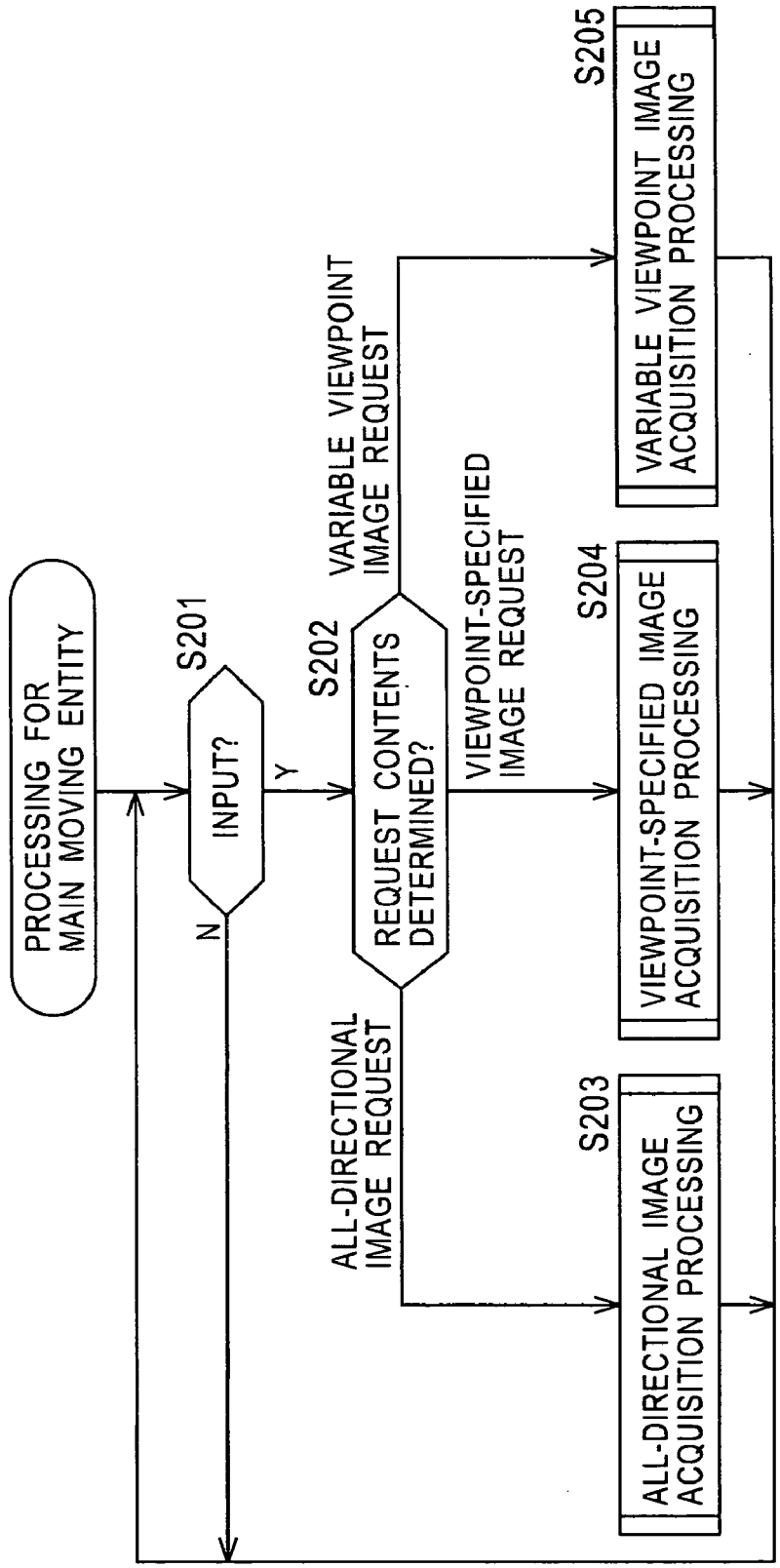
FIG. 46 is a flowchart describing the processing of a main moving entity.

First, processing of the master moving entity will be described with reference to the flowchart shown in FIG. 46.

First, to begin with, in step S201, the control unit 118 determines whether or not there has been some sort of input by the user $U_k$ operating the operating unit 115. In the event that determination is made in step S201 that there has been no input, the flow returns to step S201.

Also, in the event that there has been determined to have been some input from the user $U_k$ in step S201, the flow proceeds to step s202, where the control unit 118 determines what the input from the user $U_k$ requests.

In step S202, in the event that the input from the user $U_k$ is determined to be requesting all-directional image data, the flow proceeds to step S203, the later-described all-directional image acquiring processing is performed, and the flow returns to step S201.

Also, in the event that determination is made in step S202 that the input from the user $U_k$ requests image data wherein a desired subject has been taken from a desired viewpoint direction (hereafter referred to as viewpoint-specified image data, as appropriate), the flow proceeds to step S204, the later-described viewpoint-specified image acquiring processing is performed, and the flow returns to step S201.

Further, in the event that determination is made in step S202 that the input from the user $U_k$ requests viewpoint-variable image data, the flow proceeds to step S205, where the later-described viewpoint-variable image acquiring processing is performing, and the flow returns to step S201.

Note that the first through third functions correspond to the all-directional image acquiring processing in step S203, the viewpoint-specified image acquiring processing in step S204, and the viewpoint-variable image acquiring processing in step S205, respectively.

Figure 47:
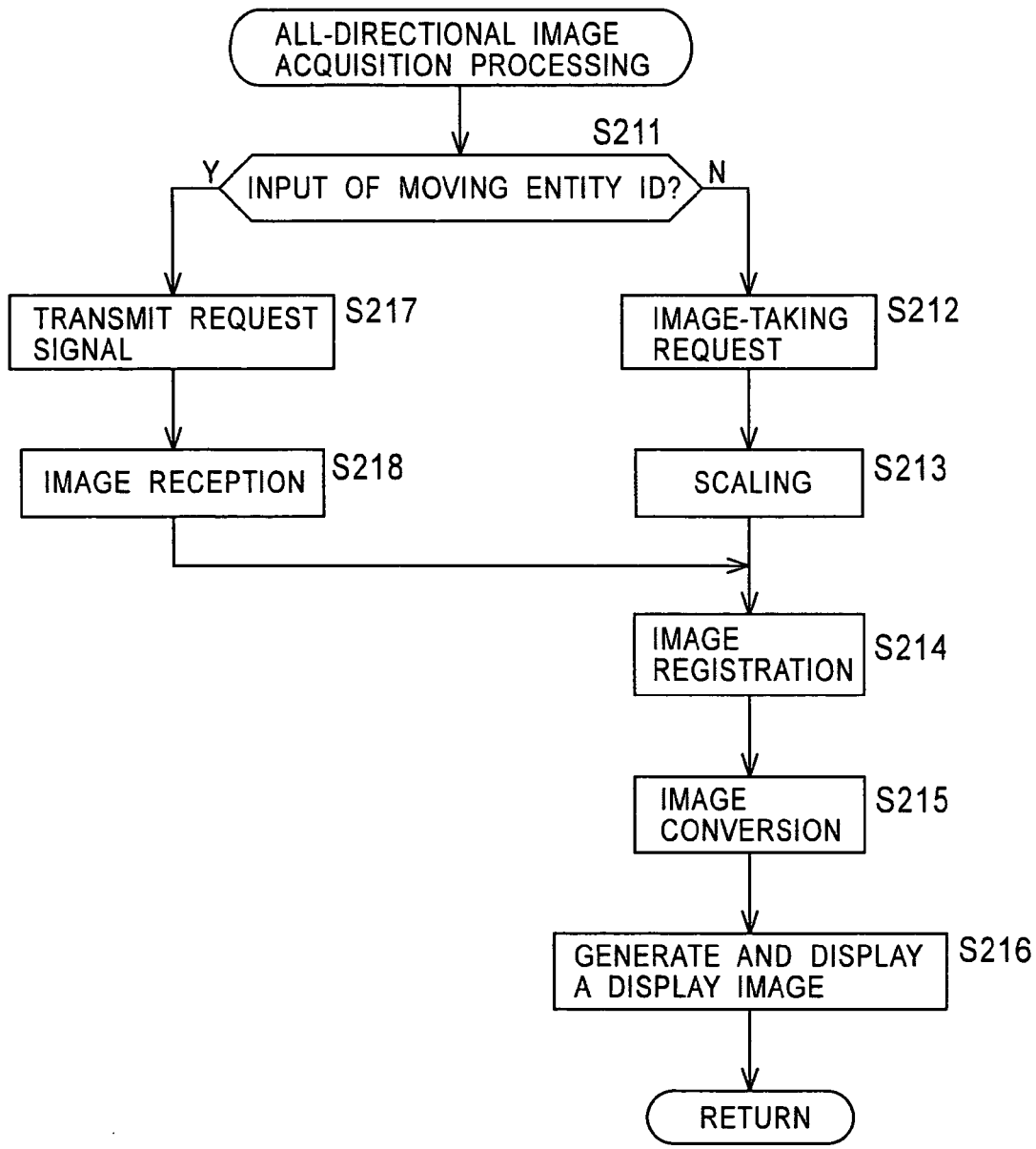
FIG. 47 is a flowchart describing all-directional image acquiring processing.

Next, the all-directional image acquiring processing in step S203 in FIG. 46 will be described with reference to the flowchart in FIG. 47.

In the all-directional image acquiring processing, first, to start with, in step S211, the control unit 118 determines whether or not there has been input of a moving entity ID identifying another moving entity (slave moving entity) by the user $U_k$ operating the operating unit 115.

In step S211, in the event that determination is made that there has been no input of a moving entity ID by the user $U_k$, the flow proceeds to step S212, where the control unit 118 makes an image-taking request to the image-taking device 111 of the all-directional camera $102_k$. The image-taking device 111 takes all-directional image data in response to the request from the control unit 118, and supplies this to the scaling unit 113 via the A/D converting unit 112.

Upon receiving supply of the all-direction image data from the all-directional camera $102_k$, the scaling unit 113 converts (scales) the all-directional image data into the fixed-magnification all-directional image data in step S213, the flow proceeds to step S214, and is supplied to and registered in the image database 114.

Subsequently, the flow proceeds to step S215, where the control unit 118 reads out the all-directional image data registered in the image database 114 in the immediately previous step S214, and supplies this to the image conversion unit 127, where image conversion for removing distortion in the all-directional image data is performed.

The flow then proceeds to step S216, where the control unit 118 supplies the image-converted (post distortion-removal) all-directional image data to the display image processing unit 119, where the display data to be displayed on the display unit 122 (hereafter referred to as display data as appropriate) is generated.

That is to say, in this case, the all-directional image data from the control unit 118 is sorted in the image memory 271 at the display image processing unit 119 (FIG. 45). The all-directional image data stored in the image memory 271 is subjected to scaling adjustment at the scaling unit 272 as necessary, and is supplied to the display memory 276 via the image generating unit 274.

The display memory 276 stores the all-directional image data supplied via the image generating unit 274 as display data, and supplies this to the display unit 122.

Accordingly, in step S216, the all-directional image data is displayed on the display unit 122, and the all-directional image data acquiring processing ends.

Accordingly, in this case, the all-directional image data (still images) obtained on site by the master moving entity is displayed on the display unit 122.

On the other hand, in step S211, in the event that determination is made that there has been input of a moving entity ID by the user $U_k$, the flow proceeds to step S217, and the control unit 118 controls the transmission unit 116 so as to transmit request signals requesting image data along with the moving entity ID which the user $U_k$ has input included therein.

In this case, as described later, the moving entity (slave moving entity) distinguished by the moving entity ID included in the request signal takes the all-directional image data on site, and transmits this to the moving entity $101_k$ which is the master moving entity, so in step S218, the reception unit 117 awaits and receives transmission of the all-directional image data. Note that the slave moving entity transmits the all-directional image data with the same format as the storage format of the image database 114 shown in FIG. 44.

Subsequently, the flow proceeds to step S214, where the all-directional image data received at the reception unit 117 is supplied to and registered in the image database 114. Hereafter, the same processing as described above is performed in steps S215 and S216, and the all-directional image data acquiring processing ends.

Accordingly, in this case, the all-directional image data (still images) taken on site by the slave moving entity identified by the moving entity ID input by the user $U_k$ is displayed on the display unit 122.

Next, viewpoint-specified image obtaining processing in step S204 of FIG. 46 will be described with reference to the flowchart in FIG. 48.

First, to begin with, in step S211, the control unit 118 controls the display unit 122 so as to display a message requesting subject information and viewpoint information input, the flow proceeds to step S222, and the control unit 118 determines whether the user $U_k$ has input the subject information and viewpoint information by operating the operating unit 115.

In step S222, in the event that determination is made that the subject information and viewpoint information has not been input, the flow returns to step S211, and the user is requested to input the subject information and viewpoint information.

Also, in step S222, in the vent that determination has been made that there has been input of subject information and viewpoint information, the flow proceeds to step S223, where the control unit 118 supplies the subject information and viewpoint information to the coordinates computing unit 125, so as to calculate the image-taking point. That is to say, the coordinates computing unit 125 obtains one image-taking point in the way described with FIG. 42, and supplies this to the control unit 118.

The control unit 118 stores the image-taking point from the coordinates computing unit 125 to the storage unit 121, the flow proceeds to step S224, where the image database 114 is referred to, thereby determining whether all-directional image data including the subject distinguished by the subject information input by the user $U_k$ has been already registered for the image-taking point obtained in step S223. this determination can be made by referring to the information (header information) of the header portion (FIG. 44) in the image database 114.

In step S224, in the event that determination is made that all-directional image data including the subject distinguished by the subject information input by the user $U_k$ has been already registered in the image database 114 for the image-taking point obtained in step S223, i.e., in the event that all-directional image data viewing the subject identified by the subject information which the user $U_k$ has input from the viewpoint direction which the viewpoint information also input by the user $U_k$ represents has been taken by itself in the past or has been received from another moving entity has already been registered in the image database 114, the flow proceeds to step S225, where the control unit 118 reads out the all-directional image data from the image database 114, and the flow proceeds to step S232.

Also, in step S224, in the event that determination is made that all-directional image data including the subject distinguished by the subject information input by the user $U_k$ has not been registered in the image database 114 for the image-taking point obtained in step S223, the flow proceeds to step S226, and the comparing unit 120 determines whether or not the current position matches the image-taking point stored in the storage unit 121.

That is, in step S226, determination is made by the comparing unit 120 regarding whether or not the current location detected by the position detecting unit 123 matches the image-taking point stored in the storage unit 121 in step S223.

In the event that determination is made in step S226 that the current position matches the image-taking position stored in the storage unit 121, i.e., in the event that the master moving entity itself is situated at the image-taking position, the flow proceeds to step S227, and the control unit 118 makes an image-taking request to the image-taking device 111 of the all-directional camera $102_k$. The image-taking device 111 takes the all-directional image in response to the request from the control unit 118, and supplies this to the scaling unit 113 via the A/D converting unit 112.

Upon receiving supply of the all-directional image data, the scaling unit 113 converts (scales) the all-directional image data into all-directional image data of a fixed magnification in step S228, the flow proceeds to step S229, and this is supplied to and registered in the image database 114. The control unit 118 reads out the all-directional image data registered in the image database 114 in step S229, and the flow proceeds to step S232.

On the other hand, in step S226, in the event that determination is made that the current location does not match the image-taking point stored in the storage unit 121, the flow proceeds to step S230, where the control unit 118 controls the transmission unit 116 so as to transmit a request signal requesting image data to the image-taking points obtained in step S233, with the image-taking point obtained in step S233 included therein.

In this case, as described later, a moving entity (slave moving entity) located at the image-taking point contained in the request signal takes the all-directional image data at the current location (i.e., image-taking point) or the like and transmits this to the moving entity $101_k$ which is the master moving entity, so in step S231, the reception unit 117 awaits and receives transmission of the all-directional image data.

In this case, moving entity processing shown in FIG. 50 described later is performed for multiple moving entities, so it is conceivable that the same all-directional image data taken from the image-taking point contained in the request signal may be transmitted, and in the event that the same all-directional image data is transmitted from multiple moving entities in this way, the reception unit 117 selects one of the same multiple all-directional image data, for example. This is the same for step S250 in FIG. 49 described later, as well.

Subsequently, the flow proceeds to step S229, where the all-directional image data received by the reception unit 117 is supplied to and registered in the image database 114. the control unit 118 reads out the all-directional image data registered in the image database 114 in step S229, and the flow proceeds to step S232.

In step S232, the control unit 118 supplies the all-directional image data read out from the image database 114, i.e., the viewpoint-specified image data which is all-directional image data viewing the subject distinguished by the subject information input by the user $U_k$ from the viewpoint direction which the viewpoint information also input by the user $U_k$ represents, to the cropping unit 126 along with the header information thereof, so that the portion of the viewpoint-specified image data containing the subject distinguished by the subject information input by the user $U_k$ is cropped out.

That is to say, the portion of the all-directional image data which is the viewpoint-specified image data containing the subject can be recognized from the subject point and image-taking point in the header information. The cropping unit 126 crops out a region of the all-directional image data which is the viewpoint-specified image data containing the subject, of a region surrounded by arcs $F_{C1}$ and $F_{C2}$ of circles centered on the center point C1 and straight lines $L_{C1}$ and $L_{C2}$ passing through the center point C1, and the image data of the region that has been cropped out (hereafter referred to as cropped image data, as appropriate) is supplied to the control unit 118.

Upon receiving the cropped image data, the control unit 118 proceeds to step S233 and supplies the cropped image data to the image converting unit 127, where image conversion is performed to remove the distortion.

The flow then proceeds to step S234, where the control unit 118 supplies the converted (post distortion removal) cropped image data to the display image processing unit 119, and generates display data.

That is to say, in this case, at the display image processing unit 119 (FIG. 45), the cropped image data from the control unit 118 is stored in the image memory 271. The cropped image data stored in the image memory 271 is subjected to scale adjustment in the scaling unit 272 as necessary, and is supplied to the display memory 276 via the image generating unit 274.

The display memory 276 stores the cropped image data supplied via the image generating unit 274 as display data, and supplies this to the display unit 122. Accordingly, in step S234, the display unit 122 displays the cropped image data, and the viewpoint-specified image acquiring processing ends.

Accordingly, in this case, the display unit 122 displays images (still images) of the subject desired by the user, taken from the viewpoint direction desired by the user.

Next, the viewpoint-variable image acquiring processing in step S205 of FIG. 46 will be described with reference to the flowchart in FIG. 49.

First, to start with, in step S241, the control unit 118 controls the display unit 122 so as to display a message requesting input of the subject information, an the flow proceeds to step S242, where the control unit 118 determines whether or not the user $U_k$ has input subject information by operating the operating unit 115.

In step S242, in the event that determination is made that subject information has not been input, the flow returns to step S241, and input of the subject information is requested for the user again.

Also, in step S242, in the event that determination is made that there has been input of subject information, the flow proceeds to step S243, where the control unit 118 supplies the subject information to the coordinates computing unit 125 so as to calculate the image-taking point. That is to say, in this case, the coordinates computing unit 125 obtains the multiple image-taking points for taking the subject distinguished by the subject information as described in FIG. 43, and supplies these to the control unit 118.

The control unit 118 stores the multiple image-taking points from the coordinates computing unit 125 to the storage unit 121 where they are stored, the flow proceeds to step S244, and reference is made to the image database 114, whereby determination is made regarding whether or not there is an image-taking point of the subject distinguished by the subject information, of the multiple-image taking points stored in the storage unit 121, already registered in the image database 114.

In the event that determination is made in step S244 that there is an image-taking point of the subject distinguished by the subject information, of the multiple-image taking points stored in the storage unit 121, already registered in the image database 114, i.e., in the event that there is all-directional image data taken of the subject distinguished by the subject information from an image-taking point stored in the storage unit, already registered in the image database 114, the flow proceeds to step S245, where the control unit 118 reads out the all-directional image data from the image database 114, and the flow proceeds to step S246.

In step S246, the control unit 118 supplies the all-directional image data read out from the image database 114 to the cropping unit 126 along with the header information thereof, so that the portion of the all-directional image data containing the subject distinguished by the subject information input by the user $U_k$ is cropped out.

That is to say, as described above, the portion of the all-directional image data containing the subject can be recognizes from the subject point and image-taking point in the header information, so the cropping unit 126 crops out the portion of image data of the all-directional image data containing the subject, and the image data of the region that has been consequently cropped out (including header information) is supplied to the control unit 118.

The control unit 118 temporarily stores the image data supplied in this way from the cropping unit 126 in internal memory (not shown), and the flow proceeds to step S247.

In step S247, the control unit 118 deletes those of the multiple image-taking points stored in the storage unit 121 which match the image-taking point of the all-directional image data read out from the image database 114 in step S245, and the flow proceeds to step S248.

Accordingly, the storage unit 121 stores only image-taking points in the viewpoint directions in which all-directional image data has not been obtained regarding the subject distinguished by the subject information input by the user $U_k$.

Note that in the event that there are two or more of the multiple image-taking points stored in the storage unit 121 which have been already registered in the image database 114 as image-taking points of the subject distinguished by the subject information, the processing in the above-described steps S245 through S247 is performed for the two or more image-taking points already registered.

On the other hand, in the event that determination is made in step S244 that here are none of the multiple image-taking points stored in the storage unit 121 which have been already registered in the image database 114 as image-taking points of the subject distinguished by the subject information, i.e., in the event that there is no all-directional image data containing the subject distinguished by the subject information, taken from the image-taking points stored in the storage unit 121, registered in the image database 114, the flow proceeds to step S248, where the control unit 118 controls the transmission unit 116 so as to transmit a request signal requesting image data along with the image-taking points stored in the storage unit 121, and the flow proceeds to step S249.

In step S249, the reception unit 117 determines whether all-directional image data which has been taken at one of the image-taking points contained in the request signal has been transmitted from a moving entity (slave moving entity) in response to the request signal transmitted in step S248, and in the event that determination is made that this has been transmitted, the flow proceeds to step S250, where the reception unit 117 receives the all-directional image data. The reception unit 117 then proceeds to step S254, supplies the all-directional image data received in step S250 to the image database 114 where it is registered, and the flow proceeds to step S255.

Figure 48:
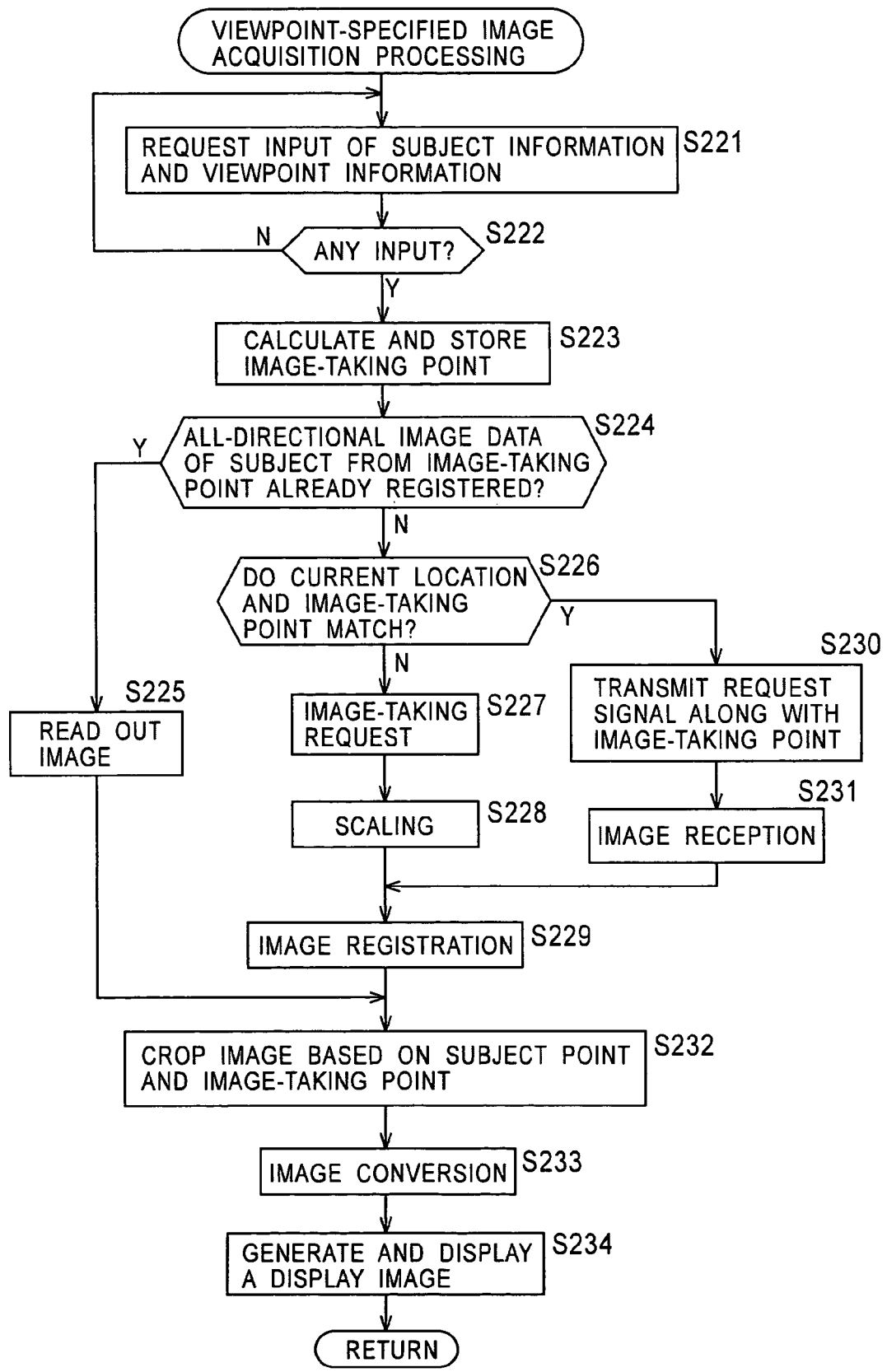
FIG. 48 is a flowchart describing viewpoint-specified image acquiring processing.

On the other hand, in the event that determination is made in step S249 that no all-directional image data has been transmitted from a moving entity (slave moving entity), the flow proceeds to step S251, where the comparing unit 120 determines whether or not the current position matches any of the image-taking points stored in the storage unit 121, in the same way as step S226 in FIG. 48.

In step S251, in the event that determination is made that the current location does not match any of the image-taking points stored in the storage unit 121, the flow skips the step S252 through S256 and proceeds to step S257.

Also, in the event that determination is made in step S251 that the current position matches one of the image-taking positions stored in the storage unit 121, i.e., in the event that the master moving entity itself is situated at an image-taking position, the flow proceeds to step S252, and the control unit 118 makes an image-taking request to the image-taking device 111 of the all-directional camera $102_k$. The image-taking device 111 takes the all-directional image in response to the request from the control unit 118, and supplies this to the scaling unit 113 via the A/D converting unit 112.

Upon receiving supply of the all-directional image data, the scaling unit 113 converts (scales) the all-directional image data into all-directional image data of a fixed magnification in step S253, the flow proceeds to step S254, and this is supplied to and registered. in the image database 114, and the flow proceeds to step S255.

In step S255, the control unit 118 deletes those of the multiple image-taking points stored in the storage unit 121 which match the image-taking points of the all-directional image data stored in the image database 114 in step S254, and proceeds to step S256.

In step S256, the control unit 118 reads out the all-directional image data registered in the image database 114 in step S254, and supplies this to the cropping unit 126 along with the header information thereof, in the same way as with step S246. Accordingly, the portion of the all-directional image data containing the subject distinguished by the subject information input by the user $U_k$ is cropped out by the cropping unit 126, based on the header information from the control unit 118. The cropping unit 126 then supplies the image data of the region that has been consequently cropped out to the control unit 118, and the control unit 118 temporarily stores the image data supplied from the cropping unit 126 in internal memory, and the flow proceeds to step S257.

In step S257, the control unit 118 determines whether or not an image taking point is stored in the storage unit, and whether or not a predetermined amount of time has elapsed following transmitting the request signal in step S248. In step S257, in the event that determination is made that an image-taking point is registered in the storage unit 121, and that the predetermined amount of time has not elapsed since transmitting the request signal, the flow returns to step S249, and the same processing is repeated.

Also, in step S257, in the event that determination is made that there is no image-taking point registered in the storage unit 121, or that the predetermined amount of time has elapsed since transmitting the request signal, that is to say, in the event that the all-directional image data taken of the subject distinguished by the subject information which the user $U_k$ has input, from all of the multiple image-taking points obtained in step S243, or such all-directional image data has not been obtained following elapsing of the predetermined amount of time following transmitting the request signal, the flow proceeds to step S258, where the control unit 118 clears the stored contents of the storage unit 121, and the flow proceeds to step S259.

In step S259, the control unit 118 supplies all of the cropped image data stored in the internal memory to the image converting unit 127, so that image conversion to remove the distortion thereof is performed.

The flow then proceeds to step S260, where the control unit 118 supplies the cropped image data following image conversion (after distortion removal) to the display image processing unit 119, so as to generate display data.

That is to say, in this case, with the display image processing unit 119 (FIG. 45), the cropped image data supplied from the control unit 118 is stored at the image memory 271 as the above-described different-direction image data. The different-direction image data stored in the image memory 271 has the scaling thereof adjusted at the scaling unit 272 as necessary.

Then, the corresponding pixel computing unit 273 detects the correlation of pixels with regard to the different-direction image data stored in the image memory 271 in the same way as describe above, and supplies to the image generating unit 274.

The image generating unit 274 generates viewpoint-variable image data, i.e., data changing the viewpoint in the clockwise or counter-clockwise direction, using the different-direction image data stored in the image memory 271, while making reference to the correlation of the pixels from the corresponding pixel computing unit 273, thereby generating image data taking the subject distinguished by the subject information which the user $U_k$ has input, and supplies this as display data to the display memory 276.

The display memory 276 stores the viewpoint-variable image data supplied via the image generating unit 274 as display data, and supplies this to the display unit 122. Accordingly, in step S260 the viewpoint-variable image data which is moving picture data is displayed on the display unit 122, and the viewpoint-variable image acquiring processing ends.

Accordingly, in this case, the display unit 122 displays a moving picture which would have been taken if the subject desired by the user had been taken while circling the perimeter thereof.

Note that in the image generating unit 274 of the display image processing unit 119 (FIG. 45), in the event that viewpoint-variable image data is generated using the different-direction image data stored in the image memory 271, image data to be placed in unplaced frames is generated at the interpolation frame generating unit 275 for the frames making up the moving picture serving as the viewpoint-variable image data where the different-direction image data has not been placed (unplaced frames), as described with FIG. 45.

Accordingly, the viewpoint-variable image is smoother (has higher resolution in the time direction) the fewer the number of unplaced frames is, meaning that the more sets of different-direction image data can be collected, the more the image quality of the viewpoint-variable image is improved.

Next, the processing of the slave moving entity will be described with reference to FIG. 50.

With the processing of the slave moving entity, in step S271, the reception unit 117 determines whether or not a request signal has been transmitted from the master moving entity which is another moving entity, and in the event that determination is made that there has been no transmission, the flow returns to step S271.

In the event that determination is made in step S271 that a request signal has been transmitted, the reception unit 117 receives the request signal which is supplied to the control unit 118, and the flow proceeds to step S272.

In step S272, the control unit 118 determines whether or not a moving entity Id is contained in the request signal from the reception unit 117, and in the event that determination is made that this is contained, the flow proceeds to step S273.

In step S273, the control unit 118 determines whether or not the moving entity ID contained in the request signal matches its own moving entity ID. Now, the control unit 118 stores the own moving entity ID in internal memory, for example.

In step S273, in the event that determination is made that the moving entity ID contained in the request signal does not match the own moving entity ID, the flow returns to step S271, and subsequently, the same processing is repeated.

Also, in step S273, in the event that determination is made that the moving entity ID contained in the request signal matches the own moving entity ID, the flow proceeds to step S274, where the control unit 118 performs a request for image-taking to the image-taking device 111. The image-taking device 111 takes the all-directional image data in response to the request from the control unit 118, and supplies this to the scaling unit 113 via the A/D converting unit 112.

Upon receiving supply of the all-directional image data, the scaling unit 113 converts (scales) the all-directional image data into all-directional image data of a fixed magnification in step S275, the flow proceeds to step S276, and this is supplied to and registered in the image database 114, and the flow proceeds to step S277.

In step S277, the control unit 118 reads out the all-directional image data registered in the image database 114 in step S276 along with the header information, supplies this to the transmission unit 116 so as to cause the transmission unit 116 transmit this to the master moving entity transmitting the request signals. The flow then returns to step S271, and the same processing is repeated thereafter. Note that the request signal contains the moving entity ID of the moving entity which has transmitted the request signal, and in step S277 (as well as the later-described steps S282 and S288), the all-directional image data is transmitted with the moving entity ID as the destination thereof.

On the other hand, in step S272, in the event that determination is made that there is no moving entity ID contained in the request signal, the flow proceeds to step S278, where the control unit 118 makes determination whether or not one or more image-taking points are contained in the request signal. In the event that determination is made in step S278 that there are not image-taking points contained in the request signals, the flow returns to step S271, and the same processing is repeated thereafter.

On the other hand, in step S278, in the event that determination is made that one or more image-taking points are contained in the request signal, the flow proceeds to step S279, where the control unit 118 supplies the one or more image-taking points contained in the request signal to the storage unit 121 for storage.

Figure 49:
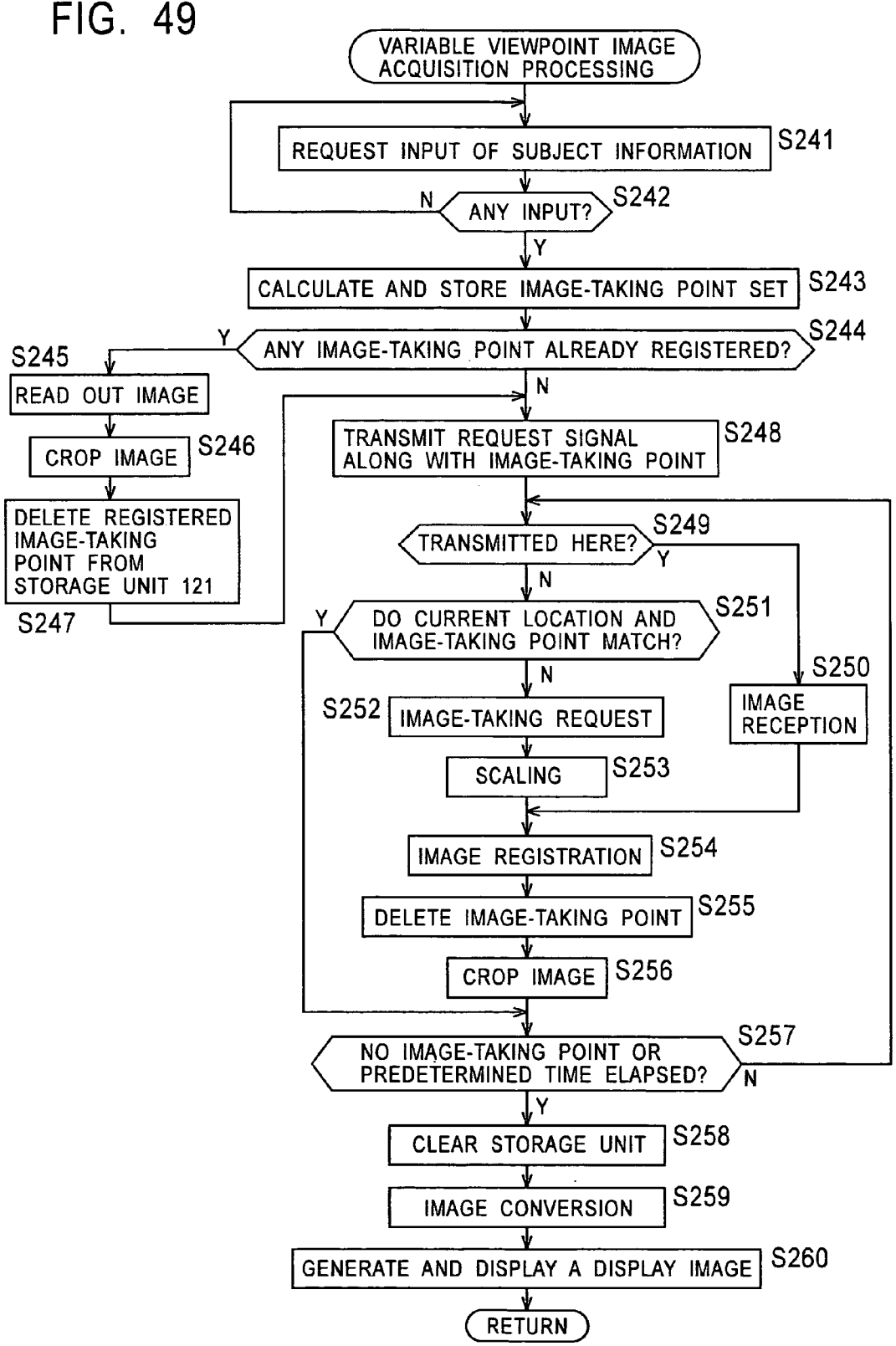
FIG. 49 is a flowchart describing viewpoint-variable image acquiring processing.
Figure 50:
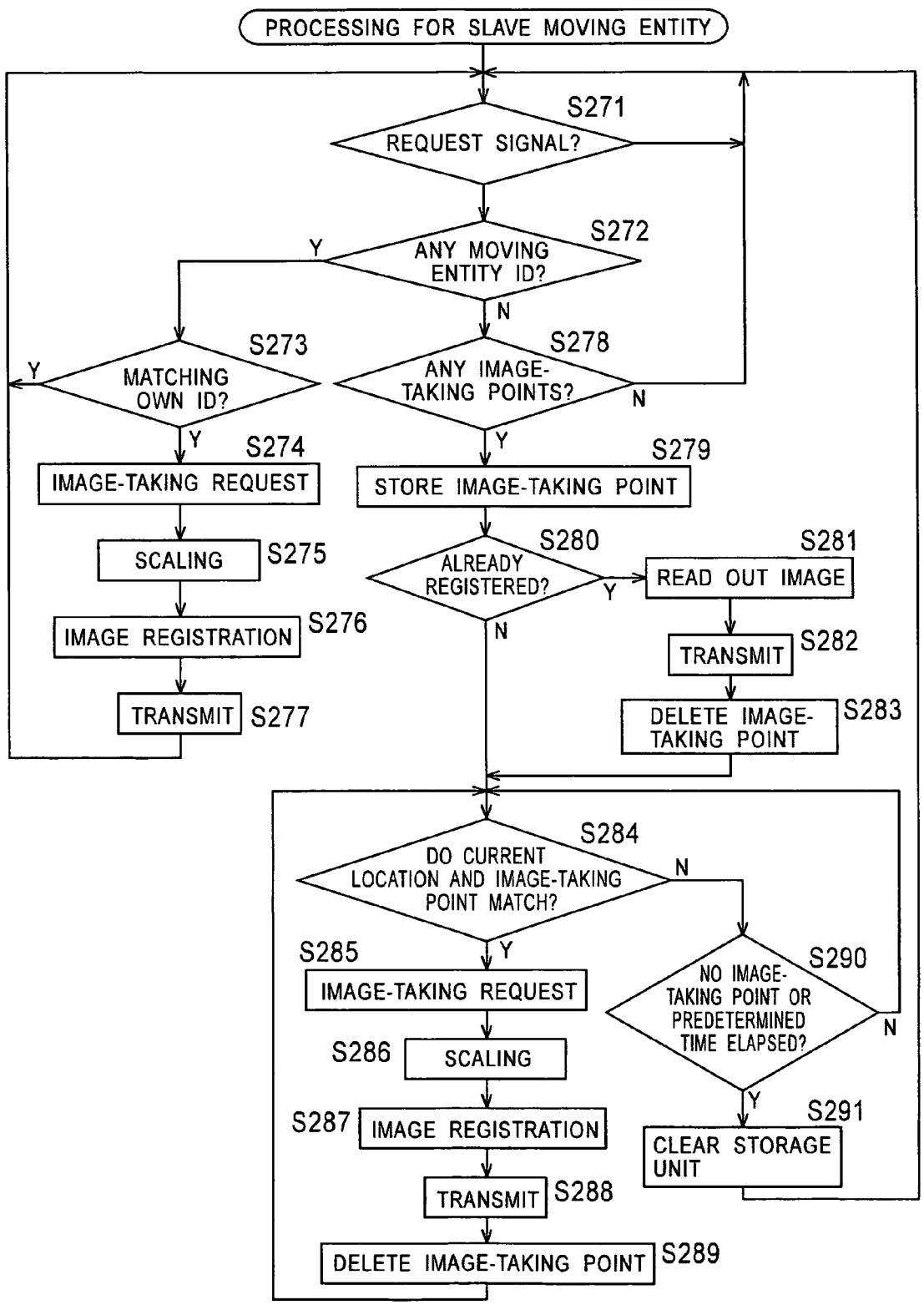
FIG. 50 is a flowchart describing processing of a slave moving entity.

Now, in the event that the viewpoint-specified image acquiring processing shown in FIG. 48 is to be performed at the master moving entity, only one image-taking point is included in the request signal, while in the event that the viewpoint-variable image acquiring processing shown in FIG. 49 is to be performed, one or more image-taking points are included in the request signal.

Subsequently, the flow proceeds to step S280, where the control unit 118 makes reference to the image database 114 to determine whether or not there is an image-taking point in the one or more image-taking points stored in the storage unit 121 which matches an image-taking point for all-directional image data stored in the image database 114.

In step S280, in the event that determination is made that there is an image-taking point in the one or more image-taking points stored in the storage unit 121 which matches an image-taking point for all-directional image data stored in the image database 114, i.e., in the event that all-directional image data taken from an image-taking point stored in the storage unit 121 has already been registered in the image database 114, the flow proceeds to step S282, the control unit 118 reads out the all-directional image data thereof from the image database 114, and the flow proceeds to step S282.

In step S282, the control unit 118 supplies the all-directional image data read out from the image database 114 to the transmission unit 116 with the header information thereof so as to cause the transmission unit 116 to transmit this to the master moving entity which transmitted the request signal. The flow then proceeds to step S283, where the control unit 118 deletes those of the one or more image-taking points stored in the storage unit 121 which match the image-taking points of the all-directional image data read out from the image database 114 in step S281, and the flow proceeds to step S284.

Note that in the event that there are multiple image-taking points stored in the storage unit 121 which match the image-taking points of the all-directional image data stored in the image database 114, the processing of the above-described steps S281 through S283 is performed regarding the multiple image-taking points.

On the other hand, in the event that determination is made in step S280 that there are no image-taking points stored in the storage unit 121 which match the image-taking points of the all-directional image data stored in the image database 114, i.e., in the event that all-directional image data requested by the master moving entity is not registered in the image database 114 of the slave moving entity, the flow proceeds to step S284, where the comparing unit 120 determines whether the current position matches one of the image-taking points stored in the storage unit 121, as described in step S226 in FIG. 48.

In the event that determination is made in step S284 that the current position matches one of the image-taking positions stored in the storage unit 121, i.e., in the event that the slave moving entity is situated at one of the image-taking positions contained in the request signal, the flow proceeds to step S285, and the control unit 118 makes an image-taking request to the image-taking device 111. The image-taking device 111 takes the all-directional image in response to the request from the control unit 118, and supplies this to the scaling unit 113 via the A/D converting unit 112.

Upon receiving supply of the all-directional image data, the scaling unit 113 converts (scales) the all-directional image data into all-directional image data of a fixed magnification in step S286, the flow proceeds to step S287, this is supplied to and registered in the image database 114, the flow proceeds to step S288.

In step S288, the control unit 118 reads out the all-directional image data registered in the image database 114 in step S287 along with the header information thereof, supplies this to the transmission unit 116 so as to cause the transmission unit 116 to transmit this to the master moving entity which has transmitted the request signals.

Subsequently, the flow proceeds to step S289, where the control unit 118 deletes those of the one or more image-taking points stored in the storage unit 121 which match the image-taking points of the all-directional image data stored in the image database 114 in step S287, and the flow returns to step S284.

On the other hand, in step S284, in the event that determination is made that the current location does not match any of the image-taking points stored in the storage unit 121, the flow proceeds to step S290, where the control unit 118 determines whether there are not image-taking points stored in the storage unit 121, and whether or not a predetermined amount of time has elapsed following receiving the request signal from the master moving entity. In step S290, in the event that determination is made that an image-taking point is stored in the storage unit 121, and that the predetermined amount of time has not elapsed since receiving the request signal, the flow returns to step S284, and the same processing is repeated.

Also, in step S290, in the event that determination is made that there is no image-taking point stored in the storage unit 121, or that the predetermined amount of time has elapsed since transmitting the request signal, i.e., that all of the all-directional image data taken from the one or more image-taking points contained in the request signal has been transmitted to the master moving entity, or that part or all of the all-directional image data taken from each of the one or more image-taking points contained in the request signal is not obtained after a predetermined amount of time has elapsed following reception of the request signal, the flow proceeds to step S291, where the control unit 118 clears the stored contents of the storage unit 121. The flow then returns to step S271, where the same processing is repeated thereafter.

As described above, the slave moving entity takes the all-directional image data with the current location as the image-taking point and transmits this to the master moving entity, in the event that its own moving entity ID is contained in the request signal. Also, in the event that one or more image-taking points are contained in the request signal and all-directional image data of the image-taking points is stored in the image database 114, the slave moving entity transmits the all-directional image data to the master moving entity, and in the event that this is not stored and the own current location matches an image-taking point, takes the all-directional image data at the current location which is the image-taking point and transmits this to the master moving entity.

Accordingly, in a case of including the moving entity ID in the request signal, the master moving entity can obtain all-directional image data taken at the current location of the slave moving entity, from the slave moving entity of that moving entity ID (first function).

Also, in the event that the master moving entity has transmitted the request signal including one image-taking point, all-directional image data which a slave moving entity has taken at the current location thereof can be obtained from a slave moving entity of which the current location is the image-taking point. Or, the master moving entity can obtain from a slave moving entity having all-directional image data of an image-taking point contained in the request signal, the all-directional image data. As a result, the master moving entity can obtain all-directional image data containing a desired subject viewed from a desired viewpoint direction (second function).

Also, in the event that the master moving entity has transmitted the request signal including multiple image-taking points, all-directional image data which multiple slave moving entities have taken at the current locations thereof can be obtained from multiple slave moving entities of which the current locations are the image-taking points. Or, the master moving entity can obtain from slave moving entities having all-directional image data of the image-taking points contained in the request signal, the all-directional image data. As a result, the master moving entity can obtain all-directional image data containing a desired subject viewed from multiple viewpoint directions, and further, can obtain viewpoint-variable images which is a moving picture wherein the desired subject is viewed over from therearound, from the multiple all-directional image data sets.

That is, with the all-directional cameras $102_1$, $102_2$, ..., $102_K$, of the moving entities $101_1$, $101_2$, ..., $101_K$, individually obtaining a viewpoint-variable image necessitates moving around the subject and taking the subject from multiple directions, thereby obtaining multiple sets of all-directional image data, so a viewpoint-variable image cannot be immediately obtained.

Accordingly, with the SHARN moving entity system, multiple moving entities collaborate (cooperate) with each other so as to obtain all-directional image data taken from each of multiple image-taking points. That is, the master moving entity requests the all-directional image data taken from each of multiple image-taking points from the slave moving entities, and slave moving entities having the all-directional image data or slave moving entities capable of taking the all-directional image data provide the all-directional image data to the master moving entity.

In this way, the master moving entity obtains the necessary all-directional image data through the cooperation of slave moving entities having the necessary all-directional image data or slave moving entities capable of taking the necessary all-directional image data, and thereby is capable of obtaining a viewpoint-variable image which could not be obtained with it own camera alone, that is to say, to obtain a moving picture which is not simply of a subject but has the added value of the subject appearing as if it had been taken while moving around the subject.

Figure 51:
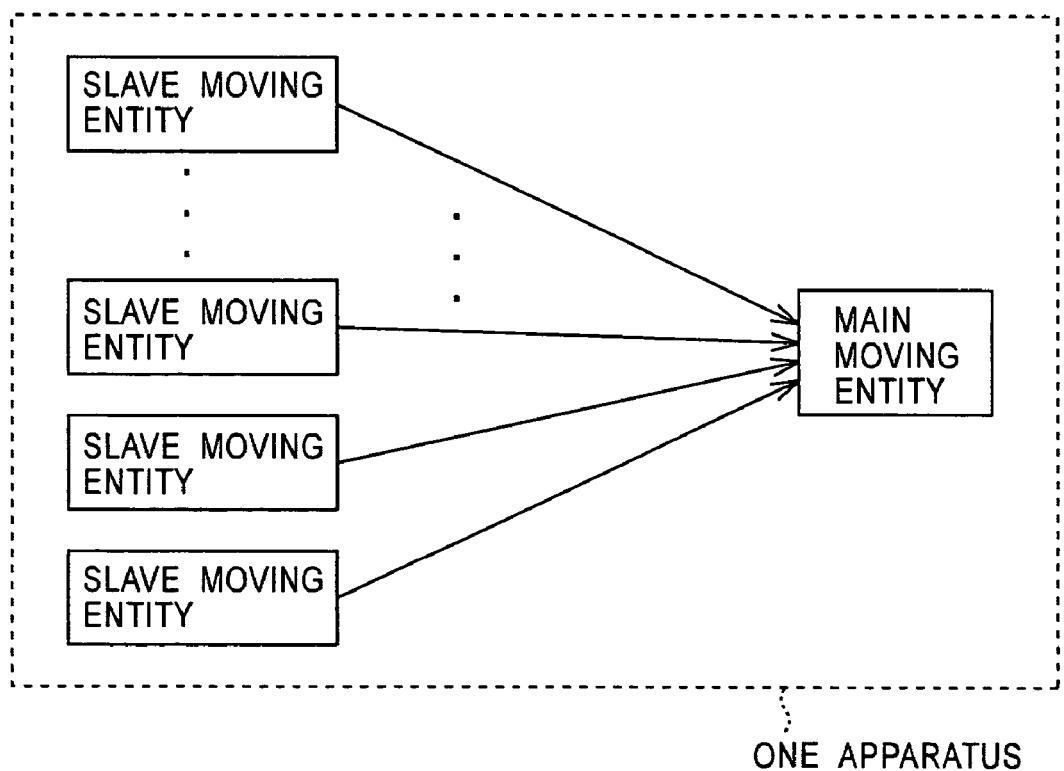
FIG. 51 is a diagram describing collaboration sharing in the SHARN moving entity system.

Accordingly, generating (taking) viewpoint-variable images can be realized at the master moving entity, which was difficult with the all-directional camera thereof alone, the reason thereof being that the master moving entity and one or more slave moving entities act as if they were a single apparatus as indicated by being surrounded by the dotted line in FIG. 51, such that the slave moving entities provide the all-directional image data of the image-taking points which the master moving entity requests, and the master moving entity generates viewpoint-variable image data using the all-directional image data provided from the slave moving entities in this way, whereby consequently the all-directional cameras of the multiple moving entities share the task of taking (generating) viewpoint-variable image data through mutual collaboration.

Conversely, in the event that the slave moving entities simply provided arbitrarily taken all-directional image data to the master moving entity, this is simply sharing the task of collecting all-directional image data among the slave moving entities, so images necessary for generating a viewpoint-variable image cannot be obtained at the master moving entity, and accordingly, the high-functionality of generating the viewpoint-variable image cannot be realized.

Note that with the SHARN moving entity system, in the event of each of the all-directional cameras of multiple moving entities sharing the processing of taking (generating) viewpoint-variable image data through mutual collaboration, the viewpoint-variable image data can be immediately obtained, so taking note of this point, it can be said that real-time collaboration sharing is being performed, as if it were.

On the other hand, with the SHARN moving entity system, due to the real-time collaboration sharing being carried out such as described above, all-directional image data taken at multiple image-taking points necessary for generating a variable-variable image of a predetermined subject is accumulated at the image database 114 of the moving entity which is the master moving entity. Consequently, in the event that the requests for generating viewpoint-variable images is great for a predetermined subject, viewpoint-variable images with high time-resolution can be generated according to the number of times of request.

That is, for example, in the event of generating a viewpoint-variable image which circles around the subject in 3 seconds with a frame rate of 30 frames/second, ideally, 90 images taking the subject from viewpoints which differ by 4° each (different direction images), and upon the 90 different direction images being collected, a viewpoint-variable image with the highest time-resolution can be obtained under the conditions of circling around the subject in 3 seconds with a frame rate of 30 frames/second.

In this case, there is the need to obtain all-directional images taken at 90 image-taking points (90 all-directional images which are different-direction images), and assuming there is no all-directional image data in any of the image databases 114 of all of the moving entities in order to simplify description, even if one moving entity A transmits request signals including the 90 image-taking points for the predetermined subject in the viewpoint-variable image acquiring processing (FIG. 49), there is no guarantee that there will be moving entities at each of the 90 locations, and accordingly, generally, not all of the all-directional images taken at the 90 image-taking points will be collected.

However, saying that the all-directional images of 30 image-taking points, which is ⅓ of the 90 image-taking points, have been collected and registered in the image database 114 of the moving entity A for example, by the viewpoint-variable image acquiring processing by the moving entity A, in the event that another moving entity B subsequently transmits a request signal including the 90 image-taking points for the predetermined subject, in the viewpoint-variable image acquiring processing (FIG. 49), this moving entity B will be able to obtain at least the 30 all-directional images registered in the image database 114 of the moving entity A. Further, in this case, there is high probability that other moving entities are situated at some of the remaining 60 image-taking points, so the moving entity B can obtain the all-directional images taken from some of the remaining 60 image-taking portions, from such moving entities.

Accordingly, in the event that there is a request for generating viewpoint-variable images from multiple moving entities for a predetermined subject, all-directional images of a great number of image-taking points are obtained according to the number of times of request, and consequently, viewpoint-variable images with high time-resolution are generated.

In this way, with regard to subjects regarding which there are many requests for generating viewpoint-variable images, viewpoint-variable images having the added value of high time-resolution are generated according to the number of times of request, which is due to the multiple all-directional cameras of the multiple moving entities performing the processing of taking (generating) viewpoint-variable image data through mutual collaboration. However, taking note of generating viewpoint-variable images with the added value of high time-resolution, the high time-resolution is realized by requests for generating viewpoint-variable images of the predetermined subject being made many times, so passing of a certain amount of time is necessary, and accordingly, it can be said the long-term collaboration sharing is carried out with regard to the above-described real-time collaboration sharing.

Note that while in the above-described case, image-taking is performed with an all-directional camera $102_k$ from the moving entity $101_k$, but an arrangement may be made wherein the moving entity $101_k$ takes pictures with a normal camera.

Also, ships or aircraft or the like may be employed as the moving entity $101_k$, besides automobiles.

Further, while in the above-described case, viewpoint-variable images which appear as if the image was taken while circling the subject are generated as the added-value images with the SHARN moving entity system, but other examples of added-value images include, for example, generating a three-dimensional image using so-called triangulation surveying.

Next, the above-described series of processing may be carried out by hardware, or may be carried out by software. In the event of carrying out the series of processing with software, a program making up the software is installed in an general-purpose computer or the like.

Figure 52:
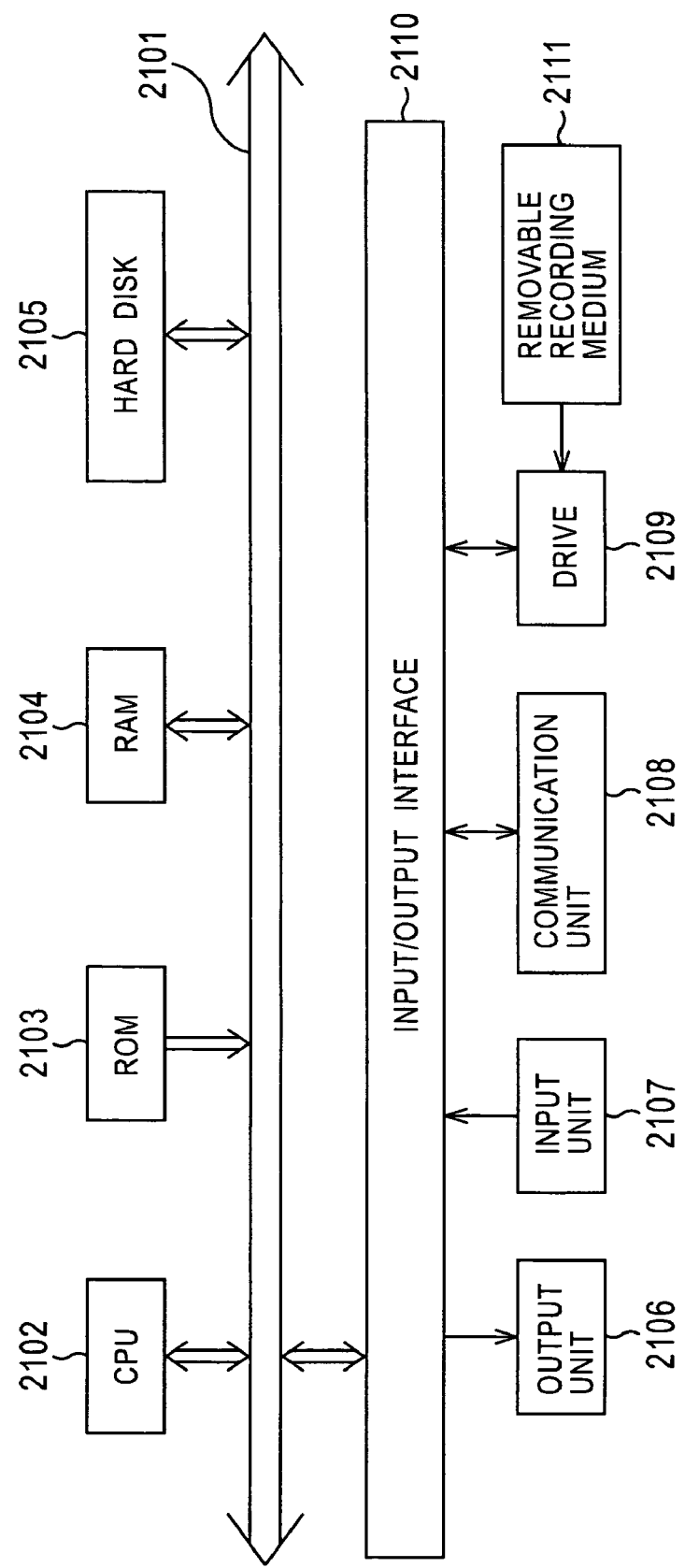
FIG. 52 is a block diagram illustrating a configuration example of an embodiment of a computer to which the present invention has been applied.

Accordingly, FIG. 52 illustrates a configuration example of an embodiment of a computer to which the program for executing the above-described series of processing is installed.

The program can be stored beforehand in a hard disk 2105 or ROM 2103 serving as recording media built into the computer.

Or, the program may be temporarily or permanently stored (recorded) in a removable recording medium 2111 such as a flexible disk, CD-ROM (Compact Disk Read Only Memory), MO (Magneto optical) disk, DVD (Digital Versatile Disk), magnetic disk, semiconductor memory, or the like. Such removable recording media 2111 can be provided as so-called packaged software.

Note that besides being installed into the computer from such a removable recording medium 2111 as described above, the program may be transmitted from a download site to the computer wirelessly via a satellite for digital satellite broadcast, or transmitted through cable to the computer via a network such as a LAN (Local Area Network), the Internet, or the like, and installed to the internal hard disk 2105 of the computer by receiving the program being transmitted in such a way with a communication unit at the computer.

The computer has a built-in CPU (Central Processing Unit) 2102. An input/output interface 2110 is connected to the CPU 2102 via the bus 2101, and upon commands being input by a user operating or the like an input unit 2107 comprises a keyboard, mouse, microphone, etc., the programs stored in ROM (Read Only Memory) 2103 is executed accordingly. Or, the CPU 2102 loads to RAM (Random Access Memory) 2104 and executes the program stored in the hard disk 2105, the program transmitted from satellite or network and received by the communication unit 2108 and installed in the hard disk 2105, or the program installed in the hard disk 2105 by being read out from a removable recording medium 2111 mounted to the drive 2109. Accordingly, the CPU 2102 carried out processing following the above-described flowcharts, or processing performed by the above-described block diagram configurations. The processing results of the CPU 2102 are output from an output unit 2106 configured of a LCD (Liquid crystal Display) and speaker or the like, transmitted from the communication unit 2108, recorded in the hard disk 2105, or the like, via the input/output interface 2110, for example, as necessary.

Now, with the present specification, the processing steps describing the program for causing the computer to carry out the various types of processing do not necessarily need to be processed in time-sequence following the order given in the flowcharts, and may include parallel or individually executed processing (for example, parallel processing or processing by object).

Also, the program may be processed by a single computer, or may be processed in a scattered manner among multiple computers. Further, the program may be transferred to and executed on a remote computer.

INDUSTRIAL APPLICABILITY

According to the information processing system, first information processing method, first program and first recording medium according to the present invention, multiple acting means or multiple detecting means share processing through collaboration, so the functionality of an information processing system is raised.

According to the information processing device, second information processing method, second program and second recording medium according to the present invention, acting means or detecting means share processing through collaboration with another information processing device, so the functionality of an information processing device is raised.

The invention claimed is:

1. An information processing system comprising:
a plurality of actuators configured to act corresponding to operations by a plurality of users;
a plurality of detectors configured to detect the real world where said plurality of actuators act;
a communication unit configured to exchange information between said plurality of actuators and said plurality of detectors;
a storage unit configured to store results from acting by said plurality of actuators or results from detecting by said plurality of detectors;
a comparing unit for comparing:
a present result from acting by one or more of said plurality of actuators with a past result from acting by one or more of said plurality of actuators and stored in said storage unit; and
a present result from detecting by one or more of said plurality of detectors with a past result from detecting by one or more of said plurality of detectors and stored in said storage unit;
an integrating unit configured to integrate the present result from acting by one or more of said plurality of actuators or the present result from detecting by one or more of said plurality of detectors and the past results from acting by one or more of said plurality of actuators or the past results from detecting by one or more of said plurality of detectors according to a result of said comparing, and outputting as an integrated result from acting or an integrated result from detecting,
wherein the integrated result accounts for past results comprising attitude parameters that are weighted according to a degree of experience of a user operating each of the plurality of actuators, and
wherein said plurality of actuators and said plurality of detectors share processing through collaboration, whereby said plurality of actuators of said plurality of detectors are more highly functional as compared to operating individually.

2. An information processing system according to claim 1, wherein said plurality of actuators act corresponding to multiple user operations and predetermined information; and
a communication unit receives the state of said plurality of actuators detected by said plurality of detectors;
said system further comprising a generator unit configured to generate, as said predetermined information, reference information to serve as a reference regarding the action of said plurality of actuators, based on the state of said plurality of actuators.

3. An information processing system according to claim 2, further comprising:
a second storage unit configured to store said reference information; and
an updating unit configured to update the stored contents of said second storage unit with new said reference information generated by said generator unit.

4. An information processing system according to claim 2, wherein said generator unit generates said reference information based on the state of said plurality of actuators and external information.

5. An information processing system according to claim 2, further comprising a control unit configured to control the actions of one or more of said plurality of actuators based on said reference information, so that said one or more actuators have higher functionality than acting alone.

6. An information processing system according to claim 2, wherein one or more of said plurality of actuators is a manipulator.

7. An information processing system according to claim 6, wherein the manipulator is a master manipulator which controls a slave manipulator which acts upon a predetermined object.

8. An information processing system according to claim 7, wherein said reference information is information for restricting the action directed to said predetermined object.

9. An information processing system according to claim 7, wherein said reference information is information for performing surgery upon said predetermined object.

10. An information processing system according to claim 7, wherein said reference information is information regarding design of said predetermined object.

11. An information processing system according to claim 1, wherein the functionality of said plurality of detectors is increased.

12. An information processing system according to claim 11,
wherein said plurality of actuators are a plurality of moving entities which move according to operations of multiple users;
wherein said plurality of detectors are provided on said plurality of moving entities and detect a subject to be imaged; and
wherein said communication unit receives output of said plurality of detectors;
said system further comprising a generation unit configured to generate information with added value added, by processing the output of said plurality of detectors.

13. An information processing system according to claim 12, wherein said detectors are image-taking devices for taking images of a subject.

14. An information processing system according to claim 13,
wherein said communication unit receives an image of said subject output by said image-taking devices; and wherein said generator unit generates an image viewing said subject from multiple direction, which is an image with higher added value as compared to an image obtained from a single image-taking device, by processing the image of said subject.

15. An information processing system according to claim 13,
    wherein, of said multiple moving entities, one moving entity transmits to other moving entities a request signal for requesting images of said subject; and
    wherein said other moving entities transmit images of said subject to said one moving entity, in response to said request signal.

16. An information processing system according to claim 15, wherein said one moving entity calculates an image-taking position for image-taking of said subject, based on the position of said subject, and the image-taking direction of said subject, and transmits said request signal along with the image-taking position.

17. An information processing system according to claim 16, wherein said other moving entities take images of said subject at the point that the current position thereof matches said image-taking position by said image-taking devices.

18. An information processing system according to claim 17,
    wherein said other moving entities transmit said image-taking position to said one moving entity along with images taken of said subject; and
    wherein said one moving entity processes the images of said subject from said other moving entities based on said image-taking positions transmitted with the images, thereby generating an image wherein said subject is viewed from multiple directions.

19. An information processing system according to claim 13, wherein said image-taking devices include an all-directional camera capable of taking images omni-directionally.

20. An information processing method comprising the steps of:
    performing actions corresponding to operations by a plurality of users;
    detecting the real world where a plurality of actuators act; and
    exchanging information between said plurality of actuators and a plurality of detectors;
    storing results from acting or results from detecting;
    comparing a present result from acting or a present result from detecting with past results from acting and stored during the storing step or past results from detecting and stored during the storing step;
    integrating the present result from acting or the present result from detecting and the past results from acting or the past results from detecting according to a result of said comparing; and
    outputting as an integrated result from acting or an integrated result from detecting,
    wherein the integrated result accounts for past results comprising attitude parameters that are weighted according to a degree of experience of a user operating each of the plurality of actuators, and
    wherein said plurality of actuators and said plurality of detectors share processing through collaboration, whereby said plurality of actuators or said plurality of detectors are more highly functional as compared to operating individually.

21. A non-transitory recording medium storing a computer-readable program for controlling a computer such that:
    a plurality of actuators act corresponding to operations by a plurality of users;
    a plurality of detectors detect the real world where said plurality of actuators act; and
    communication units exchange information between said plurality of actuators and said plurality of detectors;
    a storage unit stores results from acting by said plurality of actuators or results from detecting by said plurality of detectors;
    a comparator compares a present result from acting by said plurality of actuators or a present result from detecting by said plurality of detectors with past results from acting by said plurality of actuators and stored in said storage unit or past results from detecting by said plurality of detectors and stored in said storage unit; and
    an integrator configured to integrate the present result from acting by one or more of said plurality of actuators or the present result from detecting by one or more of said plurality of detectors and the past results from acting by one or more of said plurality of actuators or the past results from detecting by one or more of said plurality of detectors according to a result of said comparing, and outputs as an integrated result from acting or an integrated result from detecting,
    wherein the integrated result accounts for past results comprising attitude parameters that are weighted according to a degree of experience of a user operating each of the plurality of actuators, and
    wherein one or more of said plurality of actuators and one or more of said plurality of detectors share processing through collaboration, whereby one or more of said plurality of actuators or one or more of said plurality of detectors are more highly functional as compared to operating individually.

22. An information processing device comprising:
    one or more actuators configured to act corresponding to operations by a user;
    one or more detectors configured to detect the real world where said one or more actuators acts;
    a communication unit configured to exchange information between one or more actuators and one or more detectors;
    a storage unit configured to store results from acting by said one or more actuators or results from detecting by said one or more detectors;
    a comparator configured to compare a present result from acting by the one or more actuators or a present result from detecting by said one or more detectors with past results from acting by one or more actuators and stored in said storage unit or past results from detecting by one or more detectors and stored in said storage unit; and
    an integrator configured to integrate the present result from acting by one or more actuators or the present result from detecting by one or more detectors and the past results from acting or the past results from detecting by said one or more detectors according to a result of said comparing, and outputting as an integrated result from acting or an integrated result from detecting,
    wherein the integrated result accounts for past results comprising attitude parameters that are weighted according to a degree of experience of a user operating each of the plurality of actuators, and
    wherein said one or more actuators and said one or more detectors share processing with one or more said actuators and one or more said detectors through collaboration, whereby said one or more actuators or said one or more detectors are more highly functional as compared to operating individually.

23. An information processing device according to claim 22, wherein the functions of said one or more actuators become highly functional.

24. An information processing device according to claim 23,
wherein said one or more actuators act corresponding to user operations and predetermined information; and
wherein said communication unit receives the state of said one or more actuators detected by said one or more detectors;
said device further comprising a generator configured to generate, as said predetermined information, reference information to serve as a reference regarding the action of said one or more actuators, based on the state of said one or more actuators.

25. An information processing device according to claim 24, further comprising:
a memory unit configured to store said reference information; and
an updating unit configured to update the stored contents of said memory with new said reference information generated by said generator.

26. An information processing device according to claim 24, wherein said generator generates said reference information based on the state of said one or more actuators and external information.

27. An information processing device according to claim 24, further comprising a controller configured to control the actions of the one or more actuators based on said reference information, so that one or more actuators has higher functionality than acting alone.

28. An information processing device according to claim 24, wherein said at least on of the one or more actuators is a manipulator.

29. An information processing device according to claim 28, wherein the manipulator is a master manipulator which controls a slave manipulator which acts upon a predetermined object.

30. An information processing device according to claim 29, wherein said reference information is information for restricting the action directed to said predetermined object.

31. An information processing device according to claim 29, wherein said reference information is information for performing surgery upon said predetermined object.

32. An information processing device according to claim 29, wherein said reference information is information regarding design of said predetermined object.

33. An information processing device according to claim 22, wherein the functionality of at least one of said one or more detectors is increased.

34. An information processing device according to claim 33,
wherein said one or more actuators include a moving entity which moves according to operations of multiple users;
wherein said one or more detectors are provided on said moving entity and detect a subject to be imaged; and
wherein said communication unit receive output of said at least one of the one or more detectors;
said device further comprising:
a generator configured to generate information with added value added, by processing the output of said at least one detector and a second detector.

35. An information processing device according to claim 34, wherein said detectors are image-obtaining units configured to obtain one or more images of a subject.

36. An information processing device according to claim 35,
wherein said communication unit receives an image of said subject output by said image obtaining units; and
wherein said generator generates an image that provides viewing of said subject from multiple directions, which is an image with higher added value compared to an image obtained from a single image-obtaining unit, by processing the image of said subject.

37. An information processing device according to claim 35,
wherein said communication unit transmits to other moving entities a request signal for requesting images of said subject; and receives images of said subject taken by said second detector of said other moving entity, in response to said request signal.

38. An information processing device according to claim 37,
wherein said communication unit calculates an image-obtaining position for obtaining one or more images of said subject, based on the position of said subject, and the image-taking direction of said subject, and transmits said request signal along with the image-taking position.

39. An information processing device according to claim 38, wherein, at the point that the current position thereof matches said image-obtaining position, said communication unit receive images of said subject, taken by said image-obtaining unit of other moving entities.

40. An information processing device according to claim 39, wherein said communication unit processes the images of said subject transmitted from said other moving entities, based on said image-obtaining positions transmitted with the images, thereby generating an image wherein said subject is viewed from multiple directions.

41. An information processing device according to claim 35, wherein said image-obtaining unit is an omni-directional camera capable of taking images omni-directionally.

42. An information processing method comprising the steps of:
performing an action corresponding to operations by a plurality of users;
detecting real world conditions where said actions occur, and information is exchanged between one or more actuators and one or more detectors;
storing results from acting or results from detecting;
comparing a present result from acting or a present result from detecting with past results from acting and stored during the storing step or past results from detecting and stored during the storing step;
integrating the present result from acting or the present result from detecting and the past results from acting or the past results from detecting according to a result of said comparing;
wherein the integrated result accounts for past results comprising attitude parameters that are weighted according to a degree of experience of a user operating each of the plurality of actuators, and
outputting as an integrated result from acting or an integrated result from detecting; and
sharing processing between a first set of actuators and a first set of detectors and a second set of actuators and a second set of detectors through collaboration, thereby the first set of actuators, first set of detectors, second set of actuators and second set of detectors are more highly functional as compared to operating individually.

43. A non-transitory computer-readable medium for storing a computer-readable program for controlling a computer such that when executed the program causes the computer to:
- act corresponding to operations by a plurality of users;
- detect the real world where said acting occurs; and
- exchange information between actuators and detectors;
- store results from the actuators or results from the detectors;
- compare a present result from the actuators or a present result from the detectors with past results from acting by said plurality of the actuators or past results from detecting by said plurality of detectors; and
- integrate the present result from acting by said actuators or the present result from detecting by said detectors and the past results from acting by said plurality of actuators or the past results from detecting by said plurality of detectors according to a result of said comparing,
- wherein the integrated result accounts for past results comprising attitude parameters that are weighted according to a degree of experience of a user operating each of the plurality of actuators; and
- output as an integrated result from acting or an integrated result from detecting,
- wherein said actuators and said detectors share processing through collaboration, thereby becoming more highly functional as compared to operating individually.

\* \* \* \* \*